US012163192B2

(12) United States Patent
Backman et al.

(10) Patent No.: US 12,163,192 B2
(45) Date of Patent: *Dec. 10, 2024

(54) PIEZO TYPE MECHANOSENSITIVE ION CHANNEL COMPONENT 1 (PIEZO1) VARIANTS AND USES THEREOF

(71) Applicant: Regeneron Pharmaceuticals, Inc., Tarrytown, NY (US)

(72) Inventors: Joshua Backman, Tarrytown, NY (US); Aris Baras, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/096,232

(22) Filed: Jan. 12, 2023

(65) Prior Publication Data
US 2023/0287502 A1 Sep. 14, 2023

Related U.S. Application Data

(63) Continuation of application No. 16/785,152, filed on Feb. 7, 2020, now Pat. No. 11,584,966.

(60) Provisional application No. 62/862,847, filed on Jun. 18, 2019, provisional application No. 62/806,932, filed on Feb. 18, 2019.

(51) Int. Cl.
| | |
|---|---|
| *C12Q 1/6883* | (2018.01) |
| *A61K 31/192* | (2006.01) |
| *A61K 31/616* | (2006.01) |
| *A61P 9/14* | (2006.01) |
| *C12N 15/10* | (2006.01) |
| *C12Q 1/6827* | (2018.01) |

(52) U.S. Cl.
CPC .......... *C12Q 1/6883* (2013.01); *A61K 31/192* (2013.01); *A61K 31/616* (2013.01); *A61P 9/14* (2018.01); *C12N 15/1096* (2013.01); *C12Q 1/6827* (2013.01); *C12Q 2600/156* (2013.01)

(58) Field of Classification Search
CPC ................ C12Q 1/6883; C12Q 1/6827; C12Q 2600/156; A61P 9/14; A61K 31/192; A61K 31/616; C12N 15/1096
USPC .......................................... 514/27
See application file for complete search history.

(56) References Cited

U.S. PATENT DOCUMENTS 11,584,966 B2 * 2/2023 Backman ........... C12N 15/1096

FOREIGN PATENT DOCUMENTS

WO 2020171982 8/2020

OTHER PUBLICATIONS

Mishra et al. Pharmacological and Therapeutic Activity of Cissus quadrangularis: An Overview. International Journal of PharmTech Research vol. 2, No. 2, pp. 1298-1310, Apr.-Jun. 2010. (Year: 2010).*
Fotiou et al., "Novel mutations in PIEZO1 cause an autosomal recessive generalized lymphatic dysplasia with non-immune hydrops fetalis", Nat Commun, 2015, 6, pp. 1-6.
Smetaina et al., "Differentially Expressed Genes in Varicose Veins Disease: Current State of the Problem, Analysis of the Published Data", Abstract, Flebologia, 2017, 11(4), pp. 190-202.
International Search Report and Written Opinion mailed Nov. 9, 2022 for International Patent Application No. PCT/US2022/073441.
Douguet et al., "Piezo Ion Channels in Cardiovascular Mechanobiology" Trends in Pharmacological Sciences, 2019, 40(12), pp. 956-970.
Van Hout et al., "Exome sequencing and characterization of 49,960 individuals in the UK Biobank", Nature, 2020, 586, pp. 749-756.
Botello-Smith et al., "A mechanism for the activation of the mechanosensitive Piezo1 channel by the small molecule Yoda1", Nature Communications, 2019, 10(4503), pp. 1-9.
Anonymous, "16_88727995_G_A Open Targets Genetics", 2018, https://genetics.opentargets.org/variant/16_88727995_G_A.
Anonymous, "16_88730362_G_GGGAGGC Open Targets Genetics", 2018, https://genetics.opentargets.org/variant/16_88730362_G_GGGAGGC.
Fukaya et al., "Clinical and Genetic Determinants of Varicose Veins: Prospective, Community-Based Study of ~500? 000 Individuals", Circulation, 2018, 138(25), pp. 2869-2880.
Shadrina et al., "Abstract; Supplementary table 2; Supplementary table 3; Suppl. table 5A", bioRxiv, 2018, http://www.biorxiv.org/content/10.1101/368365v1.
Shadrina et al., "Varicose veins of lower extremities: Insights from the first large-scale genetic study", PLOS Genetics, 2019, 15(4), pp. e1008110.
International Search Report and Written Opinion mailed May 25, 2020 for International Patent Application No. PCT/US2020/017267.
Glossary of medical education terms, Institute of International Medical Education, http://www.iime.org/glossary/htm, 2013.
Smetanina et al., "The genetic constituent of varicose vein pathogenesis as a key for future treatment option development", Vessel Plus, 2021, 5(19), pp. 1-13.
Batchvarov et al., "One-Year Diosmin Therapy (600 MG) in Patients with Chronic Venous Insufficiency-Results and Analysis", J Biomed Clin Res, 2010, 3(1), pp. 51-54.
Martin-Almedina et al., "Human phenotype caused by PIEZO1 mutations, one gene, two overlapping phenotypes?", J Physiol, 2018, 596.6, pp. 985-992.
Bell et al., "A large scale genome wide association study of varicose veins in the 23andMe cohort", The 64th Annual Meeting of The American Society of Human Genetics, San Diego, California, USA, 2014.

(Continued)

Primary Examiner — Yih-Horng Shiao
(74) Attorney, Agent, or Firm — Armstrong Teasdale LLP

(57) ABSTRACT

Methods of treating patients having varicose veins, methods of identifying subjects having an increased risk of developing varicose veins, and methods of diagnosing varicose veins in a human subject, comprising detecting the presence of Piezo Type Mechanosensitive Ion Channel Component 1 (PIEZO1) predicted loss-of-function variant nucleic acid molecules and polypeptides in a biological sample from the patient or subject, are provided herein.

9 Claims, 6 Drawing Sheets

Specification includes a Sequence Listing.

(56) References Cited

OTHER PUBLICATIONS

Shadrina et al., "Varicose veins of lower extremities: Insights from the first large-scale genetic study", bioRxiv, 2018, pp. 1-41.

* cited by examiner

Single-point and aggregate results for the 65 pLOF variants in PIEZO1

| Single-point analysis | | | | | | | | | Functional Effect | Drop one - RVT | |
|---|---|---|---|---|---|---|---|---|---|---|---|
| SNPID (rsID) | Ref | Alt | AAF | Beta | SE | P-Val | MAC | | | P-Val LOO Burden | Delta P-Val Burden |
| 16:88727163:G:A | G | A | 6.9E-05 | 2.81 | 0.88 | 0.001 | 6 | | stop gained | 1.06E-06 | 33.91 |
| 16:88721586:G:C | G | C | 1.1E-05 | 14.63 | 119.5 | 0.903 | 1 | | stop gained | 2.63E-07 | 8.45 |
| 16:88716874:G:A | G | A | 1.1E-05 | 14.40 | 119.5 | 0.904 | 1 | | stop gained | 2.59E-07 | 8.31 |
| 16:88738735:D:1 | TC | T | 1.1E-05 | 13.95 | 119.5 | 0.907 | 1 | | frameshift | 2.45E-07 | 7.86 |
| 16:88721268:D:1 | CT | C | 1.1E-05 | 13.90 | 119.5 | 0.907 | 1 | | frameshift | 2.43E-07 | 7.80 |
| 16:88726546:C:T | C | T | 1.1E-05 | 13.67 | 119.5 | 0.909 | 1 | | splice donor | 2.34E-07 | 7.49 |
| 16:88723253:G:A (rs368895635) | G | A | 2.3E-05 | 3.77 | 1.42 | 0.008 | 2 | | stop gained | 2.31E-07 | 7.42 |
| 16:88719588:G:A | G | A | 1.1E-05 | 13.57 | 119.5 | 0.910 | 1 | | stop gained | 2.29E-07 | 7.35 |
| 16:88720229:C:A | C | A | 1.1E-05 | 13.55 | 119.5 | 0.910 | 1 | | stop gained | 2.28E-07 | 7.32 |
| 16:88727072:D:1 | TC | T | 2.3E-05 | 3.59 | 1.42 | 0.011 | 2 | | frameshift | 2.22E-07 | 7.12 |
| 16:88716359:A:G (rs776709730) | A | G | 2.3E-05 | 3.15 | 1.42 | 0.026 | 2 | | splice donor | 1.94E-07 | 6.23 |
| 16:88736324:G:A | G | A | 4.6E-05 | 2.48 | 1.18 | 0.035 | 4 | | stop gained | 1.67E-07 | 5.35 |

Figure 4

LD Assessment for PIEZO1

| Variant | LD(R²) | 1 | 2 | 3 | 4 | 5 | 6 | 7 | 8 | 9 | 10 | 11 | 12 |
|---|---|---|---|---|---|---|---|---|---|---|---|---|---|
| 1 | 16:88716359:A:G | 1 | 1.1E-9 | 1.1E-9 | 1.1E-9 | 1.1E-9 | 2.1E-9 | 1.1E-9 | 2.1E-9 | 6.3E-9 | 4.2E-9 | 1.1E-9 | 2.1E-4 |
| 2 | 16:88716874:G:A | | 1 | 5.2E-10 | 5.2E-10 | 5.2E-10 | 1.1E-9 | 5.2E-10 | 1.1E-9 | 3.1E-9 | 2.1E-9 | 5.2E-10 | 2.1E-5 |
| 3 | 16:88719588:G:A | | | 1 | 5.2E-10 | 5.2E-10 | 1.1E-9 | 5.2E-10 | 1.1E-9 | 3.1E-9 | 2.1E-9 | 5.2E-10 | 8.1E-6 |
| 4 | 16:88721268:D:1 | | | | 1 | 5.2E-10 | 1.1E-9 | 5.2E-10 | 1.1E-9 | 3.1E-9 | 2.1E-9 | 5.2E-10 | 8.1E-6 |
| 5 | 16:88721586:G:C | | | | | 1 | 1.1E-9 | 5.2E-10 | 1.1E-9 | 3.1E-9 | 2.1E-9 | 5.2E-10 | 8.1E-6 |
| 6 | 16:88723253:G:A | | | | | | 1 | 1.1E-9 | 2.1E-9 | 6.3E-9 | 4.2E-9 | 1.1E-9 | 1.6E-5 |
| 7 | 16:88726546:C:T | | | | | | | 1 | 1.1E-9 | 3.1E-9 | 2.1E-9 | 5.2E-10 | 2.1E-5 |
| 8 | 16:88727072:D:1 | | | | | | | | 1 | 6.3E-9 | 4.2E-9 | 1.1E-9 | 1.6E-5 |
| 9 | 16:88727163:G:A | | | | | | | | | 1 | 1.3E-8 | 3.1E-9 | 2.8E-5 |
| 10 | 16:88736324:G:A | | | | | | | | | | 1 | 2.1E-9 | 8.6E-5 |
| 11 | 16:88738735:D:1 | | | | | | | | | | | 1 | 8.1E-6 |
| 12 | 16:88835545:G:A | | | | | | | | | | | | 1 |

Figure 5

PIEZO TYPE MECHANOSENSITIVE ION CHANNEL COMPONENT 1 (PIEZO1) VARIANTS AND USES THEREOF

REFERENCE TO A SEQUENCE LISTING

This application includes a Sequence Listing submitted electronically as an XML file named 381203668SEQ, created on May 12, 2023, with a size of 93,082 bytes. The Sequence Listing is incorporated by reference herein.

FIELD

The present disclosure provides methods of treating patients having varicose veins, methods of identifying subjects having an increased risk of developing varicose veins, and methods of diagnosing varicose veins in a human subject, comprising detecting the presence of PIEZO1 predicted loss-of-function variant nucleic acid molecules and polypeptides in a biological sample from the patient or subject.

BACKGROUND

Varicose veins is a common multifactorial disease with largely unknown genetic drivers that is often seen in patients with chronic venous insufficiency, together classified as chronic venous disease. Dysfunction of venous valves is associated with varicose veins, venous hypertension, and thrombosis. Several processes, such as changes in hemodynamic forces, endothelial activation, inflammation, hypoxia, and dysregulation of matrix metalloproteinases and their tissue inhibitors have been associated with varicose vein development. Varicose vein risk factors include increased age, female sex, number of pregnancies, obesity, history of deep venous thrombosis, and standing occupation. Varicose veins has also been linked to insufficient lymph drainage and chronic venous insufficiency. In addition, several genome-wide association studies (GWAS) displayed about 18.5% varicose vein heritability.

PIEZO1 is encoded by a 70 kb gene located at 16q24.3 and is present in five potential isoforms. PIEZO1 protein is 2,521 amino acids long, and is a 286 kDa transmembrane protein that contains 38 transmembrane domains and functions as a homo-tetramer. PIEZO1 encodes an evolutionarily conserved endothelial mechanosensitive cation channel, which generates currents characterized by a linear current-voltage relationship that are sensitive to ruthenium red and gadolinium. PIEZO1 is ubiquitously expressed and plays a role in epithelial cell adhesion by maintaining integrin activation through R-Ras recruitment to the endoplasmic reticulum, most probably in its activated state, and subsequent stimulation of calpain signaling. In vasculature, PIEZO1 is involved in endothelial cell migration and sprouting angiogenesis. Specifically, PIEZO1 acts as a sensor for bloodflow-associated shear stress and promotes endothelial cell organization and alignment in the direction of blood flow ensuring proper vessel formation, remodeling, and maturation. PIEZO1 also appears to be required for lymphatic valve formation. Other reported functions include blood pressure regulation, urine osmolarity, erythrocyte integrity, pressure sensing, and collecting duct osmoregulation.

SUMMARY

The present disclosure provides methods of identifying a human subject having an increased risk of developing varicose veins, wherein the method comprises determining or having determined in a biological sample obtained from the subject the presence or absence of: a Piezo Type Mechanosensitive Ion Channel Component 1 (PIEZO1) predicted loss-of-function variant genomic nucleic acid molecule; a PIEZO1 predicted loss-of-function variant mRNA molecule; a PIEZO1 predicted loss-of-function variant cDNA molecule produced from the mRNA molecule; or a PIEZO1 predicted loss-of-function variant polypeptide; wherein: the absence of the PIEZO1 predicted loss-of-function variant genomic nucleic acid molecule, mRNA molecule, cDNA molecule, or polypeptide indicates that the subject does not have an increased risk for developing varicose veins; and the presence of the PIEZO1 predicted loss-of-function variant genomic nucleic acid molecule, mRNA molecule, cDNA molecule, or polypeptide indicates that the subject has an increased risk for developing varicose veins.

The present disclosure also provides methods of diagnosing varicose veins in a human subject, wherein the method comprises detecting in a sample obtained from the subject the presence or absence of: a Piezo Type Mechanosensitive Ion Channel Component 1 (PIEZO1) predicted loss-of-function variant genomic nucleic acid molecule; a PIEZO1 predicted loss-of-function variant mRNA molecule; a PIEZO1 predicted loss-of-function variant cDNA molecule produced from the mRNA molecule; or a PIEZO1 predicted loss-of-function variant polypeptide; wherein when the subject has a PIEZO1 predicted loss-of-function variant genomic nucleic acid molecule, mRNA molecule, cDNA molecule, or polypeptide, and has one or more symptoms of varicose veins, then the subject is diagnosed as having varicose veins.

The present disclosure also provides methods of treating a patient with a therapeutic agent that treats or inhibits varicose veins, wherein the patient is suffering from varicose veins or has an increased risk of developing varicose veins, the method comprising the steps of: determining whether the patient has a Piezo Type Mechanosensitive Ion Channel Component 1 (PIEZO1) predicted loss-of-function variant nucleic acid molecule encoding a human PIEZO1 polypeptide by: obtaining or having obtained a biological sample from the patient; and performing or having performed a genotyping assay on the biological sample to determine if the patient has a genotype comprising the PIEZO1 predicted loss-of-function variant nucleic acid molecule; and when the patient is PIEZO1 reference, then administering or continuing to administer to the patient the therapeutic agent that treats or inhibits the varicose veins in a standard dosage amount; and when the patient is heterozygous or homozygous for a PIEZO1 predicted loss-of-function variant nucleic acid molecule, then administering or continuing to administer to the patient the therapeutic agent that treats or inhibits the varicose veins in an amount that is the same as or greater than the standard dosage amount; wherein the presence of a genotype having the PIEZO1 predicted loss-of-function variant nucleic acid molecule encoding the human PIEZO1 polypeptide indicates the patient has an increased risk of developing varicose veins.

BRIEF DESCRIPTION OF THE FIGURES

The accompanying figures, which are incorporated in and constitute a part of this specification, illustrate several aspects and together with the description serve to explain the principles of the present disclosure.

FIG. 4 shows Single-point and aggregate results for the 65 pLOF variants in PIEZO1.

FIG. 5 shows LD Assessment for PIEZO1.

DESCRIPTION

Figure 1:
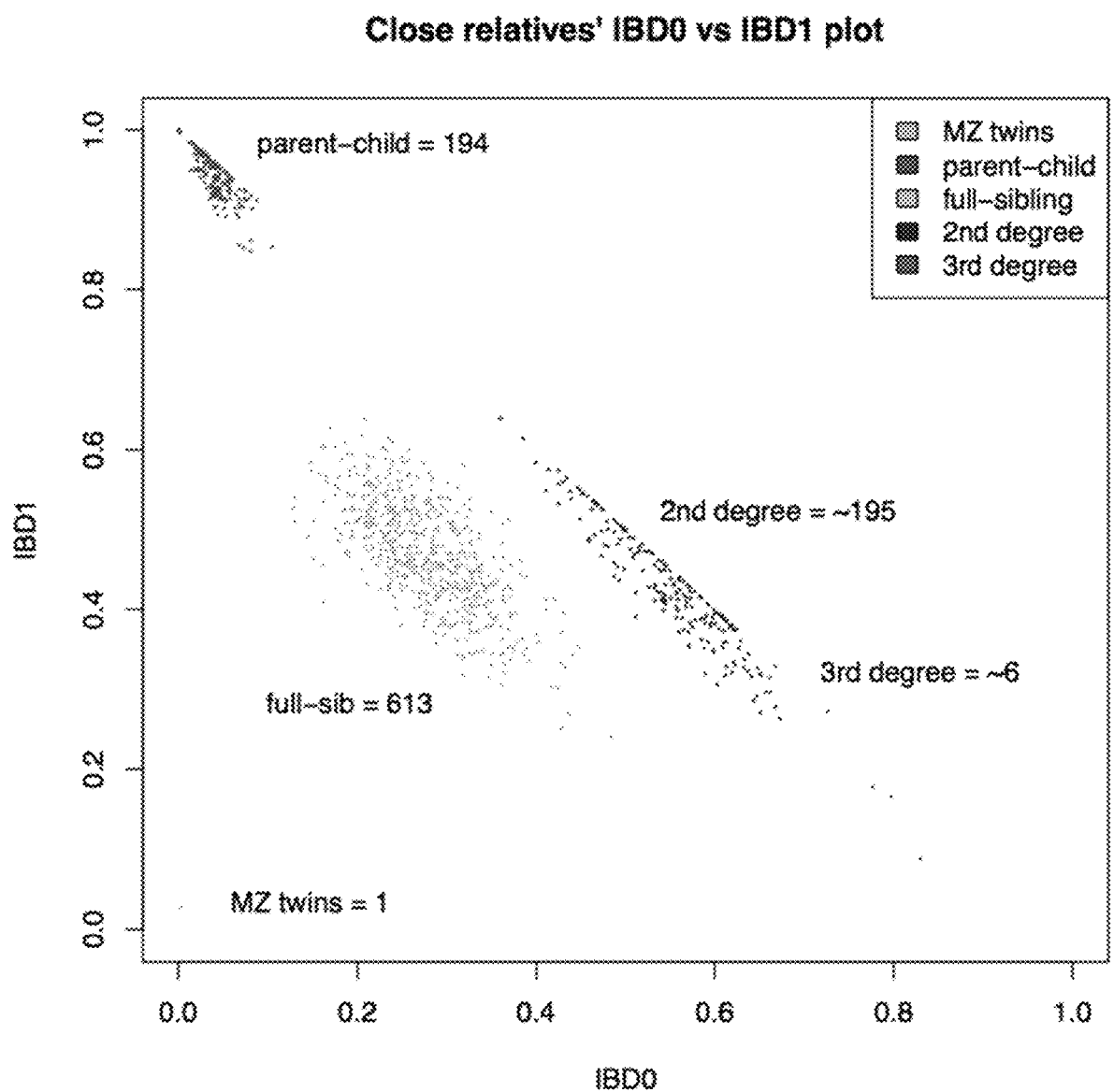
FIG. 1 shows a representative distribution of IBD sharing for pairs of individuals in UKB 50 k WES; estimated proportion of WES genotypes with no alleles identical by descent (IBD) vs. 1 allele IBD amongst all pairs of UKB 50 k exome participants.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human.

As used herein, a "nucleic acid," a "nucleic acid molecule," a "nucleic acid sequence," a "polynucleotide," or an "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "comprising" may be replaced with "consisting" or "consisting essentially of" in particular embodiments as desired.

As used herein, the phrase "corresponding to" or grammatical variations thereof when used in the context of the numbering of a particular amino acid or nucleotide sequence or position refers to the numbering of a specified reference sequence when the particular amino acid or nucleotide sequence is compared to the reference sequence (e.g., with the reference sequence herein being the nucleic acid molecule or polypeptide of (wild type) PIEZO1). In other words, the residue (e.g., amino acid or nucleotide) number or residue (e.g., amino acid or nucleotide) position of a particular polymer is designated with respect to the reference sequence rather than by the actual numerical position of the residue within the particular amino acid or nucleotide sequence. For example, a particular amino acid sequence can be aligned to a reference sequence by introducing gaps to optimize residue matches between the two sequences. In these cases, although the gaps are present, the numbering of the residue in the particular amino acid or nucleotide sequence is made with respect to the reference sequence to which it has been aligned.

It has been observed in accordance with the present disclosure that certain variations in PIEZO1 associate with a risk of developing varicose veins. It is believed that no variants of the PIEZO1 gene or protein have any known association with varicose veins in human beings. Therefore, human subjects having PIEZO1 alterations that associate with varicose veins may be treated such that varicose veins is inhibited, the symptoms thereof are reduced, and/or development of symptoms is repressed. Accordingly, the present disclosure provides methods for leveraging the identification of such variants in subjects to identify or stratify risk in such subjects of developing varicose veins, or to diagnose subjects as having varicose veins, such that subjects at risk or subjects with active disease may be treated.

For purposes of the present disclosure, any particular human can be categorized as having one of three PIEZO1 genotypes: i) PIEZO1 reference; ii) heterozygous for a PIEZO1 predicted loss-of-function variant, and iii) homozygous for a PIEZO1 predicted loss-of-function variant. A human is PIEZO1 reference when the human does not have a copy of a PIEZO1 predicted loss-of-function variant nucleic acid molecule. A human is heterozygous for a PIEZO1 predicted loss-of-function variant when the human has a single copy of a PIEZO1 predicted loss-of-function variant nucleic acid molecule. A PIEZO1 predicted loss-of-function variant nucleic acid molecule is any PIEZO1 nucleic acid molecule (such as, a genomic nucleic acid molecule, an mRNA molecule, or a cDNA molecule) encoding a PIEZO1 polypeptide having a partial loss-of-function, a complete loss-of-function, a predicted partial loss-of-function, or a predicted complete loss-of-function. A human who has a PIEZO1 polypeptide having a partial loss-of-function (or predicted partial loss-of-function) is hypomorphic for PIEZO1. The PIEZO1 predicted loss-of-function variant nucleic acid molecule can be any variant nucleic acid molecule described herein. A human is homozygous for a PIEZO1 predicted loss-of-function variant when the human has two copies of any of the PIEZO1 predicted loss-of-function variant nucleic acid molecules.

For human subjects or patients that are genotyped or determined to be heterozygous or homozygous for a PIEZO1 predicted loss-of-function variant nucleic acid molecule, such human subjects or patients have an increased risk of developing varicose veins. For human subjects or patients that are genotyped or determined to be heterozygous or homozygous for a PIEZO1 predicted loss-of-function variant nucleic acid molecule, such human subjects or patients can be treated with an agent effective to treat varicose veins.

The present disclosure provides methods of identifying a human subject having an increased risk of developing varicose veins, wherein the method comprises determining or having determined in a biological sample obtained from the subject the presence or absence of a PIEZO1 predicted loss-of-function variant nucleic acid molecule (such as a genomic nucleic acid molecule, mRNA molecule, and/or cDNA molecule) or polypeptide; wherein the absence of the PIEZO1 predicted loss-of-function variant nucleic acid molecule or polypeptide indicates that the subject does not have an increased risk for developing varicose veins; and the presence of the PIEZO1 predicted loss-of-function variant genomic nucleic acid molecule, mRNA molecule, cDNA molecule, or polypeptide indicates that the subject has an increased risk for developing varicose veins.

The present disclosure also provides methods of identifying a human subject having an increased risk of developing varicose veins, wherein the method comprises determining or having determined in a biological sample obtained from the subject the presence or absence of: i) a PIEZO1 predicted loss-of-function variant genomic nucleic acid molecule; ii) a PIEZO1 predicted loss-of-function variant mRNA molecule; iii) a PIEZO1 predicted loss-of-function variant cDNA molecule produced from the mRNA molecule; or iv) a PIEZO1 predicted loss-of-function variant polypeptide; wherein: the absence of the PIEZO1 predicted loss-of-function variant genomic nucleic acid molecule, mRNA molecule, cDNA molecule, or polypeptide indicates that the subject does not have an increased risk for developing varicose veins; and the presence of the PIEZO1 predicted loss-of-function variant genomic nucleic acid molecule, mRNA molecule, cDNA molecule, or polypeptide indicates that the subject has an increased risk for developing varicose veins.

The present disclosure also provides methods of identifying a human subject having an increased risk for developing varicose veins, wherein the method comprises: determining or having determined in a biological sample obtained from the subject the presence or absence of a PIEZO1 predicted loss-of-function variant nucleic acid molecule (such as a genomic nucleic acid molecule, mRNA molecule, and/or cDNA molecule) encoding a human PIEZO1 polypeptide; wherein: i) when the human subject lacks a PIEZO1 predicted loss-of-function variant nucleic acid molecule (i.e., the human subject is genotypically categorized as a PIEZO1 reference), then the human subject does not have an increased risk for developing varicose veins; and ii) when the human subject has a PIEZO1 predicted loss-of-function variant nucleic acid molecule (i.e., the human subject is categorized as heterozygous for a PIEZO1 predicted loss-of-function variant or homozygous for a PIEZO1 predicted loss-of-function variant), then the human subject has an increased risk for developing varicose veins.

In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

Determining whether a human subject has a PIEZO1 predicted loss-of-function variant nucleic acid molecule in a biological sample can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In any of the embodiments described herein, the varicose veins can be early stage varicose veins (e.g., C0 according to CEAP (Clinical, Etiological, Anatomical, and Pathophysiological) classification). In some embodiments, the varicose veins can be late stage varicose veins (e.g., C6 according to CEAP classification). In some embodiments, the varicose veins can be at any disease stage (e.g., C0-C6 according to CEAP classification). In some embodiments, the human subject is a female.

In some embodiments, when a human subject is identified as having an increased risk of developing varicose veins, the human subject is further treated with a therapeutic agent that treats or inhibits varicose veins, as described herein. For example, when the human subject is heterozygous or homozygous for a PIEZO1 predicted loss-of-function variant nucleic acid molecule, and therefore has an increased risk for developing varicose veins, the human subject is administered a therapeutic agent that treats or inhibits varicose veins. In some embodiments, when the patient is homozygous for a PIEZO1 predicted loss-of-function variant nucleic acid molecule, the patient is administered the therapeutic agent that treats or inhibits varicose veins in a dosage amount that is the same as or greater than the standard dosage amount administered to a patient who is heterozygous for a PIEZO1 predicted loss-of-function variant nucleic acid molecule. In some embodiments, the patient is heterozygous for a PIEZO1 predicted loss-of-function variant nucleic acid molecule. In some embodiments, the patient is homozygous for a PIEZO1 predicted loss-of-function variant nucleic acid molecule.

The present disclosure provides methods of diagnosing varicose veins in a human subject, wherein the methods comprise detecting in a sample obtained from the subject the presence or absence of a PIEZO1 predicted loss-of-function variant nucleic acid molecule (such as a genomic nucleic acid molecule, mRNA molecule, and/or cDNA molecule) or polypeptide; wherein when the subject has a PIEZO1 predicted loss-of-function variant genomic nucleic acid molecule, mRNA molecule, cDNA molecule, or polypeptide, and has one or more symptoms of varicose veins, then the subject is diagnosed as having varicose veins.

The present disclosure also provides methods of diagnosing varicose veins in a human subject, wherein the methods comprise detecting in a sample obtained from the subject the presence or absence of: i) a PIEZO1 predicted loss-of-function variant genomic nucleic acid molecule; ii) a PIEZO1 predicted loss-of-function variant mRNA molecule; iii) a PIEZO1 predicted loss-of-function variant cDNA molecule produced from the mRNA molecule; or iv) a PIEZO1 predicted loss-of-function variant polypeptide; wherein when the subject has a PIEZO1 predicted loss-of-function variant genomic nucleic acid molecule, mRNA molecule, cDNA molecule, or polypeptide, and has one or more symptoms of varicose veins, then the subject is diagnosed as having varicose veins.

The present disclosure also provides methods of diagnosing varicose veins in a human subject, wherein the methods comprise detecting in a sample obtained from the subject the presence or absence of a PIEZO1 predicted loss-of-function variant nucleic acid molecule (such as a genomic nucleic acid molecule, mRNA molecule, and/or cDNA molecule) encoding a human PIEZO1 polypeptide; wherein when the subject has a PIEZO1 predicted loss-of-function variant genomic nucleic acid molecule, mRNA molecule, cDNA molecule, or polypeptide (i.e., the human subject is categorized as heterozygous or homozygous for a PIEZO1 predicted loss-of-function variant nucleic acid molecule), and has one or more symptoms of varicose veins, then the subject is diagnosed as having varicose veins In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

Detecting the presence or absence of a PIEZO1 predicted loss-of-function variant nucleic acid molecule in a sample obtained from the subject can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In any of the embodiments described herein, the varicose veins can be early stage varicose veins (e.g., C0 according to CEAP (Clinical, Etiological, Anatomical, and Pathophysiological) classification). In some embodiments, the varicose veins can be late stage varicose veins (e.g., C6 according to CEAP classification). In some embodiments, the varicose veins can be at any disease stage (e.g., C0-C6 according to CEAP classification). In some embodiments, the human subject is a female.

In some embodiments, when a human subject is diagnosed as having varicose veins, the human subject is further treated with a therapeutic agent that treats or inhibits varicose veins, as described herein. For example, when the human subject is determined to be heterozygous or homozygous for a PIEZO1 predicted loss-of-function variant nucleic acid molecule, and has one or more symptoms of varicose veins, the human subject is administered a therapeutic agent that treats or inhibits varicose veins. In some embodiments, when the patient is homozygous for a PIEZO1 predicted loss-of-function variant nucleic acid molecule, the patient is administered the therapeutic agent that treats or inhibits varicose veins in a dosage amount that is the same as or greater than the standard dosage amount administered to a patient who is heterozygous for a PIEZO1 predicted loss-of-function variant nucleic acid molecule. In some embodiments, the patient is heterozygous for a PIEZO1 predicted loss-of-function variant nucleic acid molecule. In some embodiments, the patient is homozygous for a PIEZO1 predicted loss-of-function variant nucleic acid molecule.

The present disclosure also provides methods of treating a patient with a therapeutic agent that treats or inhibits varicose veins, wherein the patient is suffering from varicose veins or has an increased risk of developing varicose veins, the methods comprising the steps of: determining whether the patient has a PIEZO1 predicted loss-of-function variant nucleic acid molecule encoding a human PIEZO1 polypeptide by: obtaining or having obtained a biological sample from the patient; and performing or having performed a genotyping assay on the biological sample to determine if the patient has a genotype comprising the PIEZO1 predicted loss-of-function variant nucleic acid molecule; and when the patient is PIEZO1 reference, then administering or continuing to administer to the patient the therapeutic agent that treats or inhibits the varicose veins in a standard dosage amount; and when the patient is heterozygous or homozygous for a PIEZO1 predicted loss-of-function variant nucleic acid molecule, then administering or continuing to administer to the patient the therapeutic agent that treats or inhibits the varicose veins in an amount that is the same as or greater than the standard dosage amount; wherein the presence of a genotype having the PIEZO1 predicted loss-of-function variant nucleic acid molecule encoding the human PIEZO1 polypeptide indicates the patient has an increased risk of developing varicose veins. In some embodiments, the patient is heterozygous for a PIEZO1 predicted loss-of-function variant nucleic acid molecule. In some embodiments, the patient is homozygous for a PIEZO1 predicted loss-of-function variant nucleic acid molecule.

In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

The genotyping assay to determine whether a patient has a PIEZO1 predicted loss-of-function variant nucleic acid molecule encoding a human PIEZO1 polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the human subject.

In some embodiments, when the patient is homozygous for a PIEZO1 predicted loss-of-function variant nucleic acid molecule, the patient is administered the therapeutic agent that treats or inhibits varicose veins in a dosage amount that is the same as or greater than the standard dosage amount administered to a patient who is heterozygous for a PIEZO1 predicted loss-of-function variant nucleic acid molecule.

The present disclosure also provides methods of treating a patient with a therapeutic agent that treats or inhibits varicose veins, wherein the patient is suffering from varicose veins or has an increased risk of developing varicose veins, the methods comprising the steps of: determining whether the patient has a PIEZO1 predicted loss-of-function variant polypeptide by: obtaining or having obtained a biological sample from the patient; and performing or having performed an assay on the biological sample to determine if the patient has a PIEZO1 predicted loss-of-function variant polypeptide; and when the patient does not have a PIEZO1 predicted loss-of-function variant polypeptide, then administering or continuing to administer to the patient the therapeutic agent that treats or inhibits the varicose veins in a standard dosage amount; and when the patient has a PIEZO1 predicted loss-of-function variant polypeptide, then administering or continuing to administer to the patient the therapeutic agent that treats or inhibits the varicose veins in an amount that is the same as or greater than the standard dosage amount; wherein the presence of a PIEZO1 predicted loss-of-function variant polypeptide indicates the patient has an increased risk of developing varicose veins. In some embodiments, the patient has a PIEZO1 predicted loss-of-function variant polypeptide. In some embodiments, the patient does not have a PIEZO1 predicted loss-of-function variant polypeptide.

The assay to determine whether a patient has a PIEZO1 predicted loss-of-function variant polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell obtained from the human subject.

In any of the embodiments described herein, the PIEZO1 predicted loss-of-function variant polypeptide can be any PIEZO1 polypeptide having a partial loss-of-function, a complete loss-of-function, a predicted partial loss-of-function, or a predicted complete loss-of-function. For example, the PIEZO1 predicted loss-of-function variant polypeptide can be any of the PIEZO1 variant polypeptides described herein.

In any of the embodiments described herein, the varicose veins can be early stage varicose veins (e.g., C0 according to CEAP (Clinical, Etiological, Anatomical, and Pathophysiological) classification). In some embodiments, the varicose veins can be late stage varicose veins (e.g., C6 according to CEAP classification). In some embodiments, the varicose veins can be at any disease stage (e.g., C0-C6 according to CEAP classification). In some embodiments, the human subject is a female.

Symptoms of varicose veins include, but are not limited to, heavy legs, appearance of spider veins (telangiectasia) in the affected leg, ankle swelling, especially in the evening, brownish-yellow shiny skin discoloration near the affected veins, redness, dryness, and itchiness of areas of skin (termed stasis dermatitis or venous eczema), cramps especially developing when making a sudden move such as standing up, minor injuries to the affected area, bleeding more than normal or taking a long time to heal, shrinking of the skin above the ankle (lipodermatosclerosis), restless legs syndrome, whitened, irregular scar-like patches appearing at the ankles (atrophie blanche), or any combination thereof.

Examples of therapeutic agents that treat or inhibit varicose veins include, but are not limited to flavonoids, such as diosmin or hesperidin, and anti-inflammatory agents, such as ibuprofen and aspirin.

In some embodiments, the dose of the therapeutic agents that treat or inhibit varicose veins can be reduced by about 10%, by about 20%, by about 30%, by about 40%, by about 50%, by about 60%, by about 70%, by about 80%, or by about 90% for patients or human subjects that are heterozygous for a PIEZO1 predicted loss-of-function variant nucleic acid molecule (i.e., a lower than the standard dosage amount) compared to patients or human subjects that are homozygous for a PIEZO1 predicted loss-of-function variant nucleic acid molecule (who may receive a standard dosage amount). In some embodiments, the dose of the therapeutic agents that treat or inhibit varicose veins can be reduced by about 10%, by about 20%, by about 30%, by about 40%, or by about 50%. In addition, the dose of therapeutic agents that treat or inhibit varicose veins in patients or human subjects that are heterozygous for a PIEZO1 predicted loss-of-function variant nucleic acid molecule can be administered less frequently compared to patients or human subjects that are homozygous for a PIEZO1 predicted loss-of-function variant nucleic acid molecule.

Administration of the therapeutic agents that treat or inhibit varicose veins can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a patient can receive therapy for a prolonged period of time such as, for example, 6 months, 1 year, or more.

Administration of the therapeutic agents that treat or inhibit varicose veins can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in varicose veins, a decrease/reduction in the severity of varicose veins (such as, for example, a reduction or inhibition of development of varicose veins), a decrease/reduction in symptoms and varicose vein-related effects, delaying the onset of symptoms and varicose vein-related effects, reducing the severity of symptoms of varicose vein-related effects, reducing the severity of an acute episode, reducing the number of symptoms and varicose vein-related effects, reducing the latency of symptoms and varicose vein-related effects, an amelioration of symptoms and varicose vein-related effects, reducing secondary symptoms, reducing secondary infections, preventing relapse to varicose veins, decreasing the number or frequency of relapse episodes, increasing latency between symptomatic episodes, increasing time to sustained progression, speeding recovery, and/or increasing efficacy of or decreasing resistance to alternative therapeutics, following administration of the agent or composition comprising the agent. A prophylactic effect may comprise a complete or partial avoidance/inhibition or a delay of varicose vein development/progression (such as, for example, a complete or partial avoidance/inhibition or a delay) following administration of a therapeutic protocol. Treatment of varicose veins encompasses the treatment of patients already diagnosed as having any form of varicose veins at any clinical stage or manifestation, the delay of the onset or evolution or aggravation or deterioration of the symptoms or signs of varicose veins, and/or preventing and/or reducing the severity of varicose veins.

The present disclosure also provides, in any of the methods described herein, the detection or determination of the presence of a PIEZO1 predicted loss-of-function variant genomic nucleic acid molecule, a PIEZO1 predicted loss-of-function variant mRNA molecule, and/or a PIEZO1 predicted loss-of-function variant cDNA molecule in a biological sample from a subject human. It is understood that gene sequences within a population and mRNA molecules encoded by such genes can vary due to polymorphisms such as single-nucleotide polymorphisms. The sequences provided herein for the PIEZO1 variant nucleic acid molecules disclosed herein are only exemplary sequences. Other sequences for the PIEZO1 variant nucleic acid molecules are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any PIEZO1 variant nucleic acid molecule, preliminary processing designed to isolate or enrich the sample for the genomic DNA can be employed. A variety of known techniques may be used for this purpose. When detecting the level of any PIEZO1 variant mRNA, different techniques can be used enrich the biological sample with mRNA. Various methods to detect the presence or level of a mRNA or the presence of a particular variant genomic DNA locus can be used.

In some embodiments, detecting a human PIEZO1 predicted loss-of-function variant nucleic acid molecule in a human subject comprises assaying or genotyping a biological sample obtained from the human subject to determine whether a PIEZO1 genomic nucleic acid molecule, a PIEZO1 mRNA molecule, or a PIEZO1 cDNA molecule produced from an mRNA molecule in the biological sample comprises one or more variations that cause a loss-of-function (partial or complete) or are predicted to cause a loss-of-function (partial or complete).

In some embodiments, the methods of detecting the presence or absence of a PIEZO1 predicted loss-of-function variant nucleic acid molecule (such as, for example, a genomic nucleic acid molecule, an mRNA molecule, and/or a cDNA molecule) in a human subject, comprise: performing an assay on a biological sample obtained from the human subject, which assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising a PIEZO1 genomic nucleic acid molecule or mRNA molecule, and if mRNA, optionally reverse transcribing the mRNA into cDNA. Such assays can comprise, for example determining the identity of these positions of the particular PIEZO1 nucleic acid molecule. In some embodiments, the method is an in vitro method.

In some embodiments, the determining step, detecting step, or genotyping assay comprises sequencing at least a portion of the nucleotide sequence of the PIEZO1 genomic nucleic acid molecule, the PIEZO1 mRNA molecule, or the PIEZO1 cDNA molecule produced from the mRNA molecule in the biological sample, wherein the sequenced portion comprises one or more variations that cause a loss-of-function (partial or complete) or are predicted to cause a loss-of-function (partial or complete).

In any of the methods described herein, the determining step, detecting step, or genotyping assay comprises sequencing at least a portion of the nucleotide sequence of the PIEZO1 nucleic acid molecule in the biological sample, wherein the sequenced portion comprises a position corresponding to a predicted loss-of-function variant position, wherein when a variant nucleotide at the predicted loss-of-function variant position is detected, the PIEZO1 nucleic acid molecule in the biological sample is a PIEZO1 predicted loss-of-function variant nucleic acid molecule.

In some embodiments, the determining step, detecting step, or genotyping assay comprises: a) contacting the biological sample with a primer hybridizing to a portion of the nucleotide sequence of the PIEZO1 nucleic acid molecule that is proximate to a predicted loss-of-function variant position; b) extending the primer at least through the predicted loss-of-function variant position; and c) determining whether the extension product of the primer comprises a variant nucleotide at the predicted loss-of-function variant position.

In some embodiments, the assay comprises sequencing the entire nucleic acid molecule. In some embodiments, only a PIEZO1 genomic nucleic acid molecule is analyzed. In some embodiments, only a PIEZO1 mRNA is analyzed. In some embodiments, only a PIEZO1 cDNA obtained from PIEZO1 mRNA is analyzed.

In some embodiments, the determining step, detecting step, or genotyping assay comprises: a) amplifying at least a portion of the PIEZO1 nucleic acid molecule that encodes the human PIEZO1 polypeptide, wherein the portion comprises a predicted loss-of-function variant position; b) labeling the amplified nucleic acid molecule with a detectable label; c) contacting the labeled nucleic acid molecule with a support comprising an alteration-specific probe, wherein the alteration-specific probe comprises a nucleotide sequence which hybridizes under stringent conditions to the predicted loss-of-function variant position; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to a predicted loss-of-function variant position; and detecting the detectable label.

The alteration-specific probes or alteration-specific primers described herein comprise a nucleic acid sequence which is complementary to and/or hybridizes, or specifically hybridizes, to a PIEZO1 predicted loss-of-function variant nucleic acid molecule, or the complement thereof. In some embodiments, the alteration-specific probes or alteration-specific primers comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, or at least about 50 nucleotides. In some embodiments, the alteration-specific probes or alteration-specific primers comprise or consist of at least 15 nucleotides. In some embodiments, the alteration-specific probes or alteration-specific primers comprise or consist of at least 15 nucleotides to at least about 35 nucleotides. In some embodiments, alteration-specific probes or alteration-specific primers hybridize to PIEZO1 predicted loss-of-function variant genomic nucleic acid molecules, PIEZO1 predicted loss-offunction variant mRNA molecules, and/or PIEZO1 predicted loss-of-function variant cDNA molecules under stringent conditions.

Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the human subject.

In any of the embodiments described herein, the PIEZO1 predicted loss-of-function variant nucleic acid molecule can be any PIEZO1 nucleic acid molecule (such as, for example, genomic nucleic acid molecule, mRNA molecule, or cDNA molecule) encoding a PIEZO1 polypeptide having a partial loss-of-function, a complete loss-of-function, a predicted partial loss-of-function, or a predicted complete loss-of-function. For example, the PIEZO1 predicted loss-of-function variant nucleic acid molecule can be any of the PIEZO1 variant nucleic acid molecules described herein.

In some embodiments, the assay comprises contacting the biological sample with a primer or probe, such as an alteration-specific primer or alteration-specific probe, that specifically hybridizes to a PIEZO1 variant genomic sequence, variant mRNA sequence, or variant cDNA sequence and not the corresponding PIEZO1 reference sequence under stringent conditions, and determining whether hybridization has occurred.

In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising a PIEZO1 variant genomic nucleic acid molecule, variant mRNA molecule, or variant cDNA molecule. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. Stringent conditions are sequence-dependent and will be different in different circumstances.

Appropriate stringency conditions which promote DNA hybridization, for example, 6×sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M $Na^+$ ion, typically about 0.01 to 1.0 M $Na^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides molecular complexes comprising any of the PIEZO1 nucleic acid molecules (genomic nucleic acid molecules, mRNA molecules, or cDNA molecules), or complement thereof, described herein and any of the alteration-specific primers or alteration-specific probes described herein. In some embodiments, the PIEZO1 nucleic acid molecules (genomic nucleic acid molecules, mRNA molecules, or cDNA molecules), or complement thereof, in the molecular complexes are single-stranded. In some embodiments, the PIEZO1 nucleic acid molecule is any of the genomic nucleic acid molecules described herein. In some embodiments, the PIEZO1 nucleic acid molecule is any of the mRNA molecules described herein. In some embodiments, the PIEZO1 nucleic acid molecule is any of the cDNA molecules described herein. In some embodiments, the molecular complex comprises any of the PIEZO1 nucleic acid molecules (genomic nucleic acid molecules, mRNA molecules, or cDNA molecules), or complement thereof, described herein and any of the alteration-specific primers described herein. In some embodiments, the molecular complex comprises any of the PIEZO1 nucleic acid molecules (genomic nucleic acid molecules, mRNA molecules, or cDNA molecules), or complement thereof, described herein and any of the alteration-specific probes described herein. In some embodiments, the molecular complex comprises a non-human polymerase.

In some embodiments, detecting the presence of a human PIEZO1 predicted loss-of-function polypeptide comprises performing an assay on a sample obtained from a human subject to determine whether a PIEZO1 polypeptide in the subject contains one or more variations that causes the polypeptide to have a loss-of-function (partial or complete) or predicted loss-of-function (partial or complete). In some embodiments, the assay comprises sequencing at least a portion of the PIEZO1 polypeptide that comprises a variant position. In some embodiments, the detecting step comprises sequencing the entire polypeptide. Identification of a variant amino acid at the variant position of the PIEZO1 polypeptide indicates that the PIEZO1 polypeptide is a PIEZO1 predicted loss-of-function polypeptide. In some embodiments, the assay comprises an immunoassay for detecting the presence of a polypeptide that comprises a variant. Detection of a variant amino acid at the variant position of the PIEZO1 polypeptide indicates that the PIEZO1 polypeptide is a PIEZO1 predicted loss-of-function polypeptide.

The probes and/or primers (including alteration-specific probes and alteration-specific primers) described herein comprise or consist of from about 15 to about 100, from about 15 to about 35 nucleotides. In some embodiments, the alteration-specific probes and alteration-specific primers comprise DNA. In some embodiments, the alteration-specific probes and alteration-specific primers comprise RNA. In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers (including alteration-specific probes and alteration-specific primers) specifically hybridize to any of the nucleic acid molecules disclosed herein under stringent conditions. In the context of the disclosure "specifically hybridizes" means that the probe or primer (including alteration-specific probes and alteration-specific primers) does not hybridize to a nucleic acid sequence encoding a PIEZO1 reference genomic nucleic acid molecule, a PIEZO1 reference mRNA molecule, and/or a PIEZO1 reference cDNA molecule. In some embodiments, the probes (such as, for example, an alteration-specific probe) comprise a label. In some embodiments, the label is a fluorescent label, a radiolabel, or biotin.

The nucleotide sequence of a PIEZO1 reference genomic nucleic acid molecule is set forth in SEQ ID NO:1, which is 69,883 nucleotides in length. The first nucleotide recited in SEQ ID NO:1 corresponds to the nucleotide at position 88,715,338 of chromosome 16 (see, hg38_knownGene_ENST00000301015.14).

Numerous variant genomic nucleic acid molecule of PIEZO1 exist, including, but not limited to (using the human genome reference build GRch38): 16:88715629:G:A, 16:88715728:G:T, 16:88715767:G:A, 16:88715802:C:A, 16:88715822:D:4, 16:88715987:I:1, 16:88716359:A:G, 16:88716570:C:T, 16:88716874:G:A, 16:88717213:T:A, 16:88719588:G:A, 16:88719722:C:G, 16:88719870:G:T, 16:88720068:D:2, 16:88720229:C:A, 16:88720248:D:4, 16:88720394:C:T, 16:88720644:D:1, 16:88720698:D:1, 16:88720698:I:1, 16:88721165:C:A, 16:88721268:D:1, 16:88721307:G:A, 16:88721586:G:C, 16:88721652:G:C, 16:88722217:C:T, 16:88722605:I:1, 16:88723005:I:7, 16:88723253:G:A, 16:88723311:C:T, 16:88725081:C:A, 16:88726282:G:A, 16:88726546:C:T, 16:88726619:G:A, 16:88726924:G:A, 16:88727038:C:T, 16:88727072:D:1, 16:88727163:G:A, 16:88731768:D:1, 16:88732334:C:G, 16:88732411:D:1, 16:88732720:D:1, 16:88733326:G:C, 16:88733337:D:4, 16:88733587:C:A, 16:88733965:D:1, 16:88734017:C:A, 16:88734042:I:1, 16:88734679:C:T, 16:88734909:I:1, 16:88736167:D:2, 16:88736324:G:A, 16:88736391:G:T, 16:88736409:C:T, 16:88736671:G:A, 16:88737557:A:C, 16:88737727:C:G, 16:88737815:C:T, 16:88738283:G:C, 16:88738637:G:A, 16:88738735:D:1, 16:88741477:C:T, 16:88742306:D:1, 16:88749399:G:A, and 16:88784929:C:T. Thus, for example, using the SEQ ID NO:1 reference genomic nucleotide sequence as a base (with the first nucleotide listed therein designated as position 88,715,338), the first listed variant (16:88715629:G:A) would have a guanine replaced with an adenine (designated the "variant nucleotide") at position 88,715,629 (designated the "variant position"). Those variants designated as a "D" followed by a number have a deletion of the stated number of nucleotides. Those variants designated as an "I" followed by a number have an insertion of the stated number of nucleotides (any nucleotide). Any of these PIEZO1 predicted loss-of-function variant genomic nucleic acid molecules can be detected in any of the methods described herein.

The nucleotide sequence of a PIEZO1 reference mRNA molecule is set forth in SEQ ID NO:2 (see, NCBI Reference Sequence: NM_001142864.4), which is 8,089 nucleotides in length. The variant nucleotides at their respective variant positions for the variant genomic nucleic acid molecules described herein also have corresponding variant nucleotides at their respective variant positions for the variant mRNA molecules based upon the PIEZO1 reference mRNA sequence according to SEQ ID NO:2. Any of these PIEZO1 predicted loss-of-function variant mRNA molecules can be detected in any of the methods described herein.

The nucleotide sequence of a PIEZO1 reference cDNA molecule is set forth in SEQ ID NO:3 (based upon NCBI Reference Sequence: NM_001142864.4), which is 8,089 nucleotides in length. The variant nucleotides at their respective variant positions for the variant genomic nucleic acid molecules described herein also have corresponding variant nucleotides at their respective variant positions for the variant cDNA molecules based upon the PIEZO1 reference cDNA sequence according to SEQ ID NO:3. Any of these PIEZO1 predicted loss-of-function variant cDNA molecules can be detected in any of the methods described herein.

The amino acid sequence of a PIEZO1 reference polypeptide is set forth in SEQ ID NO:4 (see, UniProt Accession No. Q92508.4 and NCBI RefSeq accession No. NM_001142864.4), which is 2,521 amino acids in length. Using the translated nucleotide sequence of either the PIEZO1 mRNA or cDNA molecules, the PIEZO1 variant polypeptides having corresponding translated variant amino acids at variant positions (codons). Any of these PIEZO1 predicted loss-of-function variant polypeptides can be detected in any of the methods described herein.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequence follows the standard convention of beginning at the amino terminus of the sequence and proceeding forward (i.e., from left to right in each line) to the carboxy terminus.

As used herein, the phrase "corresponding to" or grammatical variations thereof when used in the context of the numbering of a particular nucleotide or nucleotide sequence or position refers to the numbering of a specified reference sequence when the particular nucleotide or nucleotide sequence is compared to a reference sequence. In other words, the residue (such as, for example, nucleotide or amino acid) number or residue (such as, for example, nucleotide or amino acid) position of a particular polymer is designated with respect to the reference sequence rather than by the actual numerical position of the residue within the particular nucleotide or nucleotide sequence. For example, a particular nucleotide sequence can be aligned to a reference sequence by introducing gaps to optimize residue matches between the two sequences. In these cases, although the gaps are present, the numbering of the residue in the particular nucleotide or nucleotide 5 sequence is made with respect to the reference sequence to which it has been aligned. A variety of computational algorithms exist that can be used for performing a sequence alignment to identify a nucleotide or amino acid position in one polymeric molecule that corresponds to a nucleotide or amino acid position in another polymeric molecule. For example, by using the NCBI BLAST algorithm (Altschul et al., Nucleic Acids Res., 1997, 25, 3389-3402) or CLUSTALW software (Sievers and Higgins, Methods Mol. Biol., 2014, 1079, 105-116) sequence alignments may be performed. However, sequences can also be aligned manually.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Example 1: Materials and Methods

WES Sample Preparation and Sequencing

Genomic DNA samples normalized to approximately 16 ng/μl were transferred in house from the UK Biobank in 0.5 ml 2D matrix tubes (Thermo Fisher Scientific) and stored in an automated sample biobank (LiCONiC Instruments) at −80° C. prior to sample preparation. One sample had insufficient DNA for sequencing. Exome capture was completed using a high-throughput, fully-automated approach developed in house. Briefly, DNA libraries were created by enzymatically shearing 100 ng of genomic DNA to a mean fragment size of 200 base pairs using a custom NEBNext Ultra II FS DNA library prep kit (New England Biolabs) and a common Y-shaped adapter (Integrated DNA Technologies) was ligated to all DNA libraries. Unique, asymmetric 10 base pair barcodes were added to the DNA fragment during library amplification with KAPA HiFi polymerase (KAPA Biosystems) to facilitate multiplexed exome capture and sequencing. Equal amounts of sample were pooled prior to overnight exome capture, approximately 16 hours, with a slightly modified version of IDT's xGen probe library; supplemental probes were added to capture regions of the genome well-covered by a previous capture reagent (NimbleGen VCRome) but poorly covered by the standard xGen probes. In total, n=38,997,831 bases were included in the targeted regions. Captured fragments were bound to streptavidin-coupled DYNABEADS® (Thermo Fisher Scientific) and non-specific DNA fragments removed through a series of stringent washes using the xGen Hybridization and Wash kit according to the manufacturer's recommended protocol (Integrated DNA Technologies). The captured DNA was PCR amplified with KAPA HiFi and quantified by qPCR with a KAPA Library Quantification Kit (KAPA Biosystems). The multiplexed samples were pooled and then sequenced using 75 base pair paired-end reads with two 10 base pair index reads on the Illumina NOVASEQ® 6000 platform using S2 flow cells.

Sequence Alignment, Variant Identification, and Genotype Assignment

Upon completion of sequencing, raw data from each Illumina NOVASEQ® run was gathered in local buffer storage and uploaded to the DNAnexus platform for automated analysis. After upload was complete, analysis began with the conversion of CBCL files to FASTQ-formatted reads and assigned, via specific barcodes, to samples using the bcl2fastq conversion software (Illumina Inc., San Diego, CA). Sample-specific FASTQ files, representing all the reads generated for that sample, were then aligned to the GRCh38 genome reference with BWA-mem. The resultant binary alignment file (BAM) for each sample contained the mapped reads' genomic coordinates, quality information, and the degree to which a particular read differed from the reference at its mapped location. Aligned reads in the BAM file were then evaluated to identify and flag duplicate reads with the Picard MarkDuplicates tool (world wide web at "picard.sourceforge.net"), producing an alignment file (duplicatesMarked.BAM) with all potential duplicate reads marked for exclusion in downstream analyses.

GVCF files, including variant calls, were then produced on each individual sample using the WeCall variant caller (world wide web at "github.com/Genomicsplc/wecall") from Genomics PLC, identifying both SNVs and INDELs as compared to the reference. Additionally, each GVCF file carried the zygosity of each variant, read counts of both reference and alternate alleles, genotype quality representing the confidence of the genotype call, and the overall quality of the variant call at that position.

Upon completion of variant calling, individual sample BAM files were converted to fully lossless CRAM files using samtools. Metric statistics were captured for each sample to evaluate capture, alignment, insert size, and variant calling quality, using Picard (world wide web at "picard.sourceforge.net"), bcftools (world wide web at "samtools.github.io/bcftools"), and FastQC (world wide web at "bioinformatics.babraham.ac.uk/projects/fastqc").

Following completion of sample sequencing, samples showing disagreement between genetically-determined and reported sex (n=15), high rates of heterozygosity/contamination (D-stat>0.4) (n=7), low sequence coverage (less than 85% of targeted bases achieving 20×coverage) (n=1), or genetically-identified sample duplicates (n=14), and WES variants discordant with genotyping chip (n=9) were excluded. Six samples failed quality control in multiple categories, resulting in 38 individuals being excluded. The remaining 49,960 samples were then used to compile a project-level VCF (PVCF) for downstream analysis. The PVCF was created using the GLnexus joint genotyping tool. Care was taken to carry all homozygous reference, heterozygous, homozygous alternate, and no-call genotypes into the project-level VCF. An additional filtered PVCF, 'Goldilocks', was also generated. In the filtered Goldilocks PVCF, samples carrying SNP variant calls in the single sample pipeline or a DP<7 were converted to 'No-Call'. After the application of the DP filter, sites where all remaining samples were called as Heterozygous and all samples have an AB<85% ref/15% alt were excluded. Samples carrying INDEL variant calls in the single sample pipeline with a DP<10 were converted to 'No-Call'. After the application of the DP filter, sites where all remaining samples were called as Heterozygous and all samples have an AB<80% ref/20% alt were excluded. Multi-allelic variant sites in the PVCF file were normalized by left-alignment and represented as bi-allelic.

Phenotype Definition

ICD10-based cases required one or more of the following: a primary diagnosis or a secondary diagnosis in in-patient Health Episode Statistics (HES) records. ICD10-based excludes had ≥1 primary or secondary diagnosis in the code range. ICD10-based controls were defined as those individuals that were not cases or excludes. Custom phenotype definitions included one or more of the following: ICD-10 diagnosis, self-reported illness from verbal interview and doctor-diagnosed illness from online-follow-up, touch-screen information. Quantitative traits (such as, physical measures, blood counts, cognitive function tests, and imaging derived phenotypes) were downloaded from UK Biobank (UKB) repository and spanned one or more visits. In total, 1,073 binary traits with case count 50 and 669 number of quantitative traits, were tested in WES association analyses.

Annotation of Predicted Loss-Of-Function (LOF) Variants

Variants were annotated using snpEff and gene models from Ensembl Release 85. A comprehensive and high quality transcript set was obtained for protein coding regions which included all protein coding transcripts with an annotated Start and Stop codon from the Ensembl gene models. Variants annotated as stop_gained, start_lost, splice_donor, splice_acceptor, stop_lost and frameshift are considered to be LOF variants.

A recent large-scale study of genetic variation in 141,456 individuals provides a catalog of LOF variants. A direct comparison to this data is difficult due to numerous factors such as differences in exome sequencing capture platforms, variant calling algorithms and annotation. Additionally, the number of individuals and the geographic distribution of ascertainment (and thus genetic diversity) in the NFE subset of gnomAD may be larger than that of UK Biobank with WES in this report. Nonetheless, the gnomAD exome sites labeled as "PASS" from gnomAD r2.1 were annotated using the annotation pipeline. Data from gnomAD were lifted over to HG38 using Picard LiftoverVcf. The data was subset to Non-Finnish Europeans (NFE) (n=56,885 samples), individuals) restricted to variants with $MAF_{NFE}<1\%$ and obtained 261,309 LOFs in any transcript in 17,951 genes. Restricting LOFs only to those that are present in all transcripts, 175,162 LOFs were observed in 16,462 genes. 134,745 LOFs were observed in all transcripts of genes in UKB participants with WES of European ancestry.

Methods for LOF Burden Association Analysis

Burden tests of association were performed for rare LOFs within 49,960 individuals of European ancestry. For each gene region as defined by Ensembl. LOFs with MAF≤0.01 were collapsed such that any individual that is heterozygous for at least one LOF in that gene region is considered heterozygous, and only individuals that carry two copies of the same LOF are considered homozygous. Rare variants were not phased, and so compound heterozygotes are not considered in this analysis.

For each gene region, 668 rank-based inverse normal transformed (RINT) quantitative measures (including all subjects and sex-stratified models) with ≥5 individuals with non-missing phenotype information were assessed using an additive mixed model implemented in BOLT-LMM v2. Prior to normalization, traits were first transformed as appropriate (log 10, square) and adjusted for a standard set of covariates including age, sex, study site, first four principal components of ancestry, and in some cases BMI and/or smoking status. Data-points greater than five median absolute deviations from the median were excluded as outliers prior to normalization. 1,073 discrete outcomes (including all subjects and sex-stratified models) with ≥50 cases were assessed with covariate adjustment for age, sex and first four principle components of ancestry using a generalized mixed model implemented in SAIGE. For each quantitative and discrete trait included in the analysis, only gene regions in which >3 LOF carriers with non-missing phenotype and covariate information were evaluated.

Positive controls were systematically defined using a two-step approach. First, each gene for relevant disease, trait, biological, or functional evidence was annotated using publicly available resources including OMIM, NCBI MedGen, and the NHGRI-EBI GWAS catalogue. Genes with supporting evidence from at least one source, were then manually curated using NCBI PubMed to verify the relationship between the trait and LOF variants in the gene of interest. Genes with locus-level support for the trait of interest or related phenotype(s) in the GWAS catalog but lacking clear supporting evidence for a LOF association are reported herein as novel LOF associations.

Methods for Single Variant LOF Association Analysis

Single variant association analysis was performed using the same methods as described in the methods section for burden association analysis. For gene-trait associations with $p<10^{-7}$, single variant association statistics was calculated with the phenotype of interest for all LOFs included in the burden test that are observed with a minor allele count ≥5 in the 49,960 European ancestry individuals with WES. Association statistics for these variants are reported in Extended Data (ExtData_SingleVariantLOFs_V1.xlsx).

P-VAL Leave-One-Out (LOO) Burden is the p-value of the absence/presence test excluding the variant being tested. Delta P-Val Burden is the ratio of the p-value in the drop-one-out analysis compared to the burden test using all 65 variants. Burden summary statistics using all 65 variants in unrelated individuals: B=1.44, SE=0.26, p-value=3.12E-08, cMAF=0.00174, cMAC=152, cMAF_cases=0.0066, cMAC_cases=17, cMAF_controls=0.0016, cMAC_cases=135. Stepwise logistic regression selected 11/65 variants (AIC 11451). Burden summary statistics using the 11 variants: B=3.71, SE=0.437, p-value<2e-16, cMAF=0.0003, cMAC=22, cMAF_cases=0.005, cMAC_cases=12, cMAF_controls=0.0001, cMAC_controls=10. When analysis is restricted to variants with MAC>1, stepwise logistic regression selects 5/13 variants (AIC 11484). Burden summary statistics using the 5 variants: B=3.02, SE=0.53, p-value=8.92e-09.

LD (r2) across the 11 pLOF variants selected by stepwise regression for PIEZO1 and a positive control (16: 88835545_G_A; highlighted in green) reported in the literature for PIEZO1. None of these 12 variants are in LD, R2>0.01. When the burden test is adjusted for the previously reported variant rs2911463 (16:88835545_G_A), the burden test p-value remains <2E-16 (AIC 11,444), which indicates that the burden is not tagging the reported variant.

Example 2: Demographics and Clinical Characteristics of Sequenced Participants

A total of 50,000 participants were selected, prioritizing individuals with more complete phenotype data: those with whole body MRI imaging data from the UK Biobank Imaging Study, enhanced baseline measurements, hospital episode statistics (HES), and/or linked primary care records (which will soon be available to approved researchers). During data generation, samples from 40 participants were excluded due to failed quality control measures or participant withdrawal, resulting in a final set of 49,960 individuals. Overall, the sequenced sample is representative of the 500,000 UKB participants (Table 1). There were no notable differences in age, sex, or ancestry between the sequenced sample and overall study population. Sequenced participants were more likely to have HES diagnosis codes (84.2% among sequenced vs. 77.3% overall) and enhanced measures (Table 1).

TABLE 1

Clinical characteristics in whole exome sequenced and all UK Biobank participants

| Basic Demographics and Clinical Characteristics | UKB 50k WES Participants | UKB 500k Participants |
| --- | --- | --- |
| N | 49,960 | 502,543 |
| Female, n(%) | 27,243 (54) | 273,460 (54) |
| Age at assessment, years | 58 (45-71) | 58 (45-71) |
| Body mass index, kg/m$^2$ | 26 (21-31) | 26 (21-31) |
| Number of imaged participants | 12,075[b] | 21,407[a] |
| Number of current/past smokers, n(%) | 17,515 (35) | 216,482 (43) |
| Townsend Deprivation Index | −2.0 (−6.1, −2.1) | −2.13 (−6.2, −1.97) |
| Inpatient ICD10 codes per patient | 5 | 5 |
| Patients with >=1 ICD10 diagnoses (%) | 84.2 | 78.0 |
| Genetic Ancestry Assignment[c] | | |
| African (%) | 1.49 | 1.24 |
| East Asian (%) | 0.54 | 0.51 |
| European (%) | 93.66 | 94.55 |
| Cardiometabolic phenotypes | | |
| Coronary Disease, n(%) | 3,3340 (6.6) | 35,879 (7.1) |
| Heart Failure, n(%) | 300 (0.6) | 4,399 (0.8) |
| Type 2 Diabetes, n(%) | 1,541 (3.0) | 17,261 (3.4) |
| Respiratory and immunological phenotypes | | |
| Asthma, n(%) | 8,250 (16) | 68,149 (13) |
| COPD, n(%) | 741 (1.4) | 7,438 (1.4) |
| Rheumatoid Arthritis, n(%) | 710 (1.4) | 7,337 (1.4) |
| Inflammatory Bowel Disease n(%) | 543 (1.0) | 5,783 (1.1) |
| Neurodegenerative phenotypes | | |
| Alzheimer's Disease, n(%) | 13 (0.05) | 320 (0.06) |
| Parkinson's Disease, n(%) | 65 (0.13) | 1,043 (0.2) |
| Multiple Sclerosis, n(%) | 126 (0.25) | 1,352 (0.26) |
| Myasthenia Gravis, n(%) | 14 (0.02) | 217 (0.04) |
| Oncology phenotypes | | |
| Breast Cancer, n(%) | 1,667 (3.3) | 16,887 (3.3) |
| Ovarian Cancer, n(%) | 162 (0.3) | 1,777 (0.3) |
| Pancreatic Cancer, n(%) | 602 (1.2) | 4,611 (0.9) |
| Prostate Cancer, n(%) | 848 (1.6) | 8,855 (1.7) |
| Melanoma, n(%) | 598 (1.1) | 5,715 (1.1) |

TABLE 1-continued

Clinical characteristics in whole exome sequenced and all UK Biobank participants

| Basic Demographics and Clinical Characteristics | UKB 50k WES Participants | UKB 500k Participants |
|---|---|---|
| Enhanced measures | | |
| Hearing test available, n(%) | 40,546 (81.1) | 167,011 (33.2) |
| Pulse Rate, n(%) | 40,548 (34.2) | 170,761 (33.9) |
| Visual Acuity Measured, n(%) | 39,461 (78.9) | 117,092 (23.2) |
| IOP measured (left), n(%) | 37,940 (75.9) | 111,942 (22.2) |
| Autorefraction, n(%) | 36,067 (72.1) | 105,989 (21.0) |
| Retinal OCT, n(%) | 32,748 (65.5) | 67,708 (13.4) |
| ECG at rest, n(%) | 10,829 (27.1) | 13,572 (2.1) |
| Cognitive Function, n(%) | 9,511 (19.0) | 96,362 (19.1) |
| Digestive Health, n(%) | 13,553 (28.1) | 142,310 (28.3) |
| Physical Activity Measurement, n(%) | 10,684 (21.3) | 101,117 (20.1) |

Figure 3:
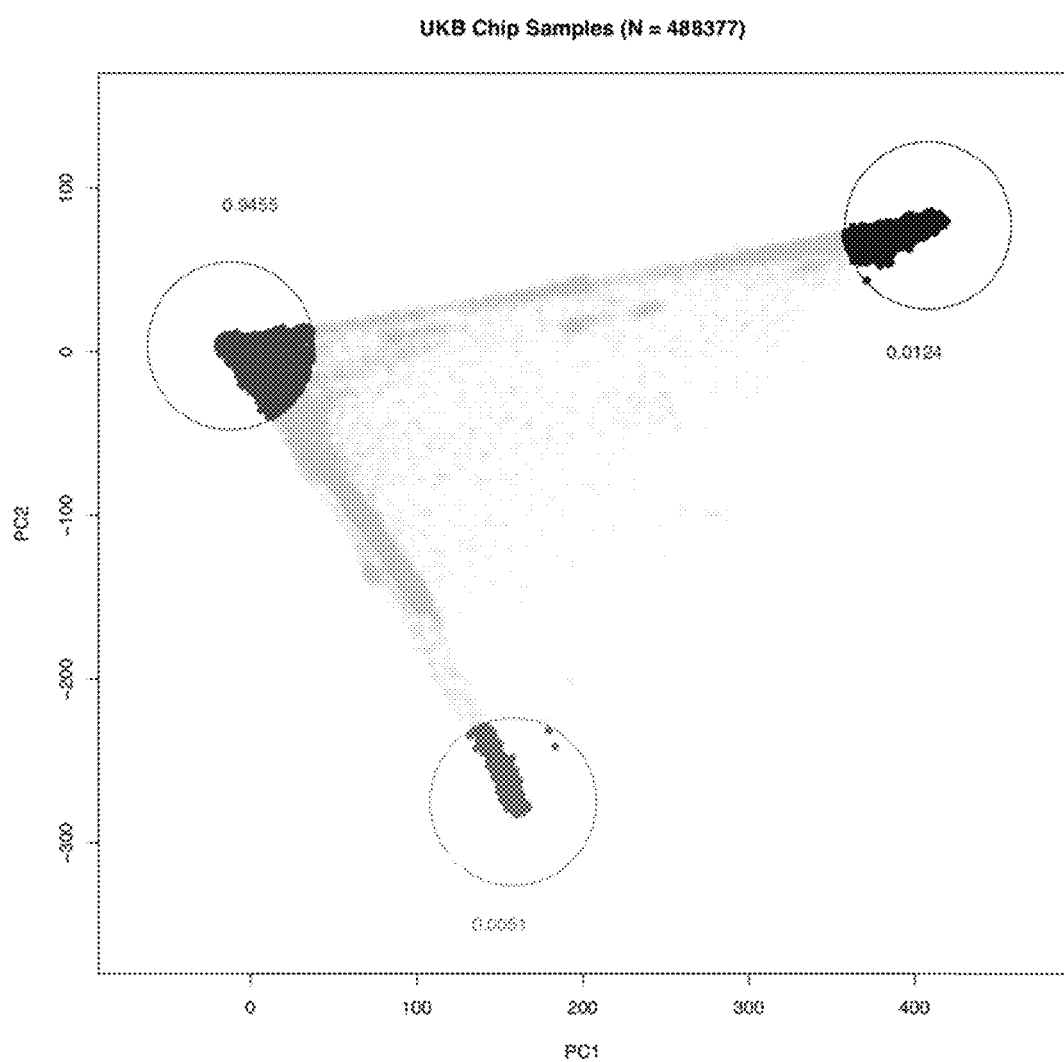
FIG. 3 shows continental ancestry in UK Biobank 500 k and 50 k; principal component 1 and 2 for n=488,377 individuals available from the UK Biobank Data Showcase; three pre-defined regions of a plot of represent African (blue), East Asian (green), and European (red) ancestry.
Figure 3:
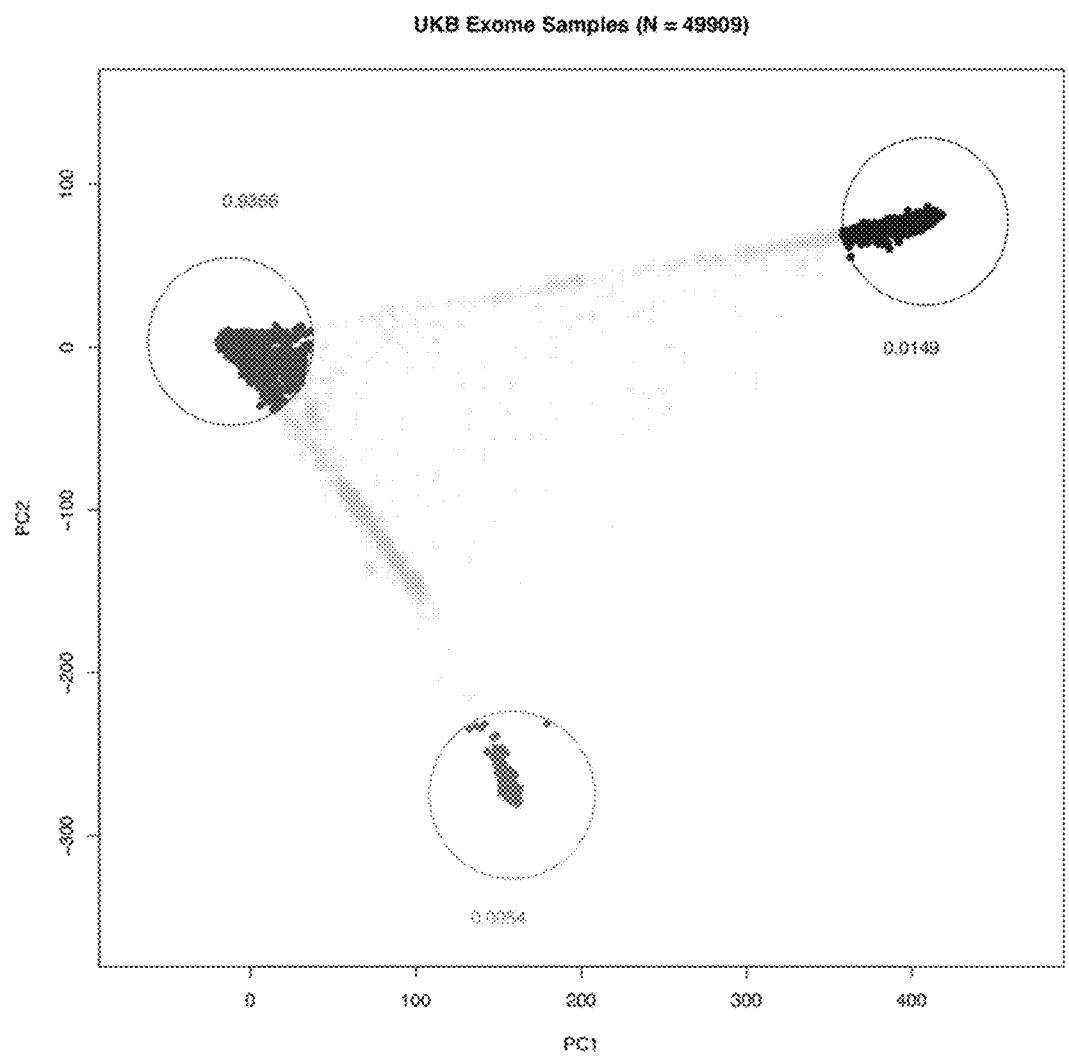

[a]The number of samples with at least one non-missing image derived phenotype value from data downloaded from UK Biobank in November 2018.
[b]The number of samples with exome sequencing data and at least one non-missing image derived phenotype value from data downloaded from UK Biobank in November 2018.
[c]Number of samples in 3 pre-defined regions of a plot of the first two genetic principal component scores, where the regions are selected to represent African, East Asian, and European ancestry (see, FIG. 3).

Participants with WES with at least one HES diagnosis code did not differ from non-sequenced participants in the median number of primary and secondary ICD10 codes or broad phenotype distributions, other than codes for asthma (ICD10 J45) and status asthmaticus (ICD10 J46), as the most enriched in sequenced samples, and senile cataract (ICD10 H25) and unknown and unspecified causes of morbidity (ICD10 R69), as the most depleted. The sequenced subset includes 194 parent-offspring pairs, 613 full-sibling pairs, 1 monozygotic twin pairs and 195 second degree relationships. The distribution of relatedness between pairs of individuals in UKB WES are included in FIG. 1.

Example 3: Summary and Characterization of Coding Variation from WES

Figure 2:
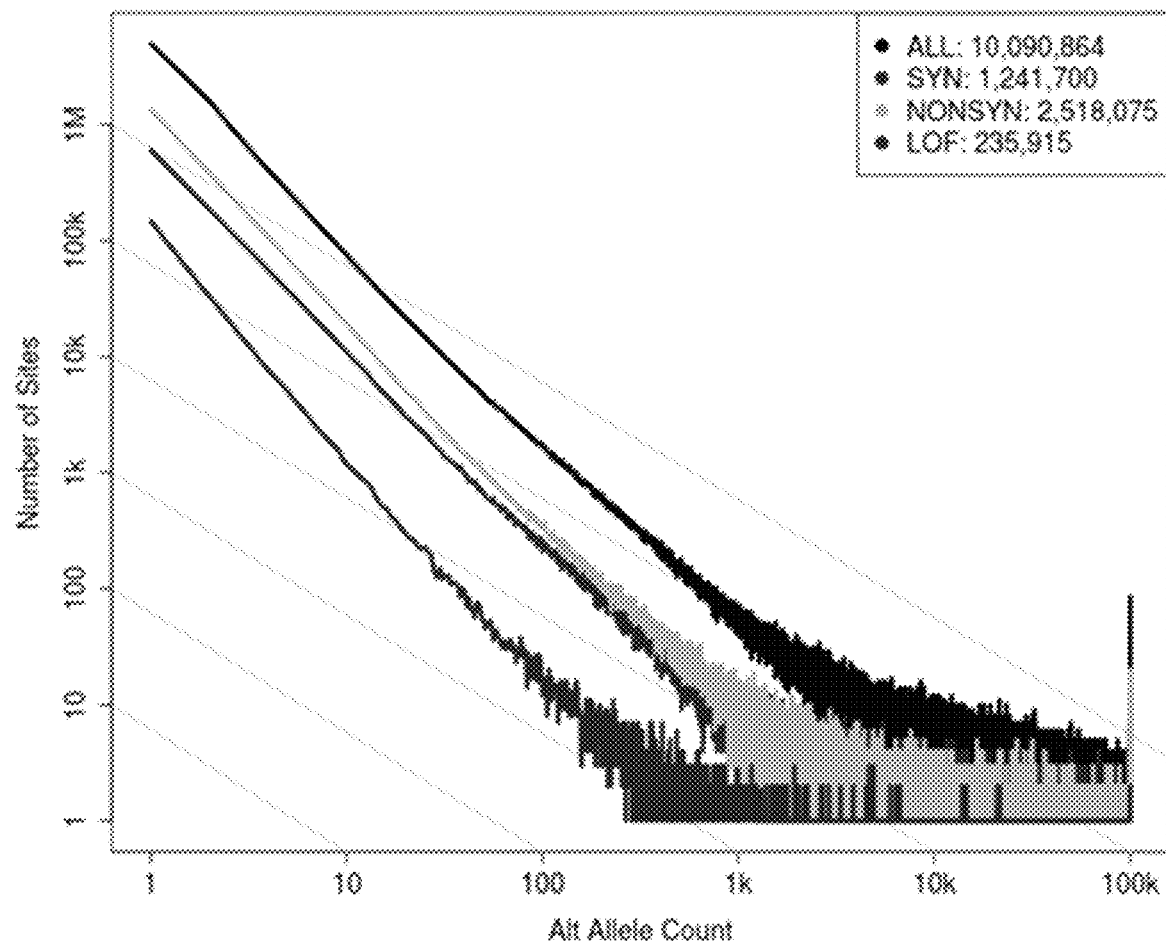
FIG. 2 shows an observed site frequency spectrum (SFS) for all autosomal variants and by functional prediction; UKB 50 k exomes were down-sampled at random to the number of individuals specified on the horizontal axis; the number of genes containing at least the indicated count of LOFs AAF<1% as in the legend are plotted on the vertical axis; the maximum number of autosomal genes is 18,272.

The protein coding regions and exon-intron splice sites of 19,467 genes were targeted. Counts of autosomal variants observed across all individuals by type/functional class for all and for MAF<1% frequency. All variants passed QC criteria, individual and variant missingness<10%, and Hardy Weinberg p-value>$10^{-15}$. Median count of variants and interquartile range (IQR) for all variants and for MAF<1%. The average proportion of targeted bases (n=38,997,831) achieving at least 20×coverage in each sample was 94.6% (standard deviation 2.1%). 10,028,025 single nucleotide and indel variants were observed after quality control, 98.5% with minor allele frequency (MAF)<1% (Table 2). Of the total variants, 3,995,785 are within targeted regions. These variants included 2,431,680 non-synonymous (98.9% with MAF<1%), 1,200,882 synonymous (97.8% with MAF<1%), and 205,867 predicted loss of function (pLOF) variants affecting at least one coding transcript (initiation codon loss, premature stop codons, splicing, and frameshifting indel variants; 99.7% with MAF<1%) (FIG. 2). The tally of 9,403 synonymous (IQR 125), 8,369 non-synonymous (IQR 132) and 161 pLOF variants (IQR 14) per individual (median values) is comparable to previous exome sequencing studies. If the analysis is restricted to pLOF variants that affect all transcripts for a gene, the number of pLOF variants drops to 140,850 overall and 96 per individual (a reduction of about 31.6% and about 40.4%, respectively), consistent with previous studies.

TABLE 2

Summary statistics for variants in sequenced exomes of 49,960 UKB participants

| | WES in n = 49,960 autosomes | | Median Per Participant (IQR) | |
|---|---|---|---|---|
| | # Variants | # Variants MAF < 1% | # Variants | # Variants MAF < 1% |
| Total | 10,028,025 | 9,882,400 | 49,000 (628) | 1,626 (133) |
| Targeted Regions | 3,995,785 | 3,941,162 | 18,670 (235) | 640 (56) |
| Variant Type | | | | |
| SNVs | 3,823,276 | 3,770,454 | 18,404 (233) | 613 (54) |
| Indels | 142,603 | 141,439 | 266 (16) | 21 (25) |
| Multi-Allelic | 466,433 | 459,434 | 2,304 (50) | 84 (15) |
| Functional Prediction | | | | |
| Synonymous | 1,200,882 | 1,175,279 | 9,403 (125) | 222 (26) |
| Missense | 2,431,680 | 2,406,367 | 8,369 (132) | 367 (38) |
| pLOF (any transcript) | 205,867 | 205,215 | 161 (14) | 20 (7) |
| pLOF (all transcripts) | 140,850 | 140,445 | 96 (10) | 14 (6) |

Example 4: Phenotypic Associations with LOF Variation

The combination of WES and rich health information allows for broad investigation of the phenotypic consequences of human genetic variation. LOF variation can yield tremendous insights into gene function; however, imputed datasets are missing the majority of such variation. WES is well-suited to identify LOF variants and to evaluate their phenotypic associations. Gene burden tests of associations for rare (AAF<1%) pLOF variants (pLOF variants identified in WES across all genes with >3 pLOF variant carriers) were conducted with 1,741 traits (1,073 discrete traits with at least 50 case counts defined by hospital episode statistics and self-report data, 668 quantitative, anthropometric, and blood traits) in n=46,979 individuals of primarily European ancestry. For each gene-trait association, the strength of association for the pLOF gene burden test was also compared to the association results for each of the SNVs included in the burden test.

Example 5: LOF Associations and Novel Gene Discovery

In the pLOF gene burden association analysis, a novel association between PIEZO1 LOFs (cumulative allele frequency=0.2%) and greatly increased risk for varicose veins was identified. Results for PIEZO1 for the binary phenotype of asymptomatic varicose veins of lower extremities within the UKB 50 k exome and UKB 150 k exome are shown in Table 3.

TABLE 3

PIEZO1 LOF gene burden associations

| Exome | Counts RR\| RA\|AA | OR (95% CI) | Burden P | N SNV | Lowest P SNV |
|---|---|---|---|---|---|
| UKB 50k | Ctrls: 43285\|142\|0<br>Cases: 1267\|20\|0 | 4.9 (3.1, 7.8) | $2.7 \times 10^{-8}$ | 65 | 2.29E−3 |
| UKB 150k | Ctrls: 131514\|443\|0<br>Cases: 3559\|36\|0 | 3.0 (2.1, 4.4) | $1.8 \times 10^{-8}$ | | |

This finding is driven by a burden of rare LOF variants, with the most significant PIEZO1 single variant LOF association in the UKB 50 k exome achieving a p-value of $2.29 \times 10^{-3}$. Leave one out analyses of the UKB 50 k exome indicate no single variant accounts for the entire signal and step-wise regression analyses indicated that 11 separate variants (5 of which had MAC>1) were contributing to the overall burden signal (FIG. 4).

This finding was replicated in 2,953 varicose veins cases and 75,694 controls previously exome sequenced (OR=2.7, p=$1.86 \times 10^{-9}$). This region had previously been implicated by common non-coding variants with small effects on disease risk, where rs2911463 and other nearby common variants on chromosome 16 have recently been associated with varicose veins (frequency=0.69, OR=0.996, p-value=$1.0 \times 10^{-27}$ in GWAS of 408,455 genotyped U.K. Biobank participants). The rs2911463 variant is not in LD with any of the key variants identified (FIG. 5) and the burden test remains significant when adjusting for rs2911463.

SEQUENCE LISTING

```
Sequence total quantity: 4
SEQ ID NO: 1              moltype = DNA  length = 69883
FEATURE                   Location/Qualifiers
source                    1..69883
                          mol_type = genomic DNA
                          organism = Homo sapiens
SEQUENCE: 1
gggagccgcc gtccggccca gctcggcccc agtgagccga gcgctgcgct ccgccgaggg   60
gcagggcggt cgcctgagcg agcgcgggcc cgggacgtcg gcaccggcgg ggcggccgaa   120
ggagaaggag gaagaggaga aggcggcgcg cgggtcccg cgggtcagcc atggcgcgcc   180
ggccccgggg cccccgcacc gccccatagc gccgcggcgt ccgctcggtc tgggccgggc   240
cctgggcccrt ccagccatgg agccgcacgt gctcggcgcg gtcctgtact ggctgctgct   300
gccctgcgcg ctgctggctg gtgagtgggg ggcgggcgcc tggggggcgac gggaggggggc   360
tgcgtctcgg ctccccacgg cctggacacc ggacgacgcc ggccggggcg agggctgcgg   420
gcgagcgggc gcggaaattc ccagggacgc gcgaccgggg cgcccgcatt cctgaagcat   480
gagcgcgcca ggcggcggcg gggctcctgt cccagggccg ggctggaagg gcggcggcgg   540
ctgggggaga cggcaccgcg tgcccacggg ggcggtcgag cgagcgccgg gcatagcgcg   600
gctggcgtct ccgccggggc gctgcggaga ggaggccgcc gggcgaggcg gtgtttgccc   660
cggtgggaag ggccgcggcg gtggtggggg gagcacgaat ctcttttct ctttcggtt    720
taaaaaaaaa agcgcaaagt tgcatcagga cttcctgaca atctgggaga aggcgggctt   780
cctgcctgga gctgttttaat ttggagcttc ccgagcccaa cgaacgtccg tgcccagggc   840
ccagcccgc tcaccgctgc accccctct gcggactga ggcggtccca cactttggaa    900
aaaaatagtg tgggttcctc cctggtcctc ccttgcccta ctgggctcag tttcgcaggg   960
gcggggggccg gcctctgccc tggtctgggg gaggggacac cccggaggc tgtggcctgg   1020
tgtcagggcg gggcagggt cccagtcct ggcatctgtg ttccctgctt gccgggcagt    1080
ggtgcccctt tcgcgaagca cacccgggtg gcttggtgct gcacggcctg gcacccctac   1140
ccttccccga ccctggccta gccgggaccc agggtccgcg ccctccgccc gggggctccc   1200
cacgtgtgat tgatctggga agcagtcgga tggaattaac ccacggacaa gtgggacggt   1260
ttgcattggg agtccgccat ggacacggca ggtgggggcct tttgattgta aaagcccttt   1320
cggagcccttt gcctcgctcc agtgggagc tcgcccagcg ctagctttgg ggatctagag   1380
ccgcctgcct gaggctccca gacagactgc gttttgatcg gtcgcacaga aaggtggtga   1440
aacttgggga agatttctta gacaggaatc aatgaaaacc attgaggctg gagaggagag   1500
gttttgagca actctcttca gtgcggtcag ccctgtgtgg actgggcagc ctgggacctg   1560
ctcccagtgc agggtcagat gggccgtaaa caggggcccgg ctgtgttcct tcctgtgcct   1620
tgaaaacaag caggacagcc tggcacagag gcagagtcta gagctgacag gccttagaga   1680
gggaaacagg aaagcttctg aaacgtcccg ttcactctga tcgttccatt tcctcttgtg   1740
tctgagtggg agcgggtgtc ctccctgcag ggaatgcccc ccctctcaga tggcagctgc   1800
tccttgggca gagttggcaa tgttttttctt taaatgacca gatggtaaat attttcatgt   1860
```

```
cacaaaatct tcttcttctg gtattttcc agccattaaa tgtaaaagcc ctcctgagtt     1920
catgggctgt acctaaacag gtgttgagcc cgattctgtg gcacatgtgg tttgctgccc     1980
cctgggcatt ggtcagggg cctgggttct gccttctcga ttgctatccg cgtgggggat     2040
ctggggagg gatcactgtt cttcttgctt ttggcctcct tggggaggat ggggaggtag     2100
cccaggggtg ctcacccagg ccccgtgtca gtcttctatg aaacttttaa agaatagtga     2160
tgactgactg tctgtctgta tggtactttc cttaaaccta aaactggtcc caaataaagt     2220
ctcttaattt gaaagatgct gaagcccggg ccatacccca cactgattct gtgtctgggg     2280
atggggcgtg gggcctgggc ctcactcagt gttttctctc agtcacctgg gggagatgga     2340
agtggagccg gccaagaacc ctgcctgcct gcctgctggc cgggactcct gagtcaggct     2400
ctctggccct ggggtgtggg cagctccaga tggacccgcg atgtgcaggt tcagctggcc     2460
tggccggagg tgggacactg gctttgctgt cttttggagtg ccccctccct ctctggcgag     2520
ctttggctgg aagcagttct accgtgtttt ggaaatgaat gaggccttca gaaggcatta     2580
gtcagtgtgt gcctgcgctg gctcagacag tgcctggtga ggggtttgagt catcctgggg     2640
tgccccctggc ccccacgccc tccctctcca gtgcaggatc attacccaaa aatctggcag     2700
ggagctgccc cacccacagg gagcaggggc ctccttcagc agtctcacct aatgttgctg     2760
gagccttggg ggatcagggc ccatctcttc tagagagatg tcagggcagg gctgggcgcg     2820
atggctcaca cctgtaatcc cagagcttcg ggaggcaag gtgggaggat tgcttgagcg     2880
tagccattcg agagcagcct gggcaacgta gagatcccca tctctatgaa aaatatttaa     2940
aaattagctg ggcatggtgg tagtgcacct gtagtcccag ctactcagga ggccaaggtg     3000
ggatgattgt ttgagtccag gagttggagg ctacagtgag ccatgattgt atgactgcac     3060
tccagcctgg gtgacagacc ctgtctcaaa aagaaaaag gaaaaaaag gcaggacat     3120
ttgtgattct gataatatgg gaccgcacct ccagttctat cagtgggaaa tctagacagg     3180
gctgcggaaa gccagctggt gcgagaggag ccaccgtgtc actgactgtg ggacaccac     3240
gtgggctgac aatatggctt ctgcttttca gggtgcctcg tggcacagcc tagggggcaca     3300
cccacgcc gcaagctggg cgtcacctcc ttcaggctga ttgtcactga gaagtgtcac     3360
catttagcat gagggatgct gcctcctttt tcagaacatt gtcaccatca ggtgtcacc     3420
actcctggga ggcggccgag aagctgggga acagcaggca ctcggctcac agttgctcag     3480
cagtgcagac cctctgagct gagcatggca gagtcaccct tcggaggcct gtgcccgggt     3540
ctcaggacct gcacagaacc ctggcctgtc ccatccgagg gtgctgggaa gagcatggcc     3600
gtggcagagt aggggtggag ctgctttcct ctgtggcttg ggggcccctt ctgagcatca     3660
gctcccctggt gtgacagagg ggcgcactct gtccgccatgc tgggcctgga ggctggatga     3720
gtcagcagga gagcctgggg cctgcctcac agcaccaagg gctgcaggtg tgagtgtgca     3780
catgtgtgcg tgtttgggga aggggccagg gactgcccag gagctgagga tgggtcacag     3840
cgggtgctcg tcccgcagcg ggtcactggt gcccaggaca cagggagctc cagcccccagc     3900
tgccagggtc ccacagagag gaagtttcct ctgggggtgg gggggggcgc acagtctctg     3960
atcctggccc caaggcagct tcctgggcgg tgtctctcct gtgctgactc ggcagtgcat     4020
ttgctttcgg tgctcaaaga tgaaggggaa ccaccgtggg ccttgacggc ctcatctgcc     4080
cgctgcagcc cactcctgag atgggaccac cgcagtcgtc agggtccagt gagagccgca     4140
tcttgcagga agccattcct ggcctctctg gcctcagaaa tccccttttc aattcaacaa     4200
aatgttagtc ttctgtttag ctattttaga aatagacagt taggcttttt tctcttttt     4260
cttaaagaca gaggctcact ctgtcgccca ggctggagtg tagcggcgtg attttggctc     4320
cctacaactt cagcctccag ggctcaagcc atcctcctgc ctcagcctcc tgagtagctg     4380
agattacagg tgtgtagcac cataccata ttttgtattt tttgtagaga cggggtttca     4440
ccactttggc caggctggcc ttgaactcct gaccttaagc gatctgcccg cctcagcctc     4500
caaaagtgct gggttacag gcatgagcca ccgcgcccgg ctgacagtta gacttttgct     4560
tctttgttta tataagcttt tccttctggt tccaaaagca gttgccct tccttgtggt     4620
agagaatcct agctcacaga gcagtttaga agccagcaca gtatcccaca cacacatctg     4680
gcatggacag accccttctt gctgggtgtg ggtcctgtgt tcttctgaaa ggcaagctgt     4740
tcccagccaa cccctgcccc tctctgcctt agcctgcctg gaggcctgag tctcctgggt     4800
gactgtgagg tgggacccc ccttccccta cccccaccca catcctctgt atctgccttc     4860
tgtcctgctc ttgaccttg agctcctctg ctggcttcag ggtgcggctg ttgagcctat     4920
ttttttggatt aggactctgg ggtgagggaa gttaattcac acacccaaga tcacactggt     4980
gggaaggac aggcccgggg tgaaggcttc tcctctcctt ggcggttgag tcccacacct     5040
gctggccgag gcacctgaag gggacttggg gtccagggtc actgggagga cgggggcagg     5100
cagaggggtg gccgacctgg tggcggctcg tgggcagcag ccgacccctat cttgctctga     5160
acgtgtgggg ccctcacccc cttctctggg tctgggtttc ctccctgta agtgacaccg     5220
taaaagcttc acagccgctt ccaagtctca ggtctctcgg gctttggatc tcacacccag     5280
gctgggtggg ggtaggggcg ggacagccgt ccccccggaa aggctcagaa ttcctcgcac     5340
aatcgtgggg ccaggagacc cgcaacacag gctttcccag ctgcgctgag tgccgcggtg     5400
gccggggtc cgtcgggcct ccatggagct gaggggaagg tggcactcac cgcctggtcc     5460
cggagcacac agggcagctc ccaggagcac agaggctcct tgggacctgt ggggctgtcg     5520
gcctccctca tgctgcacac acagcgcgtc cccaggggtg tctgcagccc agcccatccc     5580
actgcagatt cccgaccact cagattcatt catgcatcct ctcacgccgg tcctgtggga     5640
cagagctctg ggcagcagcc agaagtccaa gttctgattc agggccagtg gaggtgggtg     5700
ttggggtggg gctggagctc cctgctctcc ctcccaagct agccaggaaa ggaggttggg     5760
ggccccgcac ggtcattgct gtttattcac aaagcgcgat gctgagcaca ggcggggaaa     5820
gaaaagtgcg atcagtgcca ggaaaatggg gctcccccga cgccgccaa aatgggatcc     5880
cttgccgggc gcggtggctc acacctgtaa tcccagcact ttgggaagcc gaggcaggtg     5940
gatcacctga ggtcaggagt tcgagaccag cctgaccaac atggtgaaaac tccatctcag     6000
ctaaaaatac aaaaattagc tgggcatggt ggcgggcacc tgtattccca gctgggaagg     6060
ctgagacagg agaatcgccg gaacccagga ggtagaggtt gcagtgagcc acagtcgtgc     6120
cactgcactc cagcttgggg gcttgggga cagcaagact ccctctcaaa aaaaaaaaa     6180
aaaagtgaag tcgtaaatca gattaaattc ccttttaac cctttgaacc tctgtcctcc     6240
cctgttccca gcgggaagcc tctggtgaac gcgccatgca cccaccctgc cccgctctc     6300
tgggtctctc tcccagctgg aacgccgct tccccaggtg ccttcctggg gccacagcct     6360
tgtgcctcgg cggctgctgg atgcctgggt gtgggtgg ctccagtgt gtggatgggc     6420
acacgagcct ctcgccccttc tgtgtggggt cgcacaccca ccgcaggccg tattttttgct     6480
cacgttcatg tttctccacg gtggacgctg ggttgcaggg acccttcctg tgtgcgggtg     6540
aggatctggg cagctgctgg tgccgggccc atggggacgc tgaccgtccc gggtgccggc     6600
```

-continued

```
tctgaggtgt gcagtggacg gctgtcctgc cgggcgctgc cagggcccct taggccgacg    6660
tgcgtggcca cccgattccc cgccgttgtc tcaggaacct ttgccgagtg gggtggatca    6720
atttttcggg tgtgttttaa tagcataatt acagggagta tttcaggctc cctctgacgg    6780
gccggcaggg ttttggctgcc ggctgtttac caggctccaa tctgcacact attttctgt    6840
gggtatatat agctggggct gcttctcctt cctcaggttc aggctaaaga gggacagcag    6900
ccgcctcagc cacccctgt ggttttcttt gcctgtggat gggcggctaa aatgggccca    6960
ggaagagtca agaacaaggc cggctctcgg tgccacagct ctaccccaa aagcaggaag    7020
ggggctcggg ccatgcccat ctgtgagcta caccggtccg ggagcggcat caggcagggg    7080
agtcctggac ccccgcagtg ctggggtgtg tttgtccgcc ctccctcccg tgtgtctaga    7140
agcctccagc ctcgggaaa acaatgaaac tcaactgtga cttaaacaga ttcccaggcc    7200
cgcaggagct cccggaggct tgtggctgtg gcgagacctg gagggccatg cgggagggac    7260
agacgcaggt ttgcggaggc cgcctgccca ggaggggcgt caaaggaggg gacagatgtg    7320
ggtttaggga ggccacctgc ccgggaggag cctcgaagga aggcacaggc gtgggtttgg    7380
ggctgcctgc cctggagggg cctcaaggac cccaggtctg gtcttggtct cactcacctc    7440
ctggaccccc caaggcctgc agtttgcaat ctgtcgcctg gaccccac tgtctgcctt    7500
tacgcagctc agccaccacg cggccctcgc tccctcattt acttgattc tgtttatggt    7560
taaagtaccg tttaaaacga cacatcatta aagcaacatg aaagggagtt ttgaaaaggg    7620
aagccatcgt ccatcccact gcccctgcct cagcggggat ttacttttcc tttcctgtct    7680
gcgggccagt gacaatgagg accccgcaat gtgtctgcgg gccagtgaca atgaggaccc    7740
cgcaatgtgt ctgcgggcca gtgacagtga ggacccccgca atgtgtctgc gggccagtga    7800
cagtgaggac cctgcaatgt gtctgcgggc cagtgacaat gaggaccctg caatgggcgg    7860
cctgtaaggc tctgccctgg cctccgctgc ctttgctttc tccctccttg gtgggtgcac    7920
gcccttgtgc ttttcctaaa agagcaggtc ctccggcat ggtggctcac gccggtaatc    7980
ccagcacttt gggaggccga gacgggtgga tcccaaggcc aggagttcaa gaccagcctg    8040
gccaacatg caaaaccctg tccctactga aaatacaaaa attagctggg tatggtgaca    8100
ggcatctgta atcctagcta ctcgggaggc tgaggcagga gaatcacttg aatccgggag    8160
acggagtttg cagtgagccg agatcacacc attgcactcc agcctgggca acaagagcga    8220
aactccatct caaaaaagaa gaagaagaaa atcctgacac ttcagcctgg tgcaggccct    8280
tccctccttc tagtccctgc caagaagtga gccgggccca gatctcctgc cgggcgggga    8340
atgagcacac acattcccct cttggagcag acagcagcag cagccctgtt gcacacatga    8400
ggacgtacag gctcaggggc cgtgggtggc agagaggcta tcagcgccgg actggcccgc    8460
cccgagccag ggtccagccc cacagtcctg tccccaagcc ctggcccttc tgcggtcact    8520
cccgtctgct gaatccccta ctctgcccct ggtgtgtggc cccccagttc cctcctgtgt    8580
tcattccctg ctaacctccc gtggcttcgc ctccccagat gccctgagca cacagcctct    8640
cccccttcctc ccctcctaga tgtgcacata ggagccgccc aaaggctggg gcagctagtg    8700
gggcccctcc aagggaagct gggccccggg caatgcctg agccaccagg tcctggccct    8760
gcgtctcatc ccttctttt tttttttgag acagagtctc gctctgtcgc cctggctgga    8820
gtgcagtggc ccagtctggg ctcactgcaa gctctgcctc ccaggttcac gccattctc    8880
ttcctcagcc tcccgagtag ctgggactac aggcgcccac caccacactc cgctaatttt    8940
ttgtattttt agtagagacg gggtttcacc gtgttaacca ggatggtctc aatctcctga    9000
cctcatgatc caccgcctc ggcctccag aatgctggga tgacaggcgt gagccaccgc    9060
gcccggcctc atttggttcc ttctgtgcac cacagtgtgg gatctcgggt cctgggtggc    9120
acgtgtttaa cctgaaagga aactgccct gcgctcccca gcttgtagcc cgtgggccg    9180
gctctgaggc cccgactgcc ccacggcctg tgctgcgcat gctggagcca ggctccggct    9240
ctggttggcg cctcccgtgg cttttaatctg cagtgacctg ggtgcttaac gagggccttt    9300
gcctctgcgt gtgcactgcc ttcttctgag gagtctcctc aagtctccca gctgtttaaa    9360
caatggggtc ttttgtcttt tgacctgttg gtgccatcag ccagcctcct gcacatactc    9420
tccctaccct tggctgccac tcctgtcctg cccttcgcca tgtcttttt cttttctttt    9480
ttttttttt ttttgacagc gtcttattct gccacccagg ctgtagtgga gtggcacgat    9540
cttggctcac tgcaccctcc gcctcctgg ttcaaccgat tctcctgcct tagcctccca    9600
agtagtagg actacaggtg cccaccacca cacccggcta attttgtat tgttagtgga    9660
gatggagttt caccattttg gccaggctgg tctcaaactc ctgaccttag gtgatccgcc    9720
tgccttggcc tcccaaagtg ctgggattac aggcgtgagc cactcgccgg ggccccgcc    9780
atgtgttttt aagagcaggc atttcattca gatgaagccc ggacactctt gggggttctg    9840
ctcagggct ctacctgcca ctgaacgtcc tctccctgtg tgggtggcca tggcattcag    9900
cctgtgttgg gccttgttct gcctggctac tggccgctag gtctgccccg gcatcctctg    9960
tgtcctgtgt gggcgcctct gcctcctgct ccagcctgtg ccaggcaatc ctgctcacct   10020
tccaggagcc aggcctctcc ccagggcctg cgtcctgtca gggtcaggga cggcccctct   10080
gccatgctcc ggagtccctg gtcccctcac tccgttacgt cctgggtgtc acgggtacgg   10140
ccgggaactc tgtcgtcttc actgtctggg ccggggcctc cctgggtgtc tgctggatgg   10200
agtgggtgcc tttgggtccc tgcaaagtga gcctgcctcc cagcaccgcc ctgtcgttac   10260
atagccacta tctttgcgcc tgtttttcct tcctttgact ggttcctctg ggttaattc   10320
ccaggcctgg tattaccatc tctgaatgcc tgggtggttt cagcgcccag gaggctgtgc   10380
tgaggtatct tagaccatgt gggcaccgtt cgctcctgcg tacccggctc catggtggga   10440
tgttttgcg gaatcctgca gggaacccca tgtaccctaa gagtgctctc cccagccact   10500
gtggcataag acaagcggtc tctttgccct tgggcccat ccttgtctgg tcggcccttc   10560
ttcatgggtc cagcgcggga ttgccggctt ccttttcagg cttcctggga cccccactca   10620
gacctgcagc tgggccagcg atgcccacc gtttctcctc cacgtggtat acagaggtgc   10680
ccaggctgct gctgggact ctggagccca ggagtgagtc tccttgaccc tgagctgtca   10740
tggctatcac agctgggtcc tgtttttccc ttcagcaccc acgggtgtct ttctccagtt   10800
tatattgtta ttttttattta tttacttatc gagacagagt ctcgctctgt cgcccaagct   10860
ggtgtgcagt ggcacaatct cgactcatcg caaactccgc ctcccgggtt caagcgattc   10920
tcatgcctca gcctcctgag tagctgggat tacaggcatg tatcaccagg ctggacctct   10980
agtttatatt attacagcct ggtcagggag tcactgggta ctggtgggga tttttttaa   11040
agggggccca ggcagaggcc aggaggaggt gacagtcatg cgcttagaag ctcaggccac   11100
gcccacccag ccctgcctgg tgaccggttc ctgctgtgtt gggagctgca tcccagacct   11160
tatgccggg cacagaactt ccaagccagg ggagagggag gcctgagggg gccccaatct   11220
ctgaaggtca gcagtggcgg ggaggaggct tgcggtgctg aagggactcg ggggacctgc   11280
agggaggtgt tggtggtcag ggatggtggc acctgagggg acttttggca gggccagaag   11340
```

```
tgcccagagc aagctccggt ggggccctgc actggagggc tggggtcgag tgaccctctt   11400
cctaagacca cccaggagga cactgggtgc agggtggccg gagccctcac ccccagtagg   11460
cagctgctgt ccactccgcc gacctgcctg tcacccagta ggcagctgct gtccactccc   11520
ccgacctgcc tgtcacccag taggcagctg ctgtccactc ccccgacctg cctgtcaccc   11580
aataggcagc tgctgtcagg tcccccgacc tgcctgtcag cctttccct gtcaggccct   11640
gttcctagga gcctggagac ctcaggggtg gccttgagcc cccagggttt ttttgagggg   11700
aagcgccagc tgctgtcttc acccttcccc tagtgaggcc aggctgtgca gggcacgtg   11760
gaggcagtct gtgctgcgcc catcggtcgc ctggcttcct gccgaccctc ggcccccagc   11820
cacctctggt ctcgggcaag gcccctcccc ctgcccacct cctccctggc cccacgccg   11880
ggtgggcaga cctcctctgc ggttttatt caggggtcc ctcgttggct gcccactctt   11940
ggagggctgt cctgactcag gcctcccctc tactcagatc ccctgagcga gggcctgggc   12000
gtgacgccgg gagttactgg ggggccagag ggggaggctc agcctgaatc aatgagaccc   12060
aggaggaagg aggcacgtgg aacctgagggc tggctggagc cgctggtgac agatggagga   12120
gtaattgctg cttccagagc acagcgagct cgagctcccct ggagtgccag aagcttctgg   12180
gtggacagac aggccgcctc acattccaga ggctgacaca gtcttccagg cacccctggg   12240
gccagctgga agccatgtgc ctccactcac gtgtcccgtg ggtgtttgga ggggaggctg   12300
gccctgccat ggcccacccc agcctgcggc ctcaggagct tgcacatttg caaggggtg   12360
acatgaagac tgagccaggg ctgcggcggg catccccctc agagaacagg gaggaggggg   12420
cacaggcctt ttttttttt ttttgacag agtctcactc tttggccagg ctggaatgca   12480
gtggcacgat ctcagctcac tgccaccttc gcctcccagg ttcaagcgat tctcctgcct   12540
cagcctcccc agtagctgag attacaggca cccaccatca cgcccggctc attttttgtat   12600
ttttagtaga gacgggtttt taccatgttg tccaggatgg tcttgatctg ttgacctcgt   12660
gatctgcttg cctcggcctc ccaaagtgct gggattacag gcgtgagcca ctgtgccctg   12720
ccaggcacgg gccttttat gagggaggaa gccgtgccct ctgccacctg cctgtgggct   12780
ggggcctgca ggctcccagg gccctcagct ccagcgtggc tgttggttat ggcacctgg   12840
gcctcatgtc cacatggaaa gtatattccg agctggtggc taagccacaa gagcctgctt   12900
acctgtccca accccggct cacttgctgc catgatacgt ctgggattct gggccctcct   12960
tctgagcttg gacacagact tgggacttca gcgctggaca caggtgctgg atctggggtc   13020
tcaatgcac cagggatggt cattctgaca gccatgccca gagtctcagg aggggcctggg  13080
gccgcaggtg gacaggcatc ctgaccagag tctcaggagg gcctggggcc gcgggtggac  13140
aggcatagag tctcaggtgg gcctggggcc gcgggtggac gggcatagag tctcaggagg  13200
gcctggggcc gcgggtggat gggcatagag tctcaggagg gcctggggcc gcgggtggac  13260
gggcatagag tctcaggtgg gcctggggcc gcgggtggac gggcatagag tctcaggagg  13320
gcctggggcc gcgggtggac gggcatagag tctcaggagg gcctggggcc gcgggtggac  13380
gggcatagag tctcaggagg gcctggggcc gcgggtggac gggcatagag tctcaggagg  13440
gcctggggcc gcgggtggac gggcatagag tctcaggagg gcctggggcc gcgggtggac  13500
gggcatctgg acgtcggctc cactagtgtc acctctgcaa ccttgtccca cccagccacct  13560
ccctatggcc ctgctctgac tgtgggctga ggggaccccc catggctagc ttgggacctc   13620
cgctggacac tgtcataggg cacttgtcga gtggccctgc tgaggtttcag gcttgggcgt   13680
gtgtggccc tgagcccagc agctgcgtga gccgtgggga gccgagcccc cagtcaagaa   13740
agctgtgtgc tccttaccct gcctgctggg cttgggggcct gcagggcaag ggaggcggtg   13800
ggatgggagc ccgcctggc ctggtttctt gttgtcgccg cactcctagc tgtatgtagt   13860
cagatgaggc tcccagtcct ggctctgctg ctgagcacca ttgggccggt ggttgggtga   13920
atctctcagc ctctctgagc ctccagcact tcgtccttaa gagtggaact ggtctggacc   13980
tcccaagggg gggtcactgg gtgcagagtt cctgcaaggc tgggcccggt gccagtagcg   14040
gtcgctctgt ggggcctttc gcacggttga ttttatctc cctgtgagat tagcgcctgc   14100
cctgctctgc ctcacggctc tggctctccg ggactgagac cacctgctaa gtgacagggg   14160
cggaaggacc ttgcaacaca gagcaagacg tgataggtg gagctgctcc gcccaggccc   14220
cgcctgcaga tgagagggcc cagagcctct taatcccctg cgctcagggc atgtgacggc   14280
agggagtctc tccagtgccg cccaccggat tcctatagtt agagctcctc gcccaagccc   14340
ccagggcacc tcactggcct cccaggtgag gacatgacgc ccagcgactc tggtggtggc   14400
tggtgtcacc tatggcaggg ccgcgcgggg cccagtggag gacgcctggc ccggacctga   14460
ctgctccgtg ggaaccgtgg ggcgtgctca gggtgacttg gtgcggctgg gctgccagcc   14520
ggcctggctg agtcactggc agtgaaggca ccaggtggtg gacgtgctcg gcagctggcg   14580
ggagagtacc cccacccagg accgtgttca ggctgaggggg gaagggagcg gcccaggcag   14640
gcaccgccca tggcggggcc cccgcactaa cggccaccct ccccgatgga ctgcagttct   14700
ggagccgccc ctgaggagaa cgccctgctc agtgtcctgg cagactctgg actcttcacc   14760
gtgccatcct cgctacagcc tggccaggca gccgctcccg tccccccacc ccacagacag   14820
gaactgcaga ctcctaaagg tcgagccagc tcccaagtcc atagccagaa agtgatgcag   14880
gcggggccg gctgggggc aggtgtgacc gggtcatggg ggagcgggct gtgcacaggc   14940
atcaggctga gaggtctcgg ggatacgtcc tgggagccgc ctgccaggcg tcctgtgggg   15000
ctgcctgcag gcctcctctg gctttggcag gttctgtccc gacagaccga ggcttgggaa   15060
gaccggattg tgcactctct gcctggagag agggtgggga gggctgggg cgtgtgggca   15120
gggagaacac cctgggaggc atcagtcctc ttccctgggga acgggccatg cgtcaacagt   15180
ccctcacttc ctctctcagg ggcagaggcg tgggggctccc gagcctccag gttgagtag   15240
gttaggaggg cctcagagcc ccctgctgcc ccgccatgtg gcattggaag gggtgtgacc   15300
ccctagggga tctgttaacc acactccgcc ccatgccggc ctctctgttc cctctaacct   15360
gcgcaggagc agggccagct ctgagctagc agaggtgaca tgaggctcgt cctgccccg   15420
cccaccctgg cccctccctg tttcccacca cgctccgccc accagagcta catgttgtgt   15480
ttgagcctca gccccagacc tggctcaggt cctcaggagg aagcagtgac agccaggccc   15540
ggggtcctct ccctgtcctg ctccctgcgt gctgactgga ggctgcaggt ccccaggctt   15600
ggccctgacc ctcaggaatg gagccggccg atgtgaggtg gggctccgg tcatgtgcag   15660
tggtaggaga ggaggcggga ccggtcccac agctccattg ctgccgaggc gttccgcagg   15720
tctgtcttca tattggtaag gaaaatgcga ggatgggtga gcctgggcat ccagtcccc   15780
aagtccgaaa tctaaatcca agcggaaat tccaggcctg acttcatacg ccaggtcaca   15840
gtcagaagcc agaattattg aaagtatgct ctgggcgtgg tggcctcaca cctgtaatcc   15900
cagcactttg ggaggccatg gtgggaggat cacttgaggc caggagtttg agagcagcct   15960
gggtaacata gtgagacccc cgtcattatt tacacaaaat tatgtgactg cctttagggt   16020
atgtgtacga ggtatatatt gaaatgtgag tagaattttg tgttgagtcc catccccaag   16080
```

```
atacctcatt atgcgtgtgc aaatattcca aaatccagaa aatcctaaac tggaaatact   16140
tctggcccct ttggatgagg ggcccccact ctgcatagca agtgtgggcg cgggtgctgc   16200
tgtgtcctag cgtacttcag tgtgtggcct ttgcagtgaa tagggctggt gtcctcactg   16260
tacagatgag gaaactgagg cccagcttgc tttgccaagg tgcatccggc cccggccatg   16320
gctattctgg ctccagatcc catgtgtctg agccacaata ctgctgtgcc ccggactggg   16380
ccctgcagct cgcggtgtcg ctggcctgcc cattgtgggc accgccccca ccccagactg   16440
gccgaggcct agaagggagc agggcctggc tgaggctgca ggggtgggga cggtcagcca   16500
gcccctcact gccaggaagg gcgcatccat cctggcctct ccccagggag aagggaggag   16560
cggctgagag ggaagcgctc ttgccctgtg gacgagctcc tgccccacgg actagggag   16620
ccccgcccac aacctgcttg tcagggccac ccgggacccc cgggagttcg gctgctcgct   16680
ctgctgttag gaattggatt agttttccat aaaaacagga tgtggtgggt gagagggcag   16740
tgtgtccgtc tttctcactc ccctttttcc aggaactgag cacgcgcata ggttttagcc   16800
agggccgtcc agtcccctcc ccaccccca cagggaacaa tccactctct gctcttaagt   16860
ggccacttaa tcagcttctc ctcctggccc ggggagctc ttggagccgg cctgccgtgg   16920
tgggaacagc tatggggaca ccctgccata aggtccagca gctaagctgg gatgtggggg   16980
gagggctgc gaggccagg cagtgtgcca ggccgcacaa gaggagccca gctcttgccc   17040
caccagctgg cagccctgga ccgaggttgg gcccgtgagg ttggctgggc cctgggccct   17100
gggcccccct cccaggaca cgactgtggt ggcacatgc tttgggggct cgtgggtccc   17160
actttgcaga cctctgcttt aaggggtctg gtccacgggg tcccctctgg agggcctggg   17220
ggaaatctca gggacctggg gtctggaccc gggggaggga gcgggagaag catgtgcgtg   17280
agtctcgtgc tgtcagggag cccggaagt ctgcgaggggc ttggggggttg tgtcagggag   17340
tgtgggtttt gcccttcagt ggtggaagct ggcttgatc ccctcgatcc ctcaaggctg   17400
tagtcctgac tcgggctgt agggcaggc agggtgggggt caccctgagg cagaaggctc   17460
agcggagatg ttctggcttg gctctgcccc tccctggctg ggtggcctca ccctgtgacc   17520
tttggggacc ctggttcctc tgagccaggg gacagcagtg actccgcctt cctaggtggc   17580
tgaggatgac atgggctccc cctgcaaatg tgggttctgg ctcagtggcc aagtgtatga   17640
tggtatgtgg ctcttgggt cctgagagag atgggagagag agcaggggtt tgtagggaag   17700
ctggcggctt ccaccccagc cagtcacctg cagtggggga gttccaaagc tgactgaagc   17760
ttcgaccttg tggctggtcc ccttccttcc tgcctcagtc attctggtct ctgggggatc   17820
agggctgggg ggctctgggc tgtgggggcc tgttttttgtg acttaaagct ctcccagcac   17880
agccccctga cctccttcct catgggcagg acctggccca ggggtctcag cacagccaca   17940
ggccagggat gcccttgcag atgggcctgg atggaattcc agaactcaga aatgtctcct   18000
tcccgtaagg atgtcccgag actcatgaga ccgtttcctt ctgggaaggg ggaggaatgg   18060
ggagatgagt gaagagcgca ctgcagctca atccgggaag aagctaatca atcaatcagg   18120
gaagccaatc gatcggagaa gctgatggga aagctgtgct tggtagaata ggctcgtgca   18180
ggcagagcag tcgcgcact cacaggctga ctgtgaggac cttgggtgtt actttgtgct   18240
tctctgcatt ttaaaaactt ttgaaagtgg agaagaggaa agtgaatgtt ctctgagatt   18300
tcatggaaag gggaaactga ggcccactct agccagtttg ggcccagggt tccaacctgg   18360
ggtggccccg gccctcgtgg cctgaggtga tcgtccctgt ggctctgaga gcagctgggg   18420
ccgggtcccc gttctgggc tggtgatcct ggggaagagc caggcagtgc cctgcccacc   18480
tagtggttat gagcccagaa tgttgatttt ttcccttgg ttgcttcatg actttgttga   18540
atttccagag tatgtgtggg ggccccggc gtccactcg ccccagccct gtggcagcag   18600
agctggctgt caagctcagt cagctgggcc cagggcccg gaggtaggtg ggtgtgtgcc   18660
tgagcttccc cttgggccc tgccaggtgc tgggagggac cacacaggcg cagagaactc   18720
gggtccca ggcctcggcc acaccagcct ggtgctgtt atatattgat atgtctctct   18780
acctgtgaaa tgggtattta ttttaaggag ctgacgcacg cgattgtggg gctgtcacgt   18840
ctgaagttcg cagggcgcgc tggctgtcaa gagccgctgc tcagtctcg agtccaggct   18900
gtgcgctcag gccgggcttc tctgtggcgg tcctgggaat tcctcctccg ggcccttagg   18960
cgacactccc ctgccttcag ctgattggat gaggccctca tgccgtctgc tgatttaaat   19020
caatctcatt ttaaaacac ctgcacacca aattgcgatt ggcgtttgac taaactgggc   19080
agcgtgccc agcagcctg acacatgaat caaccctcac accccaccg caggcgtgac   19140
cacggcaccc acgctgccga ctgagaacac agccgtgcgc tgactcgcat gtgatgtctc   19200
tggtcgcacc tcctccatcc tcagcaccct gttcagaatg gagatagcgg ccgggtgcag   19260
tgctcacacc tgtatcccca gcaccttggg aggcctgggt gggcgggtca cctgaggtca   19320
ggagttcgag accagcctgg ccaacatggt gaaacccat ctctactgaa aatagaaaaa   19380
ttagccgggt gtggtggcag gtgtctgtag tcccagctac tcgggaggct gaggcaggag   19440
aatcgcttga acccaggagg tagaggttgt agtgcgcgag attgtgccac tgcactccag   19500
cctgggcggg cgacagagtg agactctgtc tcaaaaaaaa aaaaaaaaaa aattagagat   19560
aacgacttgg gctctctaga gaccagggag ccaggctcca ggcgctgctg tccagcccct   19620
tgccagctat acgaggtgct cacctggcca cgtgtccggg cagtgcttct gggggtggcat   19680
ccactgggag ggcaagatgg ttctggtaca ggtgcccaat tctgtcccca tttcacttac   19740
tgggaactca aggcacagag aggggagggc tgagctagga ccagacccca gtctcctgca   19800
gaagtacaca gacatgatgt acgaccatcc tggacacctg ccctgagatt cccctccctc   19860
tcctgccctg tcccagtggc ctgggggaa gggaagcaa ggttctgaag gggtgtgac   19920
cagacacctg cccgtgacac cccctctcca ggctgcctcc gagtggctgg tgactcccct   19980
cctgcctgcg agggaggtgg ccaggttgca ttcctctctg agtgccgggg aagtccctag   20040
agagcaggcc agcctgtgac tgggccctgg ggcagtctag acaggccaga ctggacaggc   20100
caggggggctg ggtgccgctg ggtaaatcac agggtgaggg ctctgagtca gcaccccatc   20160
ttctgtcctg ggtccagcac cgctggaggac acagtgggca gccgggtctg ccagggccag   20220
gtagctgtgt tgagaaggca gtgctcctga gaggcggcta ccgggaggtt ttcaatggcc   20280
aggcttctta ggaagccctt gttgcctctc tggggtgagt tgctggggcc atggttggag   20340
tggtcgccag tgtctgcccc tggtgccgag gcggagtcc tcgtttgggg aggtcacggc   20400
atgatgctgg gagtcaaagg caggccgtgg cagggccatt ccttttttct ttcttttttt   20460
ttttttttg agacggagtt tcactcttgt cgcccaggct ggagtgcaatc   20520
cagctcactg ggatcccagg ctcccaggtt caagcgattc tcctgcctca gcctcccgag   20580
tagctgggat tacaggtacg tgccaccatg cccggctaat ttttgtattt ttagtagcga   20640
cggggtttcg tcatgttggc caggctggtc tcgaactcct gacctcatga tccacccgcc   20700
ttagcttccc aaagtgttgg cattacaggt gtgagccacc gcgccggcc tgcagggga   20760
atgtcgacgc gtgatctctg cctggagagc acgttcatgt ttcccagagg acactttaga   20820
```

-continued

```
acatggcgcc tgggtttgga tgaacctcag cctaagaatc tacctgctca ggatccagcg   20880
acgctggtgg tgtggacttc agctctggag aatgggttat atggaacctg ggcgccggga   20940
gggcattgcc acgtgcttgc tgctggggct caagaggac cccatcctcct gtggccgaga   21000
ccccgtgtct caaggcacat ccccttttcgt accccgcccc accctccgca gcttcatgac   21060
ctctggtttt cccccaggac cttcgcatct gatgttccca gatccttcct gccactgggt   21120
cctgctctgg tgcccccgg ggaagccttc cctgaggacc cagctcagca tctggtgcta   21180
actgtggctc atcgtgcact ttggcccccca ggaggctgtg ggctcctgaa accctctga   21240
accacggct tccaaccaca cctgaccccc tgcgtgccga ccctgtgtgc aggtgtacag   21300
gtgtgcctgg ggcaggatgg ctgtgacggc ctcacagagc cggagagct gcctcctagc   21360
ttccaaagcc ttcatttcag gaatcttacc ctctcaatta gtctggaatg ctggggcggg   21420
ggccagctcc aggtcacaga gcgaccttgt ttacccagac cttaacatcg gcccttccat   21480
gctaatcaat gtaatcattg tggtccatgc ggcctctgga atgtgctgtc cactccctgg   21540
gtcagccaga gagtgtcagg gagcacctac cggctgttac ccagtgctgc cctgacctgg   21600
ttcttcactc tgcacatttg tatcacgcca gaccctggct ggcagctcca ggtgacgagg   21660
catgtcagtg ccttcctgtt ctgttctgtt ttgttttgtt ttttaaatcg ggatgaggcc   21720
ttcctgtgtt gcccaggttg gtcttgaact ctcagggtca agcgaacctt ctgccttggc   21780
ctcataaact gctggattac aggcaggagt caccatacct ggcccactgc tactttctag   21840
atgaagagac agaatcccag agaagaagca ggggtttggc tgctggtctg gagccggttc   21900
tgctcacctc cagcttctgc cttgggccgc cctgttcaca caggagctgc tcacaggctg   21960
agacctcgag cagggccctc ctagaggaac tgggcccccg taagtgccct gagccgcag   22020
gagccggccc tgcgtctcat ccctatctcc ggaggacatt ggctgctagc tcaccagctg   22080
gccccttggc aggcttgaat catgacctgg aacgccagct gtctctggct ctaccctcg   22140
acctgcaccc tgtccaagtg ccccagggcc agactgtttt ggttgcaccc tctggacggg   22200
ctacccccat gatggctgct catggaaagc tgtggttctt agggagctgc caattcctag   22260
tcctgcagcc tggagctcct gggtataagg tgggggctcg ggcgtattgg ggactggggg   22320
tctcaggaaa gagcctgtgg gacctgtgaa ctcatagctg ctggccgagg gaccaccttg   22380
tggctgtcct tctcagctag gcctggtcag ggcttgtgtg cagggcggct gaagctgtgg   22440
gaggccacac tgtccacaca gtgccctgta agcccaccgt gcctcagttt ccccgtctga   22500
caagtggcac aacagaagcc acttcctggc acacagctca gggtcagggc cgacacagca   22560
cttgtgggct gccgggagac ccgagaggct gcccccttcct tgccttggct gccacgggtg   22620
acctggcaaa cccctctggc cgtggcacca ctgggggtct acccttggca gtcagggttg   22680
gccgcttggc tgggagcccc ttctcctccc cagacacatc ctctccttgg ggctggaggg   22740
ggtcctgccg tccccgggat tgtcgagcag caggaatcca ggagggcagt gcctgcagct   22800
cagatggggg ccagtgggca gggccgatcc aagggtggca ggaaagtgcc catcactgac   22860
ctcaggtggg ggaggccatg gtgtgtgaag gaaggagagc tgagtgggga gtcttactt   22920
gtcaccgccc ctctgagtgc ctgctgtgtg caaaggccag cggggccct ttcttcagct   22980
gggctctgcc cagaccctg agctctgggt gggcggggag ggagaccttg ctgctcacag   23040
aggtggctct gcctgaccca gctcccttcc cagggcacag tgggggcata gggtcgggctc   23100
cgtcagacat tccgggacct gcgtccttcc tggggccaca ccctctaccc actgtccccc   23160
acctatttac ctgtatctgc gccagagatg gctgcccaga taagcccctgg ttttcctccct   23220
ttctggagag gctgcgggg ctggcgagga acccacctgc gcagagagtc aggggattgc   23280
tctgtgtgga acgcaggcct cacccatgcc ctggaatctg tcccccttctc tgttgctgag   23340
ggatgagtcc cagatccctg accctgcagg ggagcccagc acagaaaaac tctgaggcct   23400
ccacaccctg gcagcgctgc tggtcgtctg tggggaagga caggcccgtgg gagggagggg   23460
gaggtgcgga gggcagtggg gagggtcagg aggaagtggg ggaagggcca cccaggcccc   23520
gatgtggggg atgtctcacg cgtggggtgg ggcattctca tctctgcttg gtctcctgcc   23580
atgctggggg tcgttcactg cggaccccaa gtaccatgaa gatggggatg ggatgctgag   23640
cagcatcggg gagaacgcaa aggcacctcc cagctcaccc gccccaccc cgcaagcaca   23700
accattgcca tggtgtgggg accggaaggc ggcggctttg ggaccagact gcttctgcct   23760
cgggccgtgc cgctgggcct ttggtcagca ccatcgtgcc ctgcaagtca ctcttagcct   23820
ggtgccctcc tgggcagggc aatgccacaa gagctcagca ccagatgtgc aggtgccact   23880
gttccaccca ccagcaggtc acctgggaa ccctcccctc ctgcagcctc tgtgtgctca   23940
tctgtgaaat gggcgtggtg gagtcacccc tggcttgtgg gagaatccca ggggctgatg   24000
cctgcaggac cctgtgggct ttgccccgct cctgggcag agacagttcc cccagtccca   24060
cccacgtggc tgtgtgcagc aggtgcctgc tgaccctgca ttcctgcaca gtcaccttct   24120
tcacagacgg acccccaccc tgccctgcaa accctccag ggggctgcggg ctgagtgtgt   24180
ccgggaggt gtcctgactc tccacgccaa caggtctgag agcagatggc tgtggcaggt   24240
gcggtgggtg cccagcccac agcagccacc aggcctgcag gaccctgccc cgtgtaggtc   24300
agatgagcca taaaactgag tttcctggac actgagctaa ttaaacctgg acaccgagct   24360
aattaaatgg tccagaagct cctcagtgcc caggctgct ggccgggctc caagtaggtg   24420
aggaacattc cgtttacctc ctgctgcgtc gaaggcgggt ggctccctc gggccctgc   24480
ctgtcccggg ccccctgggt gctgctgcgt caaaggcggg tgtctccgct tgggaccctg   24540
cctgtcctgg gcttcctggg tgctgctgcc tcgaagacgg gtggctcccc tcgggccct   24600
gcctgtcctg cgctccctgg gtcctgctgc cttaaaggcg ggtcgttccc ctcggatccc   24660
tgcctgtctt gagctccctg ggtgctgcct gccctgtgcc cacgtcccac tgttgccttt   24720
ggacaaagct ctcctagggc ctggggttct cccatgagat gacaggggtt ggttcaaagg   24780
tctctgaggt ttttagagct ttgtgaagtg ttctagaatc cattttctct ctcattgctg   24840
gacagagagt atagactggg cttttttcttg agtttctctc aactcttctt tgtccatgag   24900
gcaggaagag gggcttcctc agtcctcagc ttggggtgga ttgggatgga cagagaaccg   24960
tgcaggatcc cagcctgaga cggtccagcg ccccgggtgga gcggagcccg tggctcagcc   25020
gtctgtagcc acgccggggg tcactgtcac tgagggcacg gagccccgc cggcgaggtc   25080
cgaggtgggc gtgtggggtg gtgggcgctg gaggcaggac ctctgcttgt ggagggtggg   25140
ccaggcgtgg accaggtgtc acgtccgctg gggcctttga ggggcaggtg gggattggcg   25200
cggagaagga gtgaagcagc tggggttttg ggagcctgtg cggagcaggc ccggatgcca   25260
gggtggctgg tgaaggtggg cctggccggg ctcggcctcc attgggggag cccccaggt   25320
ccctcccca cacagcttcc ccctctgtct gctgtccaag gctcctgtgc tggcactctg   25380
gggtggtagg ccatgcagcc cgtgtgaacc tccatagacc ttgctgtgaa cgctgcacgg   25440
ggcgtctggg ggcgggctgg cttccccccg tccctgggc caaccttgcc agccttcttc   25500
ttccataaaa gtgggatccg tctgagccct catggcccct ctgggtctgg gtttgctttt   25560
```

```
tgtgctctgc ctggggtcat ggcagggaag gcccagcagg ctcccttgca gagcagggca  25620
gagcagcggc cgccaggagc tgcctgtacc acgtctgctc ttcttcctct cttcctctgc  25680
ccggccccgc ccaccgtcga aagcactagc acgggagtgt ttatcggttt ctcttccaag  25740
ccaaataagg cagagagcgc tcttgcagga gttggagcag gccaggggga gggcagctgg  25800
ggcttggacc aggaccccgg ctccctgtag ctgccctggc ctggcagctg tcatccgcga  25860
actctgatcc tcgcctgccc tcacccggcc cctttcagag cttcccatgc tcagctggta  25920
gcaaaagaag tcaagaccta gcaaggtgcc tgccccggcc aggaggccca ggttctagcc  25980
ctgcagctgc cgctgtgagc tctggggact cagacgactg atgtccttcc cagcttctgt  26040
ttcctttgat gagaggaagg ttggaccaag cgacctgccc tgcttctgtc tgtttcctcc  26100
agtccttttc cttttgacc agttcacttg ttgataactc cagcaacgca tgaaaacatt  26160
cccttgtaa aaaagggaaa tgccgtgggt aggggggacc aaggacctct tctgcaggag  26220
cagacgcaac agcttggtgt ggatcttcct cagccttttt gtccatccta gacatgtgga  26280
atttcagttt tacacaaaag gaatggtagg cgtctgactc tctgtggctt gtatcacttg  26340
gcagtgccac agggattggt gcatgtttgc tctctcatgc tatgtgtcag cgactgttgt  26400
ctctgcgaca atcctgtgag gagggagtta tggttcttga tttatagacg aacaaactaa  26460
gacagaggag attgggctca tctgtggtca tctcagcagt tgtgagaggt cagggccaga  26520
gcccagtggt gtcattctgc agggcacata cagacacgac ccacagggtt ctgccgcacc  26580
ccctgccgct tggcctgctc tgcaggtggg tgccgaggct gttcctgcat ctgctgtgtc  26640
ttgtgagtcc gtgggtgcct gtggagtggg ggcagtgggt ttgcatttcc aagcactgcc  26700
tctgtcatag gctcagggag aagcagttac gcatgagctg ctatgagcca cgggtatgac  26760
tggcatcaca gcaggaggag ccctggggat ggctgagtga cgatgggtgg ggacagagct  26820
cacagaagcc agggttgccc ccaggccagg ccactgctgg ggcaaaggct gggatgcac  26880
acgatgttgg tctgtcaggg agtggcagga agcccacagg gtcagctgac acttaaccca  26940
gagtggtggg agccttgaat gccagactga gggccacaca gttggtctcg gtgcacaagg  27000
acttgggctg agagggctgt tgctcctcaa tggccatctc cttgtgggag agagtccgg   27060
gcagccgctt ccaggaaccc acccatgctt gaaatagtgg gaccacaggg ctgaggaggc  27120
tcctggggat tcctcccagg attcagctgc tctgtcccca accccggagg gcctattcgt  27180
ctagccctat atcctctctg ccagttaggt cagggcagag aagtagaggc acagagggtg  27240
gcggaggggt gtccagccag gccttttctgt ggcaccttct gaggctggct ggagtctgtg  27300
aaatctgtga taactgggcc agaccctcc tgcctcctgg gcatctgct ggagctgagg   27360
ctgctgggg agtctgcctg tgacttgagt ctcttgctgg gccatgctgg gctcagttcg  27420
cctgtctgtg gggtgggatg tgccacccct taggttgttg ggaggaccca aggagagtga  27480
tgcctccagc catggcagct ggcccagctc cggcccgcag cctggctcct tcagggccag  27540
gaacccccag gtcatggact ccaacctctg ggctctcctg cttcccaggt gacgaagctc  27600
caacccatgg gctctccttc ctgggtgtgg aagccctgag gaaggtggag atgggatctc  27660
agtccagccc attggctcca cttccttga gaagctcttt ccccgtctt ggccccccagc   27720
ccttgttcaa gcacctgtcc ctctcctgtc tcctaggccc cgtcagtcct tttgagacc   27780
tgttcccacc cgcccctgct ctcacaggct gccagtgtcc acacactctc aggcactgtc  27840
attggagcct tttaaccaca cgggaaagca ggcaggttag gtaactaccc cccaccccc   27900
cgccagcaac gcccccctgca tacccagggc ctgcaccagg tgctgctgcg ctgccagctc  27960
tctcgaggtc cctcctccta acctcaatgc atcgcgtctt ccagccccg gctccgaggg   28020
ctcagcctcc agtggtcta acctggagtc taaacctgga ttgccatctg cctgcctcag  28080
ccctttcctt ccccagggac cgagggccag tgcggctcca cagccaccca ttttttgttt  28140
gttttgagac ggagtctcgc tctgtcgccc aggctggagt gcagtgtcct gatctcggct  28200
cactgcaagc tccatctcct gggttcacgc cattctcctg cctcagcccc caagtagct   28260
gggactacag gtgccgcca ccacacccgg ctacttttt gtattttag tagagacagg     28320
gtttcaccat gttggccagg atggtctcga tctcctgacc ttctgatctg cccgcctcgg  28380
cctcccaaag tgctgggatt acaggcatga gccactgcac ctggcttgtt tgttttattt   28440
tttattgttt tttgagacgg aatcttgctc tattgcccag gctggagtgc agtgacataa  28500
tctcagctca ctgcaacctc cacctccag gttcaagcga ttctcttgcc tcagcctccc   28560
aagtagctgg gactacagc acccaccacc acacccagat acatttttgta ttttttagtag 28620
agatggggtt tcaccatgtt ggccaggctg gtttcgaact cctgaccatg agatggcggg  28680
cttgagccat cttcccgcct cggcctccca aagtgctggg attacaggcg tgagccacgg  28740
tgcccggccc cagccaccag ttttgtacag cactcaggtg ggtgtggttc ctgaggacat  28800
gtcacacgag atccttccgg tccattagcc caccccgccc catcagtggc cagtgcggcc  28860
attgtggggt ccagagtccc gaggcagaac gactgactcc aggttgtgga ggggcctctt  28920
aggatccttc taggcaccca ggttgggcag gtgcctccat gcctaagact gagctcctgg  28980
tggacatcgg gctgggtgtg ggcgtcctgc acaccctccc tgtggcctgg tgcccgtgag  29040
gagtgggaca g tcaccccgag agcataggcc acccctggagg ctcccagatg gcggccgcag 29100
agcccactt ccctgcctgg tgtgtgatac cttccatgct tgaggacacc tctgactgct  29160
cactcctgtg accctggacc caagtgctgg gccacacctg gactccaggc cccagtcctt  29220
ccttcttctg ctgtcctggc tcctgggtgg ccccgccct cccgctccg aggctctgcc    29280
ctgtgctggg aaccaggaa ttgccacccc ctggcccgg tttctcatgt caggatctgc    29340
tggccaggtt gactcctgag cgccactgtc tcctcagact tgctggtccc accggtccc    29400
cacctgtcca ccgcccgagg ctcctcctgtg aggccgctct gcagctcttg gcctgggggc  29460
ccccggcctc tcatggtgcc ttctgcactg tcccctttgg agatgggagc tttgagggta  29520
ggcgccaccg ttcggtgaaa aggcggtata agcaaagcaa ccccagata ctgaaggagc    29580
cggaaaataa aaggaggcag acagagcaag tgtgttggta cccgcctatt tactggcagg  29640
aacttacaga cggaaacatg gcctcaggca gcctccaggc aggtagagct ctgaacccaa  29700
acgcccgatc tggggctcgt atcgtgccct gggaggaatg tgcaggtggc tgggaacgtg  29760
gcgggtgggg tggccagatt cctgctgcag caccggtttt gtttaggaag aaacgtacga  29820
ggactagaca ctctttttttt tctttcctgc acgtgaatgc cagggagtag gtgctcctgc  29880
aggaagatga tgcatcaacc agccagtctg gaggcattcc gagacccggg gttaatcagc  29940
agattagcat ttaaataaag ttactctgtc cccacagcca gctaggccgg agccacatgg  30000
cggggggcggc ggggggcggct gttcgccgca tcccaggctt gctccatctc ctcgtctgca  30060
atgtggaggt gacagtcgtg gtcctcggct agtgccacag gactgtacgg gacagatcac  30120
ccagccccgt gcctgcactg ggggcggcgg tgacgtgatg gccgcggcgg tgacctgatg  30180
gccgcaggtg tgtccaccct ctggttaggc ctctcctctc cctggggcgc aacaggtgtc  30240
ctcgggtggg aggttcagct gctgggcctg gggcccagc tttcagctcc tgtgcaggcg   30300
```

```
tggagcggga cggcacgccg gggcgttcgt tcacacgatg cccccagctc gtctctgcct   30360
gctctgtgat gcagcctcag ctcctgtggg tcccgggtca cccacccgtg tgggccgcag   30420
tctttctgca ccacgtcctg ctctcggcca gcgctggcct gcgggccccg gcagtgtggg   30480
gtcacacaca ggccgcaccg gctgtttcac ggagccccc  tgctcaaaat cctggccttg   30540
ggtctctgtg tggctcctgg agggagcatg tatgaggtgt ccaggttgtg aaagcccat    30600
ccggcagccc tccctgtgac agtccttcag gcctcgtcag gcttggttca gcccgtgtta   30660
gaggaggcca gacagctcct cctcgatcac cacagggaac gagggttggg cagtttctcc   30720
tctcccaccc gggcgtgggt cagctgcaag ggtctcatcc caggaactgg atcctggcag   30780
gggggctcag gcatctgaca tcccctggca ggtcttccta tgtgccagtg ggagtgggtg   30840
gtgtccagcc ctctttgtgg aatgttccgg ttgagtggtg tgtggtcctg gttaccacca   30900
tgtggcattt gtggctttcc tggccagcac ccactgaaag cagaggccag cccagccctt   30960
ggacacccag gggcccagca gctaccgtgg gggcagcctc tcccctcctg actgtgctcc   31020
tctcagctgt aggatgaagg tctgtggatg ggtgatggct gggctctctg cttcccaagg   31080
agctggatgt gggccatagt caggcgtgtg ctggtgaggc gaggggggttg ggggttggga   31140
accacagctc tctctgaccc catcccattg cagctgactc aggaaaaggc attacccca    31200
cggggtcaca ggcccagcct gggcagctcc tgatgggaac atgggagcca cagggcaggg   31260
caggctcctg tccccgctcc ttggattgtc tcaggcccg  cctccccttt ggctgaattt   31320
cttccttctc tgcctgagcc tgatctgcga agcttccgac ctgccctgag ttggagccag   31380
tcttcagggc caaaagcaat gccgtctcct ccaggcagcc tgctctgaag tctcccctc    31440
tggctttagc ccacaaagtc acagctgagg ccacatcaac acacttagac caagagcact   31500
gccggctgca tagacagcac aggtagatcc aaggagtgtt tcgaaaagcc gtggccctgc   31560
ggccgggatg cccggacctg ggtcctgacc actcttggga gctcctcccc tctcagagcc   31620
catcccatct gaaaatgggg gcattggagc attggaggag tgctcctcac tcctgccctg   31680
ctagccggct actccgagga ccccaagacc agatgatggg agaagtgtg  ggctgggctg   31740
tgaccctgag cccccttctc atcccacccg tgaggctgcc cctgcttggt gtctgtggca   31800
aggctgacag aagatggcgc cagggaccag ccagggcctc cctgtctcag cccgtcctg    31860
ggtgagtggg tgtgctctgg ggtggcagg  tgtgctccgg gggcgggagg tgtgctgcgg   31920
ggggccgggt acgctctggg ggggcgggtg agctctgggg ggctgggtgc gctctggggg   31980
ggctggtgtg ctctggggat ggacaggtgt gctctgggg  gcggggtgtg ctctggggat   32040
ggataggtgt gctctggggg gcggttgtg  ctctgggggg gcagggggtgc tccggggggtg  32100
agtgtgctct gggggcggt  gggtgtgctc tgggggcggt gggtggggctt ggggctaagt    32160
agccctcttc ctctctgagc cttttccttg tctgtgttgt tggtgagtgg ccgccacctg   32220
ggacaagcct tagctgtctg tccaactgtc caccatgtcc ccggaccta  gaccaagccc    32280
gctgcctggt ggggcctgct tggtattgaa tgaatgaatg aatggatgaa tggatgaatg   32340
gatgaatgaa tgagtgaaca aactctgggg gccgtgttgc tgatcacccc agggcaggcc   32400
cgtggtgggt catggtctca ggcagggac  ttgcccgcc  gggtgacgtt ggcctgccgg   32460
ggaacccctg ccaaggtgcc tcccatgccc ccatcgtcct ctgcctttga gtccactctg   32520
ccccctcaag gttccccctg gctcggcag  gggcagggcg gtcagggagg cctcccagctc  32580
cagcccctcc ctcatctcca tcctcagccc ctgcaccgc  ctcatctcca gcccagcc     32640
cttgcagcct caggctcggg cttctgagaa tcctttgcag atttcagggc tggttatttt   32700
tttattctgg caaaatatac atccataaag ctttgtttcc tgagatgatc tcaccctgtc   32760
gcccaggctg gagtgcggca gcgtgatcat ggctcactgc ggcctcagcc tcctgggctc   32820
aagtgatcct cctgctccag cctcctgagt agctgggact acaggcatgc accatcatcc   32880
ccggctaatt tttgaatttt tttgtagaga tggggtctct gtgttgcctg gtctggtctc   32940
gaactcctgg gctcaagtga tccgcctgcc ttggcctccc aaagtgctgg gattacaggc   33000
ctcagccacc acacccggcc taagttttgt cacgttagcc gcattgaagg gcacaggtca   33060
gcagcggtaa gcatgttcgc attgttgtgc agccatcact gacacccatc tctagaactt   33120
cttcgttttc ccaaaggaaa ctgcacgcac ggcaccacct ccctggcctc cccacagcct   33180
cagggtctgg tgaccttcat ccccaggacc tacgcttctg actccaggag ccctgcctgg   33240
tgtccacacc acactaaggt gccctgccac gggcttcgaa cccaaccctg gtgcacttgt   33300
tgagcattga acgttcctgg caggtcagac cgtgagctcc tctgctctga cggatgcatg   33360
gacggctgcc acctggctgg acaggtgcag aggggaggtg ccaccttctc tggggacagg   33420
actgggggcag aactcacccg gctgaaaagt gcagctgtgg agaacttcag aacttcagaa   33480
gcctttgctg tgaatgcatt ttcctcctgc ctcttgggcc agatcttagg gatttttttt   33540
tttttaatg aaaatgtata atcgtcaaaa aactttagat ttaaaagcat ggagccgatg   33600
gctatgcttg gtgcgttaat gggaggaaga gggggatctta acttcaggga gggctcctgg   33660
gggagctggg ggaggctgct gtgtccagca gggcgggcgg tgcccccgg  agcccggcac   33720
tccgcgatgt gtgcgctaag ccgaggccgc cttgagcccg tagcagcgcc gagcgcgatt   33780
ctttcgtgtc tgcttccggg agggtggaag ggtgaagctg ttgagagtgg gaagggaggg   33840
gctgtgcttc ttgagtttgc cgtgtgcccc tgacccttc  aggtgcaagc gtcagctcca   33900
cggtgccaat ggggagatgg gtctggaggc cccaccaggc tgtgaaaggc ccggcctcct   33960
gtgctgtccg tggaggtcgg ggtctccctc tgccctgcgc ctcctctaac ttgccctgcg   34020
ttttccgtgc ccctggtcta gggtgaggct cgggtcttgg ggactgaggg gcaggtgggt   34080
gtcaaggtga gagctgggct gggctgggcc tccctccaga agcttcccg  gggctccttt   34140
ggcaccaagg atggggcaga tggtggcacg catggcctcc cctgggcaca gagccagact   34200
atggagggat ctcgttggct acatcctggc tgggcttgtg gggtcatggt gggagcagca   34260
gccagggtc  tcgcttggac acgggtctga gctcactgtg gcctccttcc tcagcctcct   34320
gaccggggtc ctgaggctgg agggtgggtg gagggtggag ggtgggtgga tagtgggctg   34380
gaggatgggt tgctggcgcc ccttaggcag catgaggcgc ctttccagtc ccagtgtcct   34440
ccctggtagc cccggaaagg ctgagtggtc cctcaggtcc cctgcgagga gacgacatca   34500
ggccccaccc ctcatctcct gacaaacctc acattcctag gaggaagcag gcctggctag   34560
cacgtggcag gcacagcctc cctgactcca gaccttatca gatcagtgca agtgccaggg   34620
agaccccggg tgggagctgt gtggttggga ctgatgcagg cactggccgg actctcagga   34680
tgagggtggg aggccaggcc ccgggacctt ctgggacagg caggagggca gacacgggac   34740
atggtgtggg ggctgtggcg agtgcggcca cgcagagcat ttgggctgaa ggcgcgctgt   34800
gtcccactgc cccatacgtg tgcggggct  ccagacacg  tgctggggc  aggaatcata   34860
gcatttttt  gtttgattgt tttttgagat ggagtctcgc tctgtcgccc aggctggagt   34920
gcagtggctc aatctcggct cactgcaacc tccacctccc gggttcaagc gattctcctg   34980
cctcagcctc ctgagtagct ggaattacag gtgcccgcca ccacacccag ctaatttttg   35040
```

-continued

```
tatttttttg tcaagacagg gattcaccat attggccagg ctggtcttga actcctgacc   35100
tcaggtgatc ctcctgctgc agcctcccaa actgctggga ttacaggcgt gagccaccac   35160
acccagccaa gaatagcatt ttctttcttt ctcttttttga ggcggagtct tgctctgttg   35220
cccaggctga agtgcagtgg tgccatctca gtgtaacctc cgcctcccgg tttcaagcaa   35280
ttcttctgcc tcagcctccc gagtagctgg gattacaggt gcccgccacc atgcccggct   35340
aattttttgta ttttcggtgg agacagggtt tcaccacgtt ggccaggctg gtcttgaact   35400
cctgacctca agtgatccgc ccgccttggc ctcccaaagt gctgggatga caggtgtgaa   35460
ccactgcacc cagcccaaga atagcatttt taaaggaaaa aaagcaaggt agaaagatgg   35520
gtcaaaaccc cagcgccccg ctgggaggct ggtgcccgtg tcgtggcgtg tgtgagatat   35580
gtacggaagc gcgaggcggc ttccacggct ctggctcagg gcagcactca cagggcacac   35640
ggcctcggcg gtgtgacgag ctgggccgtg ggtgcgctgt cctctggggt ggggctggcc   35700
atcctctgtt ggcgacctag ttaacgccca tctccccgca gcctgcctgc tccgcttcag   35760
cggactctcg ctggtctacc tgctcttcct gctgctgctg ccctggttcc ccggccccac   35820
ccgatgcggc ctccaaggta aggccagggg accctgccca cgctctcagg gtggggaggg   35880
gtgggcattc gtttgggggcc aaaattcgta cagctttcct cacctttaac agcccggggt   35940
ggaagatgag gggtcccgaa ataaaatttt tttttttttt tgagacggag tctcgctcag   36000
tcgcccaggc tggagtgcag tggcgcgatc tctgctcact gcaggcttcg cctcccaggt   36060
tcacgccatt ctcctgcctc agcctcccgg gtagctggga ctacaggcgc ccgccaccac   36120
gcctggctta ttttttttttg tatttttagt agagacgggg tttcaccgtg atagccagga   36180
tggtctcgat ctcctgacct tgtgatccgc ccgcctcggc ctcccaaagt gctgggatta   36240
cagacgtgag ccaccgcgcc cggcttttttt ttttttttttt ttttttttga gaccgagtct   36300
cgctctatct cccaggctgg agtgcagtgg cacaatctcg gctcactgca acctccgcat   36360
cccaggttca agtaatcctc gcatcccagc ctcccaagta gctgcaatta caggtgtgag   36420
ccaccacgcc cagccatcaa agtttcttat tttcattgta gacccccaagc taagctcaga   36480
atctttttctg atccgtgttg cagggggctgt gagggggcgag gagggtcatg ggggtggagt   36540
ctctgtgtcc cttgggaggc cacagggggagt ggatgggccc caactgccca ctctctgcag   36600
gctccaggca cgtttcctgc ctgctgaggc tctggcagcc tgggagttcc agccgcctgg   36660
accgccctcc cgctgcccgc tgtgggggttg gacctcagtt gactttgatc cacttgtgcg   36720
gggggggggg ggagctgaga cccccccttgg gaaccacctt ggggtctgag ctgggccagg   36780
actgtgttgc tctcccgtat cctccaaaca gagggcgtg aggccacgtg ccaagcctgc   36840
agcctgggtg acgagggtag cagcaaaccc tccatcctgt gacatgtcac ctacctgccc   36900
tgtgggggcc atgtccattt tgtgcccacg ttttaggaga gcgcgttttg gagcaaacac   36960
tcagagacct gtccccaaag gccatgggcc aaacgtgggt ggggccgggc cctccgctgg   37020
tctttgggtt tggagggtga agagccactg aaaggaagga aggtccccag ggagggcaag   37080
tgtaggcagc aagagacctt cccccagcaga gggcagagg gaggccaagc aggaccaggg   37140
ggcgtgactg tggagacagg ctcttggggtg ccgcccttct gggaggtgct ggacgcatca   37200
ggctggcagc gtcggggcct gtccatggct acgaggtgtc caccgggctg cgttttttcca   37260
ggggactctg ggaggatct gcttcctctt ccagctgctc caggtgccta ccttcctggg   37320
cttgggggctcc ctcccagagcc ggtgggggtgg ggtcaggatc acaccctggg   37380
tctcctgctc cctctcccct gcggtaaccc tgtggcttcg tcccatctgc ctccccggct   37440
aatccaggcc gacttccctg gtttaaggtc agctgttggg cagcccccat ttcctctgct   37500
gcctggactc gcctctgcat gtgagcttct gcgttcacag attctgggga ctgggggtgca   37560
ggcatcattg gggtcccatc ttctgccagc tgcaggtgga aggtcgctct ccggcctcgc   37620
gacatctggc tggaagcatc ccagaggctc ctcctagctc gtggtgctgt ggggtgggca   37680
atggtctttt ttatttattt tttttgagat ggagtctcac tctgtcaccc aggctggagt   37740
gcaatggcac gatctgggct cactgcaacc tccgcctcgc gggttcaagc gattctcccg   37800
cctcggctcc ccgagtagct gggattacag gcgcccaccc tcatgcctga ctaatttttg   37860
tgttttttgta gagacagggg ttttaccatg ttggccaggc tggtcttgaa ctcctgacct   37920
caggtgatct gcccacctcg gccgagacta caggcatgag ctaccgtgct ggctttttt   37980
ttttttttttc gagtggggtg cttgcttggt tgcccaggct ggagagcagt ggcatgatca   38040
tggctcactg cagcctccac ctcctgggct caagcgatcc tcctgcctta gcctaccaaa   38100
gtgctgagat tacaggtgtg agtcactgtg cccagcgcag gcactgatct tggatcatgg   38160
gtagaattca ggggtgcaga gaggcatttt gggagggggcc cagtgcggcc gagtgctggg   38220
agtcgctggg gcccgaggcc caaaccctc caggatgcat ggctggggtg ggtgggcacc   38280
cccactcccg gtccctatcc tgggctcccc cttgtctctg tggagccggt tctgtctgtt   38340
cccaggcccc tggcgtttcg ccgttttgttc cgtaaatatt tcatgcccag ggcgcaattg   38400
gaaacacttt cctttaatca gcagtggggg aaggcaggcg cccagccagg ccaggggagg   38460
agctgggggtg ggaagatttg gagaggaccc gggaggactt ccctgcctga gcctcgtcag   38520
aggcccttca gagacggaga tgctgcccag ttttccggga gggagaagag aaagtgtgag   38580
gcttgcccga gccgagtgcc cggggcttta tgatttgtgc agctgctggg cttggcgtgg   38640
ccctggtgga agctctgacg ccatctgagc cttggtcccc ttgtaggcgt cagcctgatc   38700
cttgggggggc tggaggttga gctcagactg aacaggggagg agaggggtag gggctggggc   38760
tggggcagag ggaacagacc ctggtgctcc aggcagggct gcaggcagag ccacaggggg   38820
tggctcccag agacctgctt gtcatttagg gactcagaag ccccatcctg ccttaggata   38880
aaacccacct ccaagactga ccctgctgtc tggagagaga tcacccccca cctcttacca   38940
tgccccgtgc agggaggccc tgccaccctc tccagcttca ctggtccccc ggctctgcca   39000
gccttgtgta gtctccatcc tctgtctcaa aaggcccctc tcgtgccct acccccgcagc   39060
tcagccctag ctgtcgctgg gtgggcctca tggctcagcc tcaaggcacc ctgggtccct   39120
tggctggtcc catgcacacc ccatggatca ggttccaggg ggctcccatg cacacccccac   39180
ggatcagact cagggcaact ccacactccc cacagaacaa tcaggcccag ccctttgtccg   39240
gcaggtgtgg ggatgtggc tatgaccac gcatcaggat gctgccgtgg tggggcccct   39300
cagcctttgc aggccgtgcc ggggtccaag ggctccggct ctggggagg tccatgctct   39360
gtcaaccatc cggtctgcaa tacccctgggg cctccccgc ccttcctgtt tctcctgag   39420
agcccgtcaa gctgggaggg gagccccggc ccctttttttt ttttttttttt ttgagacgga   39480
gtcttgttct gttgcccagg ctggagtgca gtgcgcgat tcaactcac tgcaacctcc   39540
gcctcctggg tttaagtgaa agtgattctc ctgcctcagc ctcctgagta gctgagatta   39600
caggtgccca tcaccacgcc tggctaattt ttgtattttc agtagaaaca gggtttcacc   39660
atgttggcca ggctggtctc aaactcctga cctgaggtga tccacccacc tcggcctccc   39720
aaaggtgtga accaccacgc caggcccccct gcaccttctt ctgggtgggc aagagccatg   39780
```

-continued

```
ctgagcccct cccctgccat ggataggggt ggcaagaata gtccattccc catgggctcc     39840
ctccggcagg cagcgatgg gttgggggcc acacagtggt tcaggaaagg ctgaagggcg     39900
gttgccggcc agagctgggc gggtccctgg cctgagcctc ctctcactcc ctttcccagg     39960
atggaaaggc cactgtgagc tgggtgtgtc ctgccaggag ggagttggag tcggggcag     40020
gagaccccct gggtctcctg ggctcctgga agaggcagca gtgggtcct gcggaggtgg     40080
cctgatcccc ggctcagcct ggttttccca gctttgcatt tggggtgtgg acctgcaggg     40140
ggagagtgac ggggtgggcg gggacagggg ctgcaggtgg aggcacgaga aagccacccg     40200
accccttgag gtcatgctgt ttgcgtcgga gaagagggcc ggtgtcaggg tgcccctcg     40260
gcctctgtgt gcacctcccc gctcccccgcc ccgtgcaggt cagcagagcc tcgatccctc     40320
tgcacgttcc ggcccctcc catctccagc agcgtctctt cccgggtgc ccctcggact     40380
ctcagctccc tagtctgatc cagcccaggc agggagcggg cgtgccacgt ggccaggagt     40440
ggcctccagg cccagctgcg gcccttccga ccctgcggag ggatcatggc ccagctgttc     40500
taacatggcc agaccaggac actctggccg gcccgagaac tgaaccggga aggaggcagg     40560
gaaaggggag ggaggaagac aatggggaag cagtgacatc cgagatgtag ccagagacgg     40620
acatcctgga ctgtcgtgca gggcaaggcg ggtgggcggg agccaggtgg cctgagagcc     40680
cctccctgcc caggggtctc tggtcaggca gttccttccc gggctgctgg atcgtgtgtg     40740
cagggaaccc gtcagcctgg ctgcccaagg gcccagatgt cctctcagtg cccggggtc     40800
cttgacagcc ccagcaggag cccccacgtg ctgtggggca ggcccccgcag gtccctctct     40860
gtaggactca gaataccttc tccaatgcca cgtgctctcc ctgagtgccc agtgccacag     40920
agggccccgc tggcgaggtt acttcaacgt caggctagag ggtgcagcga gcaggactca     40980
cagcccaggt tccaggcag gtgtggcagg agccccattcc ctgggtcggt gttctcatgt     41040
caccccacgg tgacctgct gtacagaggc ggggggcggc ggccctggc tggtgccctc     41100
ctgctgccag acttgtgctc tgctgaagag gggctggcgc ggcaggtatg agccggcac     41160
ggaggtcgtg agcagtgaga agcctggcac ctatgggttc gggcaggga ggccctggaa     41220
ggtcctgtcc tccgggagcc ctgcacagca ccccctggtg gtggctcctg ttcgtgtcgg     41280
ggctgcacgc tccccttcctg gacggtttttc cattctcct tcccactctc cctgctgctc     41340
accccctccca tcctcacag gtcagaggtc atagctgcag ggtcagcagg tcagggcctg     41400
gggcaaccct aggaaggtgt gagtgtgaga agctggtcca aacctgcctc ggctgcctgg     41460
tggtgcggac agggagtcct gggcatccgt gagggctgct tcacggtcag gcttagggat     41520
gtgcagggtg acttggacgt gggtcatgag tcttttgctcc agaaagaggg ggctgagtgt     41580
ccaaggccaa tcccgagtct gtcacctaac accatttgtg ctcaaaaaac tgaacagagt     41640
ggacacaggc cctgagtttg cgccccgagg ccgagagagg gcagatgtgg tggtgacatt     41700
caccaccttg gacccagacc cagatgctac ctgtccctga gctccaggaa gttgtgagaa     41760
gggcctgagc tgttctgcac tttctcgtgg ccgggcgtgg ctggtggtgc aggagttgct     41820
gccccagggtg gagggccgg aagctcctgc cagcacgtgc cggggtggaa agggaagctg     41880
tccacagccc tgtcaggact cagaaccccgg tgggtcaagg actttggtcc ggaccccgtgc     41940
tgaagggtga gctgtccaca tgtgcgccga gagcagaggt gaagccaggg ctcctgagtg     42000
ccccccagcca cagggtgcgc ccgccagcc cctgccctgc agccgaaggc ctccctgctg     42060
ggggctgag tccagtgggg ccacaggcag ctgggagcag gacaaggctg ccaggcaacc     42120
agatggtgct gccgcttcct gccaggtgtg ggtgcacaga gagagagagg atgccggtct     42180
ggggcctgac ctggtgcaca gcaggtgcct gaaatgccag ggtggccatg gggactgggt     42240
accatgcata ggcatgcat cgggatgcaa cttctccttg cagcccctca gccccaggga     42300
ggcagctgcc tgccccactt ttctccagag ccatcatggc cctgctccca cccagccag     42360
ggctgctcag gggcgctccg catgctctgg tctccatcca cctgcagccc ccactggggt     42420
gaggtggagc ttcttgcctc tccttgtgtc tatttcctct gcttccacaa ctgaacggtg     42480
acaggtattt gctggatgag ggagcacacc ccaggtggtt tcctctgagc ctgggaggcc     42540
ttttcctgcc tgtgggcccc aggccccatcc tgctgccacc cccaggagga tgcccggctc     42600
cttgtgacaa gagtgacccct cgggaggcgt gggggagtggg gctggccggc ctgcctgatg     42660
gggtcctgag tccatggcgg gttttgcatct caggcctctg ggctctggcc gggctggggg     42720
ctattgtccg gctgagcggc ctgggctgcg gcccctcccc gtcccggga ccagcctcac     42780
ccactcgctc tgccgcaggt cacacaggcc gcctcctgga ggcattgctg ggcctcaggc     42840
tgctcttcct ggtggcccat ctcgccctcc agatctgcct gcatattgtg cccgcctgg     42900
accagctcct gggacccagc tgtgagtcgc tgaggggcg gggtaggat agccatcctg     42960
ggggtcaggg agagggccct gcagtgaccc cgagtctcct ggggggggttg actcagcctg     43020
atttatgtct ggctggatg gtccaggtga aacgctccag ggatgaccag gccacggtgc     43080
tggctgggca gagcctgacc tgggttccce cgtctttctc tgcaggcagc cgctgggaga     43140
ccctctcgcg acacataggg gtcacaaggt aagaccattc ctcccacccc caaccagcaa     43200
gcctcccttg gggatttcag gccccaggaa gtgggggagc ccaggaggga cagaggggga     43260
cctggagact catccacact cccacccaca cctggagacc catccacgct cccacccaca     43320
cctggagacc catccacact ctcacccgca cctggagacc catccacact cccacccgca     43380
cctggagacc catccacact cccacccgca cctggagacc catccacact cccacccgca     43440
cctggagacc catccacact cccacccgca cctggagacc catccacact cccacccgca     43500
cctggagacc catccacact cccacccgca cctggagacc catccacact cacacccaca     43560
cctgtcctct tggtctgacc gcggctgctc cctgctctcc caggctgga cctgaaggac     43620
atccccaacg ccatccggct ggtggcccct gacctgggca tcttggtggt ctcctctgtc     43680
tgcctcggca tctgcgggcg ccttgcaagg aacacccggc agagcccaca tccacggag     43740
ctggtgaggg cagctgcgtc acccgtgtgt cagggaggtc attcgagagc tgtggtctca     43800
gccattttga gggttatttt aatctttta aaacagatgt agacgtttg gttgtaagtt     43860
ggtgttaaag agaggaggaa gttccaaatc ccaccccggg gcccagcctg cagttccatc     43920
cgttcagacc tgttttctact cgggctctgc ctcagtcag aaacctccac gccccgacat     43980
ggcatctgtg cccttaggaa ctcttcacag gggaattatt tggggccacg cggtggtgga     44040
aacctgcagt gctgggcagt gggtctggct ggagagccac tgcagaaggg ctgagaaggg     44100
gcggcccag caggcccat gcacttacag gcaaacaggc tgtcggccca gagccccagc     44160
aggggcctgg aacccaggag cgacgggcct gaagcaggga ctctgtcctc ggagtgggag     44220
gcagagtgaa ctttagctgc tacaagactt ggaggtccgg cccgggaat ctctgagcta     44280
tggcccctc acacggacag gcatgagct gggcctgcg acaccccaacg ttgactgctc     44340
agaccctctc gtccctgcct gggcccacac ttgccatccc caggctcagc caggattat     44400
ggccacctgg gtgtcctggc ccacgaactc cctgccccgg gcacccagcc tcctcccacc     44460
tcaccctccc agtgcccact cgtcagatag ctgatgctcg ccacgcacat gggcctcaac     44520
```

```
ttctagagga gtcccgagag ggaaaggggt tccccaagcc acacggtagg tcgagtacac   44580
ctgctcagcc tgcagaggcg gcctgccctc ctgcctgtcc tgtcgccacc ccatggggca   44640
aggctggtgc ccgcatttca gaagtgggaa cggggacctg gaggtcaagt ggcttttccg   44700
ggcatttgag ggggtccagc gctcatgagg actgtgctgc tgcctgtcct ccaagagacc   44760
cgccctccc tcgtcagccc ctccatgctg atgggggcat ggggcatgag cttcctagag   44820
tttggctgct gggaagggc tgggtggctg gactctggtc atcttcatct tggtgtgatg   44880
ggagcctgag tgtgcagctg cgccctgggc ggcagcgtg gacagacttc agagtgagct   44940
gggggcacca ggcacctgca ggataccgtt ccgaaagatc tagaagcccc atgacccggc   45000
ctggcagggc cccggggcga ccctcactcc cacatatggg caacacacac acgtgtttgc   45060
aggcatgcga cggagtgtgc cagccagccc gagggggtgct ggccgctaga ggagggtgag   45120
gggcgtctgc agcatggctg cggcacgtgg ggccaagtc agggccgggc ctgcccctcg   45180
gtggcctcac accccaagtc agggccgggc ctgcccctcg tggcctcat accccaagtc   45240
agggccgggc ctgcccctcg tggcctcac acctgttctc tcacagcagc tgcctctgtt   45300
ctttccactc ccagaaatgc tcattttca cggctctgct cagaagattt cccagggcca   45360
gggccagggc caggctgtgg gtggggtgag cgatgcgcc ctgcgttctg atccagcctc   45420
gcccccagct gctgtgtggt ctctgagagg ggtgggctca gggcctgggc ctctcctgcc   45480
ctgatctccc tgttaccctg gcctcggagc ctcccagcag ccctgcagc cctggaggcc   45540
tgtgaggaca ggactggtct ggttcatctg tcccgtcaag cccccatccc atttgacaga   45600
aggggaatag gctccgagag gctgtgactt gcctcggcct gcagagcacg gagactgtca   45660
gagctgggt ggggcctatc gtccagcccc acagctgcg gtctcagccc gggcacctgg   45720
cgcctcagcc accaggagag cccccgagtc acagatgggg acactgggcc ggtggcagcc   45780
aggccagac cagggcatct gacgacagcc gtgttctttc caccacacct ggctttccct   45840
ggtgttggg aaatggctgt gttctgggaa atctttagtc aggtccaggg aaaacaggcc   45900
cggcaggtct ctctccccag ccccaggccg gcctgtcact tcttctaggc agctggccac   45960
ctctgtcccc ccagaggctt ggggagggca ggagtaccac ccctatcttc caggcagagc   46020
cacccagaag gctggcaggg gtacacagga gaccctgagg cctggccatg tccctcaggc   46080
cccttggtc tctagagacc cccgggggta tagacagggc cccgctgctc cctgggtgcg   46140
tggttcgggg agatgaggtg gtataggaca gtctgtggtc tgtctgtacc tgcaaggtc   46200
atcacgtgcc tgggcttggc aggacagacc ctgggtcttc ggccagggtg ggagctgcta   46260
ccaggaggc ctgcaggaac tgtgagcttg agtgaggaag taggaaggtg tcaggcagac   46320
ctcagggacg gctggggcct gtgcccgggg aggctgtcct gtggccctca gaggagcagc   46380
tgtggatgtg gccgcctccc acgctcctgg ctgggcaggt gtgggctgga gaggtggcgt   46440
cagtgcgata cacctgacct tgcccctgtc cgtgaccttg gcaggatgat gatgagaggg   46500
atgtggatgc cagcccgacg gcagggctgc aggaagcagc aacgctgggc cctacacgga   46560
ggtcacggct ggccgctcgt ttccgagtca cggcccactg gctgctggtg gcggctgagg   46620
gggtcctggc cgtaacactg cttgcactgg caggtacgca ccgaggcagg gggcactggc   46680
agtcacactg ggagggtct tgggagttcc ctgatgactg tggagacagc gggacacatg   46740
gcactggcca ggtaccaccc tgtgtgcccc tgccccgcag gcatcgccca cccctcggcc   46800
ctctccagtg tctacctgct gctcttcctg gccctctgcc cctggtgggc ctgccactt   46860
cccatcagca ctcggggctt cagcagactc tgcgtcgcgg tggggtgctt cggcgccggc   46920
catctcatct gcctctactg ctaccagatg cccttggcac aggctctgct cccgcctgcc   46980
ggcatctggg ctaggtaacg gcttgccaca cagccccttt ttcctgccac cctggtcccg   47040
cccacctggc tcgtctagcc cctgtggccc cactgcctct ggggtggtag gctgtgacgg   47100
gtcttctctg gacagggtgc tgggtctcaa ggacttcgtg ggtcccacca actgctccaa   47160
cccccacgcg ctggtcctca acaccggcct ggactggcct gtgtatgcca gcccggcgt   47220
cctcctgctg ctgtgctacg ccacggcctc tctgcgcaag ctccgcgcgt accgccctc   47280
cggcagggtg agcacctgcc acccatgtg ggtgggctga ggcaggcca tggggctggt   47340
ctcaggacct cctgcctctg ggtggggtgt ggagctggtt tgggctcaag acgctggtct   47400
ctgcagagga aggaggcggc aaagggggtat gaggctcggg agctggagct agcagagctg   47460
gaccagtggc cccaggaacg ggagtctgac caggtgagca gccaggcagg tggagacgcc   47520
agcgtgggg gcgcccggcc agcccgtgca tggctcaggc ctgcttgccc acagcacgtg   47580
gtgcccacag caccccgacac cgaggctgat aactgcatcg tgcacgagct gaccggccag   47640
agctccgtcc tgcggcggcc tggtgagtac cgcacactgc aaggtatggc tgggtgcggg   47700
gggcggggcg gaggccggtg ctgccccctg gtggccgcct ggcgctctcg catgctcgcg   47760
ccgcacctct gcctgccgcc cctcgggg ccaggacat ccacgggtcg gtgtcagtga   47820
cccccgagac ccccagggca gccgagtggc catgtcactg accaaccccc aagaccccca   47880
gggcagctga gtgccgcgt cgttgatccc caagacccca tggggggcct ccaggtcccc   47940
caaccctcc ccagagaatg tggctatgct gtcttgtgct gttagctctg ggagctgctc   48000
caggtggccc agtggcccca ggaggccgct cgtccagggc aggggctggc ctgggaactc   48060
tgtgttggcc acgtcgcctt gggagggcct tctggctact ttcttttcttt   48120
accctaaccc ttgatttttcc attttgcaat gtgttctga atgaagcaaa tgaagccacg   48180
gccctggggt ggggtcctg agagtcttca ggtgcgcaga gctggaaagg gggtcagggc   48240
caccttttcccc acccttttcaa ggaaagtgag gcccagaaa cggcaggtgc tggcagggc   48300
atccctgacg ctcaggacg gtgtcagccc aattgccgga gcctcgtgt tctgcccata   48360
gcccaccggg ggcctgtctc tcctgctgtg tgcttcccca gggccagat tttagggcat   48420
agtcaggtg ggaggcctg cagatcaacc tgccgaagct gaccgctgtc cccacctgca   48480
gtgcggccca agcgggctga gcccaggag gcgtctccgc tccacagcct gggccacctc   48540
atcatggacc agagctatgt gtgcgcgctc attgccatga tggtaggcgg ctgtggggt   48600
tggggtgggg gccccctct gccgcgcagg tgtggggcat cgcctgggtg ggggtgcgct   48660
ggcagctgtg cagcccccctc tgccgcgcag gtgtgggga tcgcctgggt ggggtgcgcg   48720
gggcagctgt gcagccccct ctgccgcgca ggtgtgggga atcgcctggg tggggtgcgc   48780
tgggcagctg tgcagccctc tctgccgcgc aggtatggaa catcacctac cacagctggc   48840
tgaccttcgt actgctgctc tgggcctgcc tcatctggac ggtgcgcagc cgccaccaac   48900
tggccatgct gtgctgcccc tgcatcctgc tgtatgggat ggctgtgcgc tgcctacgct   48960
acgtgtgggc catggacctg cgccctgagc tgcccaccac cctggggccc gtcagcctgc   49020
gccagctggg gctggagcac acccgctacc cctgtctgga cccttggtgcc atggtgagtg   49080
tgcaccacca catccggggg tgcctgggtg cgcagaccca tcaggttgt cgtcctgttc   49140
aatgtccact tgcccggggg agtggcagcg ccaagaaggc agatgtgtct gtctgtcccc   49200
ttctgcccac ccagagccag cccagagtag cttctcagtg agcgtttgtt gactgaataa   49260
```

```
acagacaacc ttgtgttggc acgggcacca cccctgtgcc ctgacactgt gtgagcgtgg   49320
gctctgttgg cacgggcacc acccctgtgc cccgacactg tgtgtgagca tgggctatgc   49380
ccattggcac aggcaccacc cctgcgcccc tgacagtgtg tgtgagcgtg ggctctgccc   49440
attggcacca tgcacagccc tgggtctcag tgacaagctg tgcaggccat gtgttcacag   49500
ggtgcctgcg tgtccatgtg aaacgggtgc cagcatcgtg tctggacacc tgtttgcagg   49560
ccagtgggtc tcatcttgtg aaacttgtga gcctgtgtgc caacatatgc acctgtgagc   49620
ttgtgtgcat atgtgagcac gcatgtgggc aaacatgcac tccagcatgc ggacatgtgt   49680
gcaggtgcgt gcatggatct gtgcccacgt gaactagtga acccgtgtgt gactctgcgt   49740
gtgagcgcaa gtgaacccat gcactcatcc atggatgtga gagtgtgtgc tcgtgtgcct   49800
ctgagtgggt gtgagcgaga gggtgttcgg tgcctgtggg gaggctgcgg tggatgggct   49860
ggtgccagcc gcctgagagc tcttgccccc tgctatagga gggtgctggg tccccggct   49920
gtgggagggg tgctgggccc cccggctgac tgtgacaccc tgcgcttgtc acagttgctc   49980
tacacctga ccttctggct cctgctgcgc cagtttgtga aagagaagct gctgaagtgg   50040
gcagagtctc cagctgcgct gacggaggtc accgtgacag acacaggtga gtggtgggcc   50100
agaggcgggg gttgccctcc tgcctgcccg ccctgatgcc atcgcctgcc cctggcttgg   50160
cccacagagc ccacgcggac gcagacgctg ttgcagagcc tgggggagct ggtgaagggc   50220
gtgtacgcca agtactggat ctatgtgtgt gctggcatgt tcatcgtggt cagcttcgcc   50280
ggccgcctcg tggtctacaa gattgtctac atgttcctct tcctgctctg cctcaccctc   50340
ttccaggtgg ctgggggggcc gggatggggg ctggggcacg gaccctcccc gcggtcctca   50400
ccaccccac ctcacccggc aggtctacta cagcctgtgg cggaagctgc tcaaggcctt   50460
ctggtggctc gtggtggcct acaccatgct ggtcctcatc gccgtctaca ccttccagtt   50520
ccaggacttc cctgcctact ggcgcaacct cactggcttc accgacgagc agtgagtcca   50580
ggctggggcg gtggggcagg ggcgccgaaa ccccgtgcac ttccccgggg ctgcagcggc   50640
tctgccgggg gccgggccgg tgctgatgct gcccctccac aggctggggg acctgggcct   50700
ggagcagttc agcgtgtccg agctcttctc cagcatcctg gtgcccggct tcttcctcct   50760
ggcctgcatc ctgcagctgc actacttcca caggcccttc atgcagctca ccgacatgga   50820
gcacgtgtcc ctgcctgca cgcgcctccc cgcgtgggct cacaggtgcg gccccgccct   50880
ccctgtccgg ccctgagagg gtgtagcctc ctgggccagg gagggagcca ggtgggagtt   50940
ggacaggagc cacatcttcc accttcagat cccaaggggc atttgctcat accaagggga   51000
tggcaggcag gtgaggtca cagggacagt gggcatgagt tgcgacacag ctgtgcacct   51060
gaactggcag ctgcagcaga agcggtgccg acagggcttc ttccagcccc aggaaatgag   51120
gggcaggaac ccagttggga gatgacattt tcggaccctc tcccaggcag gatgcagtga   51180
gtgggacccc actgctgcgg gaggagcagc aggagcatca gcagcagcag caggaggagg   51240
aggaggagga ggaggactcc agggacgagg ggctgggcgt ggccactccc caccaggcca   51300
cgcaggtgcc tgaaggtggg ttgggcgggc agagcacagc tgccacccag tctgctgtg   51360
catgtcccag ctcggggggc gttggcagag tcccctctgg gctccagagc ctcttcctca   51420
caggggaccc gggaatcccc gtttgtgccc cgcactgacc ctcacaccat cacagggca   51480
gccaagtggg gcctggtggc tgagcggctg ctggagctgg cagccggctt ctcggacgtc   51540
ctctcacgcg tgcaggtgtt cctgcagtcgcg gctgtgagcc ttcacgtttt caagctggtg   51600
gccctgtaca ccgtctgggt ggccctgaag gaggtgagtg tggcaggcaa ctcagcttcc   51660
catctggggt ggggtcgctc tggcctgccc agctggcctc cccaagccca gccccacgtg   51720
cccactgccc tccccaagcc cagccccacg tgccactgc cctcaggtgt cggtgatgaa   51780
cctgctgctg gtggtgctgt gggcctctgc cctgccctac ccacgcttcc ggcccatggc   51840
ctcctgcctg tccaccgtgt ggacctgcgt catcatcgtg tgtaagatgc tgtaccagct   51900
caaggttgtc aaccccccagg agtattccag caactgcacc gaggtaccgg cccccgaggg   51960
ctgggacggg aggaagctcc aggcaactct gtattcgcag cccgaccctc ctggggcagc   52020
tgcctcagtg cagtggggcc agcaatggag atggagcagt ctcccctggg ggcgccaagg   52080
gggcttcctg gaggcagcat ccttcgacct caactgtgga ccaggggcgc actcctgca   52140
cacaagggtg tccagtaggg gcggagtccc agggtctccg gcagtgagga cgggagggcc   52200
ccaccctg acagggagag acagtcaggc atctctgcct gggaccttct cgcacatccc   52260
tccttctccc tggaccttct ttcactcccc cagccccctcc ccgtggtctc cctgttttctc   52320
aaacacctgg tccccttccc cgtgaaggtg gctccaaggc tggcagcccc cgtgtccctg   52380
gctggggagc agtggacctg ccccagagct gtggctgtgg tgggctccgg gcagggccag   52440
ggggcactgt ggcctgggag gggggcactga tgcctggcct cttgccagcc cttccccaac   52500
agcaccact tgctgcccac ggagatcaac cagtccctgc tgtaccggtg gcccgtggac   52560
cctgccaact ggtttggggt gcggaaaggg ttccccaacc tgggctacat ccaggtgagt   52620
tgaagggctg gtgggcggct gggcgggcga taccccggct gcccctgac ccttgccctc   52680
cgcagaacca cctgcaagtg ctgctgctgc tggtattcga ggccatcgtg taccggcgcc   52740
aggagcacta cgccggcag caccgactgg ccccaggtgc tgcccaggcc gtgtttgcca   52800
gcggcacccg ccagccgctg gaccaggatc tgctcggctg cctcaagtac ttcatcaact   52860
tcttcttcta caattcgggg ctggaggtga ggcaaggaca ttgcctcccc ctggggcagg   52920
gcttggcctt cggggagggag ggacggctgc accgtcgagg caccgcaagc ctggcccac   52980
ctgggtttgc ctgggccaca gagggtgggg gactcagggc caggcacggc ttccctggac   53040
tcctgtgtg tgtcggtgct gacaacaggc aggggccaa gttagatctg ctctactgta   53100
cagcccacct cctggagcct cagttcccc tgcacgatgt caactgccag ccactcctgc   53160
cctcttgaca gcgccgctgg ccctgtcctt gcttgatgcc cgcagcctcc aggcagggct   53220
gctgcaagcc tgaggcctgc tgggtgggac aagaaagtcc ctcccccag actcagtgca   53280
tcccacacc ccgccctctc ccctcccccag atctgcttcc tgatgccgt gaacgtgatc   53340
gggcagcgca tgaactttct ggtgacccctg cacggttgct ggctggtggc catcctcacc   53400
cgcaggcacc gccaggccat tgcccgcctc tggcccaact actgcctctt cctggcgctg   53460
ttcctgctgt accagtacct gctgtgcctg ggatgccccc cggccctgtg cattggtgag   53520
gggcacgtgc cttgggtggg agtgggcttt gtggctttgt ggatgccgt gggggtgttt   53580
cccgcctgcc ccagactcct gtccacctc ctagactag ccttgcctc ctccagtccc   53640
tcctctctgc tccacatcct acccaggcgc catcacctgc atcctgtctc tcgggggcag   53700
cctggccccc tccaggctct gctgttctct tttcctttttt tgcccagtat tctatcttga   53760
aatatttcaa accttcagga aagttgtgag tcacacaagg agcactgcgt cctctccggg   53820
cccgtgcgg gtcggccgtg atgcctcaca cccaagtgct gcctcgagca tgcgtctcct   53880
gggtgagggt gtctgagccc acagcccac acccgtggtc ccgtcctg gcagtgccat   53940
cgtcaaacgt gtcctctgca ttcaaacagc cccggcctca gcaccttct ttgtggccat   54000
```

```
ttggttttca gacgggatct ggtctgatgt ttgctctagt ctcttgtctt gggtctaagc    54060
cgccccgcc  tctcctgtct cttgggaagt tccggaggga ggccggtagc gttgctgacg     54120
ccgtgagact ggatttgcgt ggctgtcctg gtgctgcagg tctgctcaag gcacacagca    54180
ccctgcggtc tgagatgggg agtcacattt gtgcacgtgg ccggctcagg ggcgtcccac    54240
ctgccccaca gtggcaccca gcctgttggc actggtgggc tgtgtggggt cagccttgtg    54300
gttttacgaa acagactttc tctctgctgt ctctgtgtgt ctgtcagctg ggattcccat    54360
caaggacagc tgccatttgt tactggctgc ttttccaagaa ttctgtcatc cgcagaccct   54420
gggcctcccc tctgctgagt gggtcctggc ccctccggcc acacactgtt acatcatctc    54480
cccgtatttg gctgggcatg gtggttcacg cctgtgatgc cagcactttg ggaggctgag    54540
gcaggagcat cccttgaggc caggagtttg aaaccactct ggtcaacata gcaagaaccc    54600
tttttttttt tttttttttt tttgagatgg agtcttgctc tgtcacccag gctggagtac    54660
actggcacaa tctcggctca ctgcagcctc cgcctcccgg gttcaagcaa ttctcctgtc    54720
tcagcctccc tcgtggctag gattacaggc aagcaccacc aggcccggct aatttttgta    54780
ttttagtag  agacggggtt tcaccatctt ggccaggctg gtcttgaact cctgacctca    54840
ggtgatccac ccgcctccca aattacaggc ctccctcctg ggattacagg cgtgagctgc    54900
cacgcccggc cccgtcttgt tttctgctcc caggcgctgc tgcctcatct tctgctaccc    54960
aggcccagcc ttgtgctcac agccattgct ccagggagcc caatcgagtt ctaggagcgt    55020
gaggtttaga gcccgggggtc tgggcgctgg gtgtgcctgt tgctacaggg ctgcctcagc   55080
ctctgggccc tccagctctt ccttgttgaa acatctgctt tcgagcatca ccgaggccag    55140
ctccccgtct cctgtccacc tcttccttgt tgaaatacct gctatcaagc gtcacctagg    55200
ccagctcccc ttcttctgcc tccttccacg cggctgcgcc atgcagtcgc catcctgtga    55260
gatcagcatg tcctgggttc cccaacatcg agggtaactt tgttttttgta tcgtgaggtt   55320
ccctctgtgg cagatggggc tgtgggttca gcatgtcctg ggttcccag  catcgagggt    55380
cactttgttt ttgggtcgcg aggttccctc tgtggcagat ggggctgtgg gttcagcatg    55440
tcctgggttc cccagcatcg agggtcactt tgttttttgtg tcgcgaggtt ccctctgtgg   55500
cagatggggc tgtgggttca gcatgtcctg ggttcccag  catcgagggt cactttgttt    55560
ttgggtcgcg aggttccctc tgtggcagat ggggctgtgg ggttcagaat gtcctgggtt    55620
ccccagcatc gagggtcact ttgttttttgg gtcacgaggt tccctctgtg gcagatgggg   55680
ctgtgggttc agcatgtcct gggttcccca gcatcgaggg tcactttgtt tttgtgtcgc    55740
gaggttccct ctgtggcaga tggggctgtg agatcagcat gtcctgggtt ccccaacatc    55800
gagggtcact ttgttttttgg gtcgcgaggt tccctctgtg gcagatgggg ctgtgggttc   55860
agcatgtcct gggttcccca gcatcgaggg tcactttgtt tttgggtcgc gaggttccct    55920
ctgtggcaga tggggctgtg ggtcagcat gtcctgggtt ccccagcatc gagggtcact     55980
ttgttttttgg gtcgcgaggt tccctctgtg gcagatgggg ctgtgggttc agaatgtcct   56040
gggttcccca gcatcgaggg tcactttgtt tttgggtcgc gaggttccct ctgtggcaga    56100
tggggctgtg ggtcagcat gtcctgggtt ccccagcatc gagggtcact ttgttttttgg    56160
gtcacgaggt tccctctgtg gcagatgggg ctgtgggttc agcatgtcct gggttcccca    56220
acatcgaggg tcactttgtt tttgggtcgc gaggttccct ctgtggcaga tggggctgtg    56280
agttcagcat gtcctgggtt ccccagcatg gagggtcact ttgttttttgt gtcgcaaggt   56340
tccctctgtg gcagatgggg ctgtgagttc agcatgtcct gggttcccca gcatggaggg    56400
tcactttgtt tttgtgtcgc gaggttccct ctgtggcaga tggggctgtg agttcagcat    56460
gtcctgggtt ccccagcatg gagggtcact ttgttttttgt gtcgcgaggt tccctctgtg   56520
gcagatgggg ctgtgagttc agaatgtcct gggttcccca gcatcgaggg tcactttgtt    56580
tttgtgtcgc gaggttccct ctgtggcaga tggggctgtg agatcagcat gtcctgggtt    56640
ccccaacatc gagggtcact ttgttttttgg gtcgcgaggt tccctctgtg gcagatgggg   56700
ctgtgggttc agcatgtcct gggttcccca gcatcgaggg tcactttgct tttgggtcgc    56760
gaggttccct ctgtggcaga tggggctgtg agttcagcat gtcctgggtt ccccagcatg    56820
gagggtcact ttgtttttgt gtcgcgaggt tccctctgtg gcagatgggg ctgtgggttt    56880
cgcagatgcg tggagtcaca tccatgccct cagtccttag ggaccgaccc tccctgcctc    56940
acacgcctcc caggaagtgt ggccggggc  cggcagtgcc acggctccct ccccagcagg    57000
ccccgccgc  tcccatcccc agcacgtggt cctatcagaa cgccacgtca gcaggactcc    57060
cagcaggtgg cctttaggtc tggcttcttt cacttggcag agcacactga ggtctgtcta    57120
ggctgtcgca tggatcccgg tcccacgtgc tgagcagcgc gttcccagct gtggttgctg    57180
caggttgaac ttttcctggc tgcaggcgtc cgtgcagctt ctggccgttg ttttcagagc    57240
tgtcctatca cacgcactgt cctatcatgg aaatatgacc cgtgtgggcc acaactcagg    57300
cccagcagcc cccaccccg  tgctctctgg cctcctgctc agttcctttg ccccagggg    57360
cttggtgcag agttgaagga atctgtgtgt gtgaacacac aggacactag agctgtcagt    57420
tctcgagaca ccaggtgtgc gcgaggtgat tccatggac  cctgagggct ggtgatagac    57480
tcgggtcaac gggtggggac cgggtgtctc aggcccagg  caggcccggc ccttcctgac    57540
atgacacccc ttcccccaga ttatccctgg cgctggaggc gggccgtccc catgaactcc    57600
gcactcatca agtggctgta cctgcctgat ttcttccggg ccccccaactc caccaacctc    57660
atcagtgagt gccccccacc accccgcct  ctgcagagga ccctcagagt acattcacgc    57720
ccccaaatct gctcacaagt gtgcacacag gcgtgcacgg gcggaggtgt ggtcaggcac    57780
atggcgcct  caggccctg  acctcgcacg cacgcacga  gacctcagcc tgtgtgcagg    57840
gcagcccttg tgcagatgcc ctcacaccgg ggctccccca gggacacccg gccactcacc    57900
caggcagacg tgtgtccgct cccagcgcct gcacgccgac aggcctgggg tgggaggtgg    57960
gatttatgcg ccgtgcccac ctcgtgtggg tcccgtgtg  gcacagcggc ggctcctgtg    58020
tcctgcaggc gactttctcc tgctgctgtg cgcctcccag cagtggcagg tgttctcagc    58080
tgagcgcaca gaggagtggc agcgcatggc tggcgtcaac accgaccgcc tggagccgtc    58140
gcggggggag cccaaccccg tgcccaactt tatccactgc aggtggggttc cacgtcaccc    58200
tccacgggga accttctggg aggggtggcc gggcgcccg  ccctgacgct ccggcctggc    58260
aggtcctacc ttgacatgct gaaggtgcc  gtcttccgat acctgttctg gctggtgctg    58320
gtggtggtgt ttgtcacggg ggccacccgc atcagcatct tcgggctggg ctacctgctg    58380
gcctggcgct acctgctgct cttcggcacg gccctgctgc agaggggaca acgggcccgc    58440
ctcgtgctgt gggactgcct cattctgtac aacgtcaccg tcatcatctc caagaacatg    58500
ctgtcggtga gcctccggcc ccccgcacc  caccgccctg ggcccgct   ggccccgctg    58560
accctgctct ccccagctc  ctggcctgcg tcttcgtgga gcagatgcag accggcttct    58620
gctgggtcat ccagctcttc agccttgtat gcaccgtcaa gggctactat gaccgtgagt    58680
ggccaggacg gtggcgggg  agggcgtggg gaagcccct  gctcctgggc cctgggcctg    58740
```

-continued

```
acccttgccg gtgcctgcct tgcagccaag gagatgatgg acagagacca ggactgcctg   58800
ctgcctgtgg aggaggctgg catcatctgg gacagcgtct gcttcttctt cctgctgctg   58860
cagcgccgcg tcttccttag ccattactac ctgcacgtca gggccgacct ccaggccacc   58920
gccctgctag cctccaggca agcttgggcc cagacacagc ccagagctcc cgtcttgggg   58980
ctgggagggg gcaatgggag gttcctcact gtctcagccc ccggcccgtg gagggcaggc   59040
tctgccactc tgtgacatgg gcgtgtcatc tagagggaga atgaaggccg gcagatcccc   59100
ggcaccatca cactctgccc cagtgctggg tctgtcagag accacaggct gcagtgctga   59160
cggtggctgg tgtctcaccc ccagccaact ttcccactaa gggctaagtt tctccaccag   59220
cgggagggcc actgtgtggt gtcacgactg ccccagggag gggttctggc ttgggggcag   59280
cttttgccttc ttccctgcag ctgtggtggg gtgggtgcca ccagacgccc ctgcatctgt   59340
acggcagaag ggcctgtcct cgccgcagac agcacggagg gtgggggcag cagatgcctc   59400
ccccgtgggt gcctcttgtc cagcgtgggc agagaggagc aggctgagct gtcccgggct   59460
gagcggggag cggcggctgc ccatgttgct ggggtcgagt gctggtgct cacaccccat    59520
ccccgcctcc ctacaggggc ttcgccctct acaacgctgc caacctcaag agcattgact   59580
ttcaccgcag gatagaggag aagtccctgg cccagctgaa aagacagtag gtgcctctgg   59640
ggcgggggact ccccggctcc tcccccaat gctcagcata ccccaccttt ccccaccaca    59700
ggatggagcg tatccgtgcc aagcaggaga agcacaggca gggccgggtg gaccgcagtc   59760
gcccccagga caccctgggc cccaaggacc ccggcctgga gccaggtgag tgcagctgga   59820
gtcgggcacc cagggccccg tgtccagcat gtctgtgcct gctggcgtgt gctgcgtctg   59880
tgcccatgtg acgtcccaca gggctcccag cccgcctgtc ctgtccgcat gatcaccctc   59940
tgtctggcag gccccatggc cgccctgtga ctgtccgtcc acgcacatgg gctctgagcc   60000
ccatggcccc acacggcccc tgtcactgtg ggtgtccgtg tctgtctcca cctatcctgt   60060
ctccaagacg ggagcactca cagccccgac ccctcctggt ggcttgactg ctgcctcatg   60120
ctcaccctgc ccctccacag ggcccgacag tccaggggc tcctccccgc cacgaggca    60180
gtggtggcgg ccctggctgg accacgccac aggtaccccc aattaggccg cctgtggcca   60240
ccctctcagg ccctctgtgc ccccatctgt cctctgctatc ttccccctgg               60300
ttccccccgac tcccaggccc tgagcgtcag gacgtgctca ggcctcctgg gtcgggggt    60360
gcctcactgg ctgcagaccc ctgggctgac tatgtcctct cctggctatg ccccagccct   60420
tccaacagtg ggagtctcgg agcttgcccc gatgacacat ggtggtcgag cagcgatctc   60480
acctgggacc cagcagcact gcgttattct gtttttgttt ctttttgaga tggagtctcg   60540
ctctgtcact gcaggctgga gtgcagtggc atgatctcag ctcactgcaa tctctacctc   60600
ccgggttcaa gtgatcctcc tgcctcagcc tcccaagtaa ctgagactac aagcatgtgc   60660
cccactccag gccttttttt ttttttttg gagacggtgt cttgccctgt cgcccaggct   60720
acagtgcaat ggcgtgattg cggctcacta caacccccac ctccaggtt caaaggattc    60780
tcctgcctca gcctcccaag tagctgggat tacaggtgcc cgccaccacg cccagctaat   60840
tttcgtattt ttagtagaga tggggtttca ccatattggc caggctggtc tcgaacctct   60900
gacttcaggt gatccgcccg cctcagcctc ccacagtgct gggattacag gcgtcagcca   60960
ccgtgcccgg cctgttctgt ttttctaact ctcacacagc ctcctgggtt ttcccggtc    61020
ctctgagtc ggcccactct gcaccccagc ccgcgctggc tctgctcctc agctgccctg    61080
cccacctctg tcttgtccca ccgcgctggc ctgtgtcttg tgcctgcact gtcccggct    61140
actccgcatg ggaagggtgg ctctcgggcc ttgggccatg caggcggagg gggtctggct   61200
gggagtctcc ctgcatggaa ggctggctct cagtgctgcc tgcccacagt catccactcc   61260
ggggactact tcctgtttga gtccgacagt gaggaagagg aggaggctgt tcctgaagac   61320
ccgaggccgt cggcacagag tgccttccag gtgaggtggg agagcccgt cggcccact     61380
ccaaccacag agcttgtggt cctgaccag ggcagcatag agggtgtcag atgccccag     61440
ggcctgggag ccgagctcct ccacctccag ttagcccacc ccgccccatc caggcctccc   61500
aagtcccatc ggaaaccagg ctacagggac atgggtcagt tgtagcctgc tgccccacgg   61560
tcttggctct gaccacccag gttctggtgg ctgcccgtgg cctgacctgt gagaccggcc   61620
caacacctttt gtgctggccg cctgctgtc ctgggtccat cttttgggccc ctggctcttg   61680
gtgttagacc agcccaccca actcctgaat gggtgggagt cttccccccac agcccctcag   61740
ggtccccatc cgggagggc tcagggacac ggaggtccct gggagacaca gagcagggat   61800
ctggatctgg cgcccggctt gcccaacccc agcttcccgc ctgggtctga tggctcggga   61860
ggccgggtcc taaccgggg gctggccgac agctggcgta ccaggcatgg gtgaccaacg   61920
cccaggcggt gctgaggcgg cggcagcagg agcaggagca ggcaaggcag gaacaggcag   61980
gacagctacc cacaggtgag ctgggggggcg tgggggactct gagggggaagc cgcgggactg  62040
ccagtcactc accagcatcc tgtgcccagg aggtggtccc agccaggagg tggagccagc   62100
agagggcccc gaggaggcag cggcaggtac gtgggcccgg ggctgggag tggaggtct     62160
ctcttggccc cacaggctgc ccctccagcg ccccctcccg ccctccccgca ggccggagcc   62220
atgtggtgca gagggtgctg agcacggcgc agttcctgtg gatgctgggg caggcgctag   62280
tggatgagct gacacgctgg ctgcaggagt tcacccggca ccacgcacgc atgagcgacg   62340
tgctgcgggc agagcgctac ctcctcacac aggagctcct gcaggtgagc ctgcccgtgc   62400
accacgctcg tccctgctct gcctgactac gcccctgcct gcttaacagc ctagtcccgc   62460
gcccactgca cgaaacccccg tgtggggaca agagctggac gcagccctga gcccctgct   62520
gtgccctgca gggcggcgaa gtgcacaggg gcgtgctgga tcagctgtac acaagccagg   62580
ccgaggccac gctgccaggc cccaccgagg cccccaatgc cccaagcacc gtgtccaggt   62640
aggtgcgggg gtgacccgag cccagctgc tgccctggt gtgtgggcat cgcctagcca    62700
tccccgaccc tcgccattcc cttgtacccc aaaggaccgt gggcactttc caccctgacc   62760
ctccctgtag cctgggtca ggccatagag caggattctc tgtgactcgg cttccctccc    62820
cagtggctg ggcgcggagg agccactcag cagcatgacg gacgacatgg gcagccccct   62880
gagcaccggc taccacacgc gcagtggcag tgaggaggca gtcaccgacc ccggggagcg   62940
tgaggctggt gcctctctgt accagggact gatgcggacg gccagcgagc tgctcctgga   63000
caggtggggg cgggacgcgc acaacaccag cctcaccatg gccctcgggg agcagccgaa   63060
cagggcagg agactgactg tgaccggcaa cagatcgggc cgtcatgcct tcgggcagtc   63120
ccagactccc ccaaacgc gggtctccct gtaggcgcct gaggcatccca gagctggagg   63180
aggcagagct gtttgcggag gggcagggcc gggcgctgcg gctgctgcgg ccgtgtacc    63240
agtgtgtggc cgcccactcg gagctgctct gctacttcat catcatcctc aaccacatgg   63300
tcacggcctc cgccggctcg ctggtgctgc ccgtgctcgt cttcctgtgg gccatgctgt   63360
cgatcccgag gcccagcaag cgcttctgga tgacggccat cgtcttcacc gaggtgggcc   63420
gaggccgcgg ggaggggc gcccggccca ccgcgccgtg accctcccg cgtgctgagc     63480
```

```
cccctccccc acagatcgcg gtggtcgtca agtacctgtt ccagtttggg ttcttcccct   63540
ggaacagcca cgtggtgctg cggcgctacg agaacaagcc ctacttcccg ccccgcatcc   63600
tgggcctgga gaagactgac ggctacatca agtacgacct ggtgcagctc atggccctt    63660
tcttccaccg ctcccagctg ctggtgagtg tgagccttgg ctggcaatgc ggggctgggc   63720
aggccctctg ggcacctgtg ctctccacca gggaggcaag gccccctcac cacacccctcc  63780
cgccctcag tgctatggcc tctgggacca tgaggaggac tcaccatcca aggagcatga    63840
caagagcggc gaggaggagc agggagccga ggaggggcca ggggtgcctg cggccaccac   63900
cgaagaccac attcaggtgg aagccagggt cggacccacg gacgggaccc cagaacccca   63960
agtggagctc aggcccgtg atacgaggcg catcagtcta cgttttagaa gaaggaagaa    64020
ggaggccca gcacggaaag gagcggcagc catcggtata agcgccctgc ctcacaacct    64080
cctgcctacc cagttttctg agtggggcta ctgcagggag ggtctttctc agatgagacg   64140
gccaagccca gtgcgaggcc cacctggatc ccaggaaggt gccacttctg agccacagct   64200
cccggctctg cctacagagc cgtccctgac tgctgccccc ggggatgctc cccacgtgta   64260
gggtgactgt tggcctgggc tggcccctca cagttgcccg agacagagga cacagcccca  64320
gctgtctcct tgccagtgac actgggagct ttcctgtgct ccgtctgctt gtctgtcaaa   64380
cagggagaat gccagcctct tagggtggtc aggagccatg agccaggccc agtccccagg   64440
gggcccaggc agaagtcagc ttttcccctac agaagctgag gacagggagg aagaagaggg   64500
ggaggaagag aaagaggccc ccacggggag agagaaggag ccaagccgct ctggaggaag   64560
agtaagggcg gccgggcggc ggctgcaggg cttctgcctg tccctgtgag tgatggcggc   64620
cggggggcagc tgggggagtgg gggtggggag gcgggtactg ggcccaggct gagcgccccc   64680
ttccgcaggg cccagggcac atatcggccg ctacggcgct tcttccacga catcctgcac   64740
accaagtacc gcgcagccac cgacgtctat gccctcatgt tcctggctga tgttgtcgac   64800
ttcatcatca tcatttttgg cttctggccc ttttgggtga gccaggcccg ggacccaaac   64860
ccagtgtacg cagagctcag cagccaccca catccctgg gcttggctcc ccctgacctg    64920
tgctctcctg gccacagaag cactcggcgg ccacagacat cacgtcctcc ctatcagacg   64980
accaggtacc cgaggctttc ctggtcatgc tgctgatcca gttcagtgac atggtggttg   65040
accgcgccct ctacctgcgc aagaccgtgc tgggcaagct ggccttccag gtggcgctga   65100
tgctggccat ccacctatgg atgttcttca tcctgcccgc cgtcactgag aggtggggcc   65160
acgcgtgggg gcgctcggtc tccaggggcg gggcagtgca ggctggggc cctgcggggc     65220
tgtttctgat ggggtccttg acctggccat cccgccccag gatgttcaac cagaatgtgg   65280
tggcccagct ctggtacttc gtgaagtgca tctacttcgc cctgtccgcc taccagatcc    65340
gctgcggcta ccccacccgc atcctcggca acttcctcac caagaagtac aatcatctca   65400
acctcttcct cttccagggg tgagtgcagg tccgccgggg tggggtcac ggcccgggca    65460
tgagggagcc cacctgacgg gaaccctggc tgtgggcagg ttccggctgg tgccgttcct   65520
ggtggagctg cgggcagtga tggactgggt gtggacggc accacgctgt ccctgtccag   65580
ctggatgtgt gtggaggaca tctatgccaa catcttcatc atcaaatgca gccgagagac   65640
agagaaggtg cctgggccca gggcggggc cgggacaagg gccagggata tgccctctcc    65700
ctaagacaga ggcactgctg ccacgagaac ccgtggtgct ggaggcctc ccagggctcg    65760
gagccatgg ggacatgagg cgagcccacc cactagctga tcacgaggcc agtgatcttg    65820
gcagctgcga gtgagtgctg ggcgcagaag tgggcagcgg agttggtcct gttccaggca   65880
ggctggcagc agagcagggc ctggtgcagg gaggaccgga cagccactgt ttgctgcatt   65940
cttgtttaat ggccttttctc agagagaatt cgtgcgtcag accactcccc cacgtaaaaa  66000
gtacaactca gggttttcta gtgattcac agttgagcat ctgcctttctc accacttcaa   66060
aaagaaaccc cgggccgggc acagcggctc accctcatca tcccagcact gtaagagacc   66120
caggagggag gtactgctca aggccaggag ttcaagatct gcacgccac aagcgagacc    66180
ctgcctcagc aaatgtaaaa ataaaacaat tagctgcaa tggcagctca tgcctatggt    66240
cccagcactt tgggaggcca aaggaggagg atcagttgag gccaggagtt ttaagaccag   66300
cctgggcaac atagtgagtg agactctctc tacaaaaaaa taaacgttag ctgggtgtga   66360
tggtgcacac ttgtgctccc agctactctg gaggctgagg tgggaggatg gcttgaggcc   66420
aggagtacag ggctgcatta agcctgatca caccactgca ctccagcttg gcaacagag    66480
tgagaccctg tctctaaaaa agtaaaaaga agaaacccaa tgcccattgg ctgtcactcg   66540
gtttcccctc ccctgccccc tagtaacccc ttgtctaggt cctggttcta tgagatttgc   66600
ctacagtgga tatttcatga aaacaggctc agacagcgtt tgtcctttg taatcagctt    66660
tccttgctca gcatggtgtc tctgaggtcc acccacgtgg cagtatgcc ttcctgttta    66720
tgggcaaatg atattctgtg gcatggatgg accacaacat gtcatctgt tgatgggctg   66780
ttgcccgtga tgctgccagg cacgccggtg tacacgtctg tgtcccgtg ccctggtcc    66840
tgtggctgca cgccagggcc ggaagtgctg gtggtggttt ccatcatgag gagctgctgg   66900
ttttccatag cagctccacc atctaaggtt cccaccacca acacgaggtt gcggtttctc    66960
cacatcctca acaacctgtt actatgtctt ttttgttctg gccatgctgc tgaacgggtg   67020
gcttgctgtg ggctcttctc agttcccgt tgaccgacgt tgagcgtctt ttcatgtgct   67080
tggccattttg tgtatcttct ctggggaaat gtctattcaa atcctttctc catagtttag   67140
ttgggcttt t gagataggat ctcaggctga agtgcagtgg catgacctc actcactgta   67200
gcctctgcct cccaggttca agcgattctc ccacctcagc ctcccgagta gctgggacta   67260
caggtgtgca ccaccaggcc tggctagtct ttttgtattt tgccaggtt cgtctcaaac    67320
tcctgacctc aaagtgctgg gatgacaagt gtgagccgcc acaccagca gttgggttga   67380
ttttattag agttttttct gttttctgc agatacattg gctagaatg actgaattgg    67440
aagaattctc tgtattctct ggttgctaga accttatcaa ttaaaatttg cagaaaattt    67500
ctccaattct atggactgtc tcttaaattt tcttggtgtc tttggaagca caaagtattt    67560
attttggtaa tatctggttt acttttgttc cttcgccaa tccaggttca tgaagatttg    67620
cccgttttct tctaaagtt ctatagtttt agctctgaag tttcgctctt tgatccactt    67680
tgaggtaaat tttggcacat ggtatgaggc aggagttgcg tttcattctc ctgcctgggg   67740
cggtgcctgc accgtgttga aaaggttgt ccgttcccac tgaacggtca cagctccctt    67800
gtctaagatc aacgacccct gaacatgagg gttccaactg gactcttagt tctactccac   67860
tgtcctgt ctgcccacca ttactaccgc tgtgccatac tgaggtcagg ctggggcttt      67920
tctgggctgc tgggtgagct ggagaatgcg gttgtgtgac ccgcaggaag ggcgagctg    67980
agcgtatgac ctgtgtcgtt ccctccagaa aatacccgca gcccaaaggg cagaagaaga    68040
agaagatcgt caagtacggc atgggtgcc tcatcatcct cttcctcatc gccatcatct   68100
ggttcccact gctcttcatg tcgctggtgc gctccggtgg tggggttgtc aaccagccca   68160
tcgatgtcac cgtcaccctg aagctgggcg gctatgagg gagcatgtgt gggtccggcct  68220
```

```
gtccattccc atcccctggg ggttctggcc aaggtggtgc accacccca gccgctcctc      68280
cacgctcatc ttcgtggccc cgtgtccccg tgcctgcccc agccgctgtt caccatgagc      68340
gcccagcagc cgtccatcat ccccttcacg gcccaggcct atgaggagct gtcccggcag      68400
tttgacccc agccggtaag tggcctctgc cctgtgaaag ctggtgtggg gaggcggctg       68460
cagtcactga gggtgtcact tgtacccagc tggccatgca gttcatcagc cagtacagcc      68520
ctgaggacat cgtcacggcg cagattgagg gcagctccgg ggcgctgtgg cgcatcagtc      68580
cccccagccg tgcccagatg aagcgggagc tctacaacgg cacggccgac atcaccctgc      68640
gcttcacctg gaacttccag aggttcgtcc tggacttggg gcagtgcctg ggtgggtgga      68700
cccactacag tgggtcacgc tgtgttccca ccccaggga cctggcgaag ggaggcactg       68760
tggagtatgc caacgagaag cacatgctgg ccctggcccc caacagcact gcacggcggc      68820
agctggccag cctgctcgag ggcacctcgg accagtctgt gtgagtgaag ggcccggtg       68880
gtgggcagga gggctgtgcc aggttggctg gccaggcct gacctgccag cacctccctg       68940
cagggtcatc cctaatctct tccccaagta catccgtgcc cccaacgggc ccgaagccaa      69000
ccctgtgaag cagctgcagc ccagtgagta tgggcgtggg ggttggggga ggctagagag      69060
gggtgacctg cggcctcaac gatcttctcc ctccatccca gatgaggagg ccgactacct      69120
cggcgtgcgt atccagctgc ggagggagca gggtgcgggg gccaccggct tcctcgaatg      69180
gtgggtcatc gagctgcagg agtgccggac cgactgcaac ctgctgccca tggtcatttt      69240
cagtgacaag gtcagcccac cgagcctcgg cttcctggct ggctacgggt gagtgagtgg      69300
ctggggggc accccgcagc tcggggggct ccggcggcc ccaggactca ccagcttccc        69360
ccgcagcatc atggggctgt acgtgtccat cgtgctggtc atcggcaagt tcgtgcgcgg      69420
attcttcagc gagatctcgc actccattat gttcgaggag ctgccgtgcg tggaccgcat      69480
cctcaagctc tgccaggaca tcttcctggt gcgggagact gcgggactg agctggagga       69540
ggagttgtac gccaagctca tcttcctcta ccgctcaccg gagaccatga tcaagtggac      69600
tcgtgagaag gagtaggagc tgctgctggc gcccgagagg gaaggagccg gctgctggg      69660
cagcgtggcc acaaggggcg gcactcctca ggccggggga gccactgccc cgtccaaggc      69720
cgccagctgt gatgcatcct cccggcctgc ctgagcccctg atgctgctgt cagagaagga      69780
cactcgtgcc ccacgggctg cgtgcgctg ccgtccccca cgtgtactgt agagtttttt       69840
ttttaattaa aaaatgtttt atttatacaa atggacaatc aga                       69883

SEQ ID NO: 2            moltype = RNA  length = 8089
FEATURE                 Location/Qualifiers
source                  1..8089
                        mol_type = mRNA
                        organism = Homo sapiens
SEQUENCE: 2
gggagccgcc gtccggccca gctcggcccc agtgagccga gcgctgcgct ccgccgaggg        60
gcagggcggt cgcctgagcg agcgcgggcc cgggacgtcg gcaccggcgg ggcggccgaa       120
ggagaaggag gaagaggaga aggcggcgcg cgggtcccccg cgggtcagcc atggcgcgcc     180
ggccccgggg ccccccgcacc gccccatagc gccgcggcc ccgccggtc tgggccggg         240
cctgggcccct ccagccatgg agccgcacg gctcggcgcg gtcctgtact ggctgctgct       300
gccctgcgcg ctgctggctg cctgcctgct ccgcttcagc ggactctcgc tggtctacct      360
gctcttcctg ctgctgctgc cctggttccc cggccccacc cgatgcggcc tccaaggtca       420
cacaggccgc ctcctgcggg cattgctggg cctcagcctg ctcttcctgg tggcccatct      480
cgccctccag atctgcctgc atattgtgcc ccgcctggac cagctcctgg gacccagctg      540
cagccgctgg gagaccctct cgcgacacat aggggtcaca aggctggacc tgaaggacat      600
ccccaacgcc atcggctgg tggccccctga cctgggcatc ttggtggtct cctctgtctg       660
cctccgcatc tgcgggcgcc ttgcaaggaa cacccgtgca agccacatc cacggggagct      720
ggatgatgat gagagggatg tggatgccaa cccgacggca gggctgcagg aagcagcaac      780
gctgccccct acacggaggt cacgctggcc cgctcgtttc cgagtcacgg cccactggct      840
gctggtggcg gctgggcggg tcctggccgt aacactgctt gcactggcag gcatcgccca      900
ccccctcggcc ctctccagtg tctacctgct gctcttcctg gccctctgca cctggtgggc     960
ctgccacttt cccatcagca ctcggggctt cagcagactc tgcgtcgcgg tgggggtcttt  1020
cggcgccggc catctcatct gcctctactg ctaccagatg cccttggcac aggctctgct    1080
cccgcctgcc ggcatctggg ctagggtgct gggtctcaag gacttcgtgg gtcccaccaa    1140
ctgctccagc ccccacgcgc tggtcctcaa caccggcctg gactggggcctg tgtatgccag   1200
cccccggcgtc ctcctgctgc tgtgctacgc cacggcctct ctgcgcaagc tccgcgcgta  1260
ccgcccctcc ggcagagga aggagcggc aaagggtatgagctcgggg agctggagct       1320
agcagagctg gaccagtggc cccaggaacg ggagtctgac cagcacgtgg tgcccacagc    1380
acccgacacc gaggctgata actgcatcgt gcacgagctg accggccaga gctccgtcct   1440
gcggcggcct gtgcggccca agcgggctga gccaggcga gcgtctccgc tccacagcgt    1500
gggcaccctc atcatggacc agagctatgt gtgcgcgctc attgccatga tggtatggag   1560
catcacctac cacagctggc tgaccttcgt actgctgctc tgggcctgcc tcatctggac   1620
ggtgcgcagc cgccaccaac tggccatgct gtgctcgccc tgcatcctgc tgtatgggat   1680
gacgctgtgc tgcctacgct acgtgtgggc catggacctg cgccctgac tgcccaccac    1740
cctgggcccc gtcagcctgc gccagctggg gctggagcac accgctacc cctgtctgga    1800
ccttggtgcc atgttgctct acaccctgac ctttctggcc ctgctgcgcc agtttgtgaa   1860
agagaagctg ctgaagtggg cagagtctcc agctgcgctg acgagggtca ccgtggcaga  1920
cacagagccc acgcggacgc agacgtgtgtt gcagagcctg ggggagctgg tgaagggcgt  1980
gtacgccaag tactggggatc atgtgtgtgc tggcatgttc atcgtggtca gcttcgcgg   2040
ccgcctcgtg gtctacaaga ttgtctacat gttcctcttc ctgctctgcc tcaccctctt   2100
ccaggtctac tacagcctgt ggcggaagct gctcaaggcc ttctggtggc tcgtggtggc   2160
ctacaccatg ctggtctca tcgccgctcta caccttccag ttccaggact ccctgccta    2220
ctggggcaac ctcactggct tcaccgacga gcagctgggg gacctgggcc tggagcagtt   2280
cagcgtgctg gagctcttct ccagcatcct ggtgcccggc ttcttcctgc tggcatcgcat  2340
cctgcagctg cactacttcc acaggcctt catgcagctc accgacatg agcacgtgcc   2400
cctgcctggc acgcgcctcc cgcgctgggc tcagcagcag gatgcagtga gtgggacccc  2460
actgctgcgg gaggagcagc aggagcatca gcagcagcag caggaggagg aggaggagga  2520
ggaggactcc agggagcagg gctggggcgt ggccactccc caccagccca cgcaggtgcc  2580
tgaagggca gccaagtggg gcctggtggc tgagcggctg ctggagctgg cagccggctt   2640
```

```
ctcggacgtc ctctcacgcg tgcaggtgtt cctgcggcgg ctgctggagc ttcacgtttt   2700
caagctggtg gccctgtaca ccgtctgggt ggccctgaag gaggtgtcgg tgatgaacct   2760
gctgctggtg gtgctgtggg ccttcgccct gccctaccca cgcttccggc ccatggcctc   2820
ctgcctgtcc accgtgtgga cctgcgtcat catcgtgtgt aagatgctgt accagctcaa   2880
ggttgtcaac ccccaggagt attccagcaa ctgcaccgaa ccctccccca acagcaccaa   2940
cttgctgccc acggagatca gccagtccct gctgtaccgg gggcccgtgg acctgccaa    3000
ctggtttggg gtgcggaaag ggttccccaa cctgggctac atccagaacc acctgcaagt   3060
gctgctgctg ctggtattcg aggccatcgt gtaccggcgc caggagcact accgccggca   3120
gcaccagctg gccccgctgc ctgcccaggc cgtgtttgcc agcggcaccc gccagcagct   3180
ggaccaggat ctgctcggct gcctcaagta cttcatcaac ttcttcttct acaaattcgg   3240
gctggagatc tgcttcctga tggccgtgaa cgtgatcggg cagcgcatga actttctggt   3300
gaccctgcac ggttgctggc tggtggccat cctcacccgc aggcaccgcc aggccattgc   3360
ccgcctctgg cccaactact gcctcttcct ggcgctgttc ctgctgtacc agtacctgct   3420
gtgcctgggg atgccccgg ccctgtgcat tgattatccc tggcgctgga gccgggccgt    3480
ccccatgaac tccgcactca tcaagtggct gtacctgcct gatttcttcc gggcccccaa   3540
ctccaccaac ctcatcagcg actttctcct gctgctgtgc gcctccagc agtggcaggt    3600
gttctcagct gagcgcacag aggagtggca gcgcatggct ggcgtcaaca ccgaccgcct   3660
ggagccgctg cggggggagc ccaaccccgt gcccaacttt atccactgca ggtcctacct   3720
tgacatgctg aaggtggccg tcttccgata cctgttctgg ctggtgctgg tggtggtgtt   3780
tgtcacgggg gccacccgca tcagcatctt cgggctgggc tacctgctgg cctgcttcta   3840
cctgctgctc ttcggcacgg ccctgctgca gagggacaca cgggcccgcc tcgtgctgtg   3900
ggactgcctc attctgtaca acgtcaccgt catcatctcc aagaacatgc tgtcgctcct   3960
ggcctgcgtc ttcgtggagc agatgcagac cggcttctgc tgggtcatcc agctcttcag   4020
ccttgtatgc accgtcaagg gctactatga ccccaaggag atgatggaca gagaccagga   4080
ctgcctgctg cctgtggagg aggctggcat catctgggag agcgtctgct tcttcttcct   4140
gctgctgcag cgccgcgtct tccttagcca ttactacctg cacgtcaggg ccgacctcca   4200
ggccaccgcc ctgctagcct caggggctt cgccctctac aacgctgcca acctcaagag    4260
cattgacttt caccgcagga tagaggagaa gtccctggcc cagctgaaaa cagagatgga   4320
gcgtatccgt gccaagcagg agaagcacag gcagggccgg gtggaccgca gtcgccccca   4380
ggacaccctg ggcccaagg accccgacct ggagccaggg cccgacagtc caggggctg    4440
ctcccccgcca cggaggcagt ggtggcggcc ctggctggga cacgccacag tcatccactc   4500
cggggactac ttcctgtttg agtccgacag tgaggaagag gaggaggctg ttcctgaaga   4560
cccgaggccg tcggcacaga gtgccttcca gctggcgtac caggcatggg tgaccaacgc   4620
ccaggcggtg ctgaggcggc ggcagcagga gcaggagcag aacaggcagg               4680
acagctaccc acaggaggtg gtcccagcca ggaggtggga ccagcagagg gccccgagg    4740
ggcagcggca ggccggagcc atgtggtgca gaggtgctg agcacggcgc agttcctgtg    4800
gatgctgggg caggcgctag tggatgagct gacacgctgg ctgcaggagt tcacccggca   4860
ccacggcacc atgagcgacg tgctgcgggc agagcgctac ctcctcacac aggagctcct   4920
gcagggcggg gaagtgcaca ggggcgtgct ggatcagctg tacacaagcc aggccgaggc   4980
cacgctgcca ggccccaccg aggccccaa tgccccaagc accgtgtcca gtgggctggg    5040
cgcggaggag ccactcagca gcatgacaga cgacatgggc agcccctga gcaccggcta    5100
ccacacgcgc agtggcagtg aggaggcagt caccgacccc ggggagcgtg aggctggtgc   5160
ctctctgtac cagggactga tgcggacggc cagcgagctg cctcctggaca ggccgctgc    5220
catcccagag ctggaggagg cagagctgtt tgcggagggg cagggccggg cgctgcggct   5280
gctgcgggcc gtgtaccagt gtgtggccgc ccactcggag ctgctctgct acttcatcat   5340
catcctcaac cacatggtca cggcctccgc cggctcgctg gtgctgcccg tgctcgtctt   5400
cctgtgggac atgctgtcga tcccgaggcc cagcaagcgc ttctgatga cggccatcgt   5460
cttcaccgag atcgcggtgg tcgtcaagta cctgttccag tttgggttct tccctggaa    5520
cagccacgtg gtgctgcggc gctacgagaa caagccctac ttcccgcccc gcatcctggg   5580
cctggagaag actgacggct acatcaagta cgacctggtg cagctcatgg ccctttttctt   5640
ccaccgctcc cagctgctgt gctatgcct ctgggaccat gaggaggact caccatccaa    5700
ggagcatgac aagagcggcg aggaggagca gggagccgag gaggggccag gggtgcctgc   5760
ggccaccacc gaagaccaca ttcaggtgga agccagggtc ggacccacgg acgggacccc   5820
agaaccccaa gtgagctca ggcccgtga tacgaggcgc atcagtctac gttttagaag     5880
aaggaagaag gagggcccag cacggaaagg gccggcaggc atcgaagctg aggacaggga   5940
ggaagaagaa ggggaggaag agaaagaggc cccacgggg agagagaaga ggcaagccg    6000
ctctggagga agagtaaggg cggccgggcg gcggctgcag ggcttctgcc tgtccctggc   6060
ccagggcaca tatcggccgc tacgcgctt cttccacgac atcctgcaca ccaagtaccg    6120
cgcagccacc gacgtctatg ccctcatgtt cctggctgat gttgtcgact tcatcatcat   6180
cattttggc ttctgggcct ttgggaagca ctcggcggcc acagacatca cgtcctccct    6240
atcagacgac caggtacccg aggctttcct ggtcatgctg ctgatccagt tcagtaccat   6300
ggtggttgac cgcgccctct acctgcgcaa gaccgtgctg ggcaagctgg ccttccaggt   6360
ggcgctggtg ctggccatcc acctatggat gttcttcatc ctgccccgcc tcactgagag   6420
gatgttcaac cagaatgtgg tggcccagct ctggtacttc gtgaagtgca tctacttcgc   6480
cctgtccgcc taccagatcc gctgcggcta cccccacccg cctatccggca acttcctcac    6540
caagaagtac aatcatctca acctcttcct cttccagggg ttccgctgg tgccgttcct    6600
ggtggagctg cgggcagtga tggactgggt gtggacggac accacgctgt ccctgtccag   6660
ctggatgtgt gtggaggaca tctatgccaa catcttcatc atcaaatgca gccgagagac   6720
agagaagaaa tacccgcagc ccaaagggca gaagaagaaa aagatcgtca agtacgcat    6780
gggtggcctc atcatcctct tcctcatcgc catcatctgg ttcccactgc tcttcatgtc   6840
gctggtgcgc tccgtggttg gggttgtcaa ccagcccatc gatgtcaccg tcaccctgaa   6900
gctgggcggc tatgagccgc tgttccacat gagcgcccag cagccgtcca tcatcccctt   6960
cacggcccag gcctatgagg agctgtccg gcagtttgac cccagccgc tggcatgca     7020
gttcatcagc cagtacagcc ctgaggacat cgtcacggcg cagattgagg gcagctccgg   7080
ggcgctgtgg cgcatcagtc cccccagccg tgcccagatg aagggggagc tctacaacgg   7140
cacggccgac atcaccctgc gcttcacctg gaacttccag agggacctgg cgaagggagg   7200
cactgtggag tatgccaacg agaagcacat gctggccctg gccccaaca gcactgcacg   7260
gcggcagctg gccagcctgc tcgagggcac ctcggaccag tctgtggtca tccctaatct   7320
cttccccaag tacatccgtg ccccccaacgg gcccgaagcc aaccctgtga agcagctgca   7380
```

```
gcccaatgag gaggccgact acctcggcgt gcgtatccag ctgcggaggg agcagggtgc   7440
gggggccacc ggcttcctcg aatggtgggt catcgagctg caggagtgcc ggaccgactg   7500
caacctgctg cccatggtca ttttcagtga caaggtcagc ccaccgagcc tcggcttcct   7560
ggctggctac ggcatcatgg ggctgtacgt gtccatcgtg ctggtcatcg gcaagttcgt   7620
gcgcggattc ttcagcgaga tctcgcactc cattatgttc gggagctgc cgtgcgtgga   7680
ccgcatcctc aagctctgcc aggacatctt cctggtgcgg gagactcggg agctggagct   7740
ggaggaggag ttgtacgcca agctcatctt cctctaccgc tcaccggaga ccatgatcaa   7800
gtggactcgt gagaaggagt aggagctgct gctggcgccc gagagggaag gagccggcct   7860
gctgggcagc gtggccacaa ggggcggcac tcctcaggcc gggggagcca ctgccccgtc   7920
caaggccgcc agctgtgatg catcctcccg gcctgcctga gccctgatgc tgctgtcaga   7980
gaaggacact cgctccccac ggcctgcgtg cgctgccgt ccccacgtg tactgtagag   8040
tttttttttt aattaaaaaa tgttttattt atacaaatgg acaatcaga            8089

SEQ ID NO: 3          moltype = DNA    length = 8089
FEATURE               Location/Qualifiers
source                1..8089
                      mol_type = other DNA
                      organism = Homo sapiens
SEQUENCE: 3
gggagccgcc gtccggccca gctcggcccc agtgagccga gcgctgcgct ccgccgaggg     60
gcagggcggt cgcctgagcg agcgcgggcc cgggacgtcg gcaccggcgg ggcggccgaa    120
ggagaaggag gaagaggaga aggcggcgcg cgggtcagcc atggcgcgcc                180
ggccccgggg cccccgcacc gcccatagc gccgcgccgt ccgctcggtc tgggccggcc    240
cctgggccct ccagccatgg agccgcacgt gctcggcgcg gtcctgtact ggctgctgct    300
gccctgcgcg ctgctggctg cctgcctgct ccgcttcagc ggactctcgc tggtctacct    360
gctcttcctg ctgctgctcc cctgctccgc ccggccccacc ccgatgcggcc tccaaggtca    420
cacaggccgc ctcctgcggg cattgctggg cctcagcctg ctcttcctgg tggcccatct    480
cgccctccag atctgcctgc atattgtgcc ccgcctggac cagctcctgg gacccagctg    540
cagccgctgg gagaccctct cgcgacacat aggggtcaca aggctggacc tgaaggacat    600
ccccaacgcc atccggctga tggccccctga cctgggcatc ttggtggtct cctctgtctg    660
cctcggcatc tgcggggcgcc ttgcaaggaa cacccggcag agcccacatc cacgggagct    720
ggatgatgat gagaggaatg tggatgccag cccgacggca gggctgcagg aagcagcaac    780
gctggccccct acacggaggt cacggctggc cgctcgtttc cgagtcacgg cccactggct    840
gctggtggcg gctgggcggg tcctggccgt aacactgctt gcactggcag gcatcgccca    900
ccctcggcc ctctccagtg tctacctgct gctcttcctg gccctctcca cctggtaggg    960
ctgccacttt cccatcagca ctcggggctt cagcagactc tgcgtcgcgg tggggtgctt   1020
cggcgccggc catctcatct gcctctactg ctaccagatg cccttggcac aggctctgct   1080
cccgcctgcc ggcatctggg ctagggtgct gggtctcaag gacttcgtgg gtcccaccaa   1140
ctgctccagc ccccacgcgc tggtcctcaa caccggcctg ggactggcctg tgtatgccag   1200
cccggcgtc ctcctgctgc tgtgctacgc cacggcctct ctgcgcaagc tccgcgcgta   1260
ccgccctcc ggcagagga aggaggcgg aaaggggtat gaggcgggg agctggagct   1320
agcagagctg gaccagtggc cccaggaacg ggagtctgac cagcacgtgg tgcccacagc   1380
acccgacacc gaggctgata actgcatcgt gcacggaggtca accgccaga gtcccgtcct   1440
gcggcggcct gtgcggccca gcgggctga gcccagggag gcgtctccgc tccacagcct   1500
gggccacctc atcatggacc agagctatgt gtgcgcgctc attgccatga tggtatggag   1560
catcacctac cacagctggc tgaccttcgt actgctgctc tgggcctgcc tcatctggac   1620
ggtgcgtgcc cgccaccaac tggccatgct gtgctgccc tgcatcctgc tgtatgggat   1680
gacgctgtgc tgcctacgct acgtgtgggc catggacctg cgccctgagc tgcccaccac   1740
cctgggcccc gtcagcctgc gccagctggg gctggagcac acccgctacc cctgtctgga   1800
ccttggtgcc atgttgctct acaccctgac cttctgctc ctgctgcgcc agtttgtgaa   1860
agagaagctg ctgaagtggg cagagtctcc agctgcgctg acggaggtca ccgtggcaga   1920
cacagagccc acgcggacgc agacgctgtt gcagagcctg ggggagctgg tgaagggcgt   1980
gtacgccaag tactgatct atgtgtgtgc tggcatgttc atcgtggtca gcttcgccgg   2040
ccgcctcgtg gtctacaaga ttgtctacat gttcctcttc ctgctctgcc tcaccctctt   2100
ccaggtctac tacacgctgt ggcggaagct gctcaaggcc ttctggttgg tcgtggtggc   2160
ctacaccatg ctggtcctca tcgccgtcta caccttccag ttccaggact tccctgccta   2220
ctggcgcaac tcactggct tcaccgacga gcagctgggg gacctgggcc tggagcagtt   2280
cagcgtgtcc gagctcttct ccagcatcct ggtgcccggc ttcttcctcc tggcctgcat   2340
cctgcagctg cactactcc acaggcccctt catgcagctc accgacatgg agcacgtgtc   2400
cctgctggc acgcgcctcc gcgcgtgggc tcacaggcag gatgcagtga gtgggaccc   2460
actgctgcgg gaggagcagc aggagcatca gcagcagcag caggaggagg aggaggaga   2520
ggaggactcc agggacgagg ggctgggcgt ggccactccc caccaggcca cgcaggtgcc   2580
tgaaggggca gccaagtggg gcctggtggc tgagcggctg ctggagctgg cagccggctt   2640
ctcggacgtc ctctcacgcg tgcaggtgtt cctgcggcg ctgctggagc ttcacgtttt   2700
caagctggtg gccctgtaca ccgtctgggt ggccctgaag gaggtgtcgg tgatgaacct   2760
gctgctggtg gtgctgtggg gccttcgccct gccctaccca cgcttccggc ccatggcctc   2820
ctgcctgtcc accgtgtgga cctgcgtcat catcgtgtgt aagatgctgt accagctcaa   2880
ggttgtcaac ccccaggagt attccagcaa ctgcaccgag ccctcccca acagcaccaa   2940
cttgctgccc acggagatca gccagtccct gctgtaccgg gggcccgtgg accctgccaa   3000
ctggtttggg gtgcgaaag ggttcccaa cctgggctac atccagaacc acctgcaagt   3060
gctgctgctg ctggtatcg aggccatcgt gtaccggcgc caggagcact accgccggca   3120
gcaccagctg gccccgctgc ctgcccaggc cgtgtttgcc agcggcaccc gccagcgct   3180
ggaccaggat ctgctcggct gcctcaagta cttcatcaac ttcttcttct acaaattcgg   3240
gctggagatc tgcttcctga tggcctgatga cgtgatcggg cagcgcatga actttcggtt   3300
gaccctgcac ggttgctggc tggtggccat cctcaccgc aggcaccgcc aggccattgc   3360
ccgcctctgg cccaactact gcctcttcct ggcgctgttc ctgctgtacc agtacctgct   3420
gtgcctgggg atgccccgg ccctgtgcat tgattatccc tggcgctgga gccgggccgt   3480
cccatgaac tccgcactca tcaagtggct gtacctgcct gatttcttcc gggccccccaa   3540
ctccaccaac ctcatcagcg actttctcct gctgctgtgc gcctcccagc agtggcaggt   3600
```

```
gttctcagct gagcgcacag aggagtggca gcgcatggct ggcgtcaaca ccgaccgcct   3660
ggagccgctg cggggggagc ccaaccccgt gcccaacttt atccactgca ggtcctacct   3720
tgacatgctg aaggtggccg tcttccgata cctgttctgg ctggtgctgg tggtggtgtt   3780
tgtcacgggg gccacccgca tcagcatctt cgggctgggc tacctgctgg cctgcttcta   3840
cctgctgctc ttcggcacgg ccctgctgca gagggacaca cgggcccgcc tcgtgctgtg   3900
ggactgcctc attctgtaca acgtcaccgt catcatctcc aagaacatgc tgtcgctctc   3960
ggcctgcgtc ttcgtggagc agatgcagac cggcttctgc tgggtcatcc agctcttcag   4020
ccttgtatgc accgtcaagg gctactatga ccccaaggag atgatggaca gagaccagga   4080
ctgcctgctg cctgtggagg aggctggcat catctgggac agcgtctgct tcttcttcct   4140
gctgctgcag cgccgcgtct tccttagcca ttactacctg cacgtcaggg ccgacctcca   4200
ggccaccgcc ctgctagcct ccaggggctt cgccctctac aacgctgcca acctcaagag   4260
cattgacttt caccgcagga tagaggagaa gtccctggcc cagctgaaaa gacagatgga   4320
gcgtatccgt gccaagcagg agaagcacag gcagggccgg gtggaccgca gtcgccccca   4380
ggacaccctg ggcccaagg accccggcct ggagccaggg cccgcagtc agggggctc   4440
ctccccgcca cggaggcagt ggtggcgcc ctggctggac cacgccacag tcatccactc   4500
cggggactac ttcctgtttg agtccgacag tgaggaagag gaggaggctg ttcctgaaga   4560
cccgaggccg tcggcacaga gtgccttcca gctggcgtac caggcatggg tgaccaacgc   4620
ccaggcggtg ctgaggcggc ggcagcagga gcaggagcag gcaaggcagg aacaggcagg   4680
acagctaccc acaggaggtg gtcccagcca ggaggtggag ccagcagagg gccccgagga   4740
ggcagcggca ggccggagcc atgtggtgca gagggtgctg agcacggcgc agttcctgtg   4800
gatgctgggg caggcgctag tggatgagct gacacgctgg ctgcaggagt tcacccggca   4860
cccacgcacc atgagcgacg tgctgcgggc agagcgctac ctcctcacac aggagctcct   4920
gcagggcggc gaagtgcaca gggcgtgct ggatcagctg tacacaagcc aggccgaggc   4980
cacgctgcca ggccccaccg aggccccaa tgcccaagc accgtgtcca gtgggctggg   5040
cgcggaggag ccactcagca gcatgacaga cgacatgggc agcccctga gcaccggcta   5100
ccacacgcgc agtggcagtg aggaggcagt caccgacccc ggggagcgtg aggctggtgc   5160
ctctctgtac cagggactga tgcggacggc cagcgagtg ctctcggaca ggcgcctgcg   5220
catcccagag ctggaggagg cagagctgtt tgcggaggca cagggccggg cgctgcggct   5280
gctgcgggcc gtgtaccagt gtgtggccgc ccactcggag ctgctctgct acttcatcat   5340
catcctcaac cacatggtca cggcctccgc cggctgctg gtgctgcccg tgctcgtctt   5400
cctgtgggcc atgctgtcga tcccgaggcc cagcaagcgc ttctgatga cggccatcgt   5460
cttcaccgag atcgcggtgg tcgtcaagta cctgttccag tttgggttct tccccctgaa   5520
cagccacgtg gtgctgcggc gctacgaaa caagccctac ttcccgcccc gcatcctgcg   5580
cctggagaag actgacgct acatcaagta cgacctggtg cagctcatgg ccctttttctt   5640
ccaccgctcc cagctgctgt gctatggcct ctgggaccat gaggaggact caccatccaa   5700
ggagcatgac aagagcggcg aggaggagca gggagccgag gaggggccag gggtgcctgc   5760
ggccaccacc gaagaccaca ttcaggtgga agccagggtc ggaccacgg acgggacccc   5820
agaacccaa gtggagctca ggccccgtga tacgaggcgg atcagtctac gttttagaag   5880
aaggaagaag gagggcccag cacgcgaaagg agccggcagc atcgaagctg aggacaggga   5940
ggaagaagag gggaggaag agaaaggagc cccacggg agagaagaga ggccaagccg   6000
ctctggagga gagtaaggg cggccgggcg gcggctgcag ggcttctgcc tgtccctggc   6060
ccagggcaca tatcggccgc tacggcgctt cttccacgag atcctgcaca ccaagtaccg   6120
cgcagccagc gacgtctatg ccctcatgtt cctggctgat gttgtcgact tcatcatcat   6180
cattttggc ttctgggcct tgggaagca ctccggcggcc acagacatca cgtcctccct   6240
atcagacgac caggtacccg aggctttcct ggtcatgctg ctgatccagt tcagtaccat   6300
ggtggttgac cgccgccctct acctgcgcaa gaccgtgctg gcaagctgg ccttccaggt   6360
ggcgctggtg ctggccatcc acctatggat gttcttcatc ctgccccgcc tcactgagag   6420
gatgttcaac cagaatgtgg tggcccagct ctggtacttc gtgaagtgca tctacttcgg   6480
cctgtccgcc taccagatcc gctgcggcta ccccacccgc atcctcggca acttcctcac   6540
caagaagtac aatcatctca acctcttcct cttccagggg ttccggctgg tgccgttcct   6600
ggtggagctg cggcagtga tggactgggt gtggacggac accacgctgt ccctgtccag   6660
ctggatgtgt gtggaggaca tctatgccaa catcttcatc atcaaatgca gccgagagac   6720
agagaagaaa tacccgcagc ccaaagggca gaagaagag aagatcgtca gtacggcat   6780
gggtggcctc atcatcctct tcctcatcgc catcatctgg ttcccactgc tcttcatgtc   6840
gctggtgcgc tccgtggttg gggttgtcaa ccagcccatc gatgtcaccg tcaccctgaa   6900
gctgggcggc tatgagccgc tgttaccat gagcgcccag cagccgtcca tcatcccctt   6960
cacggcccag gcctatgagg agctgtcccg gcagtttgac ccccagccgc tggccatgca   7020
gttcatcagc cagtacagcc ctgaggacat cgtcacggcg cagattgagg gcagctccgg   7080
ggcgctgtgg cgcatcagtc cccccagccg tgcccagatg aagcgggagc tctacaacgg   7140
cacggccgac atcaccctgc gcttcacctg gaacttccag agggacctgg cgaagggagg   7200
cactgtggag tatgccaacg agaagcacat gctggccctg gccccaaca gcactgcacg   7260
gcggcagctg gccagcctgc tcgagggcac ctcggaccga tctgtggtca tccctaatct   7320
cttccccaag tacatccgtg ccccaacgg gcccgaagcc aaccctgtga gcagctgca   7380
gcccaatgag gaggcggact acctggcgt gcgtatccga ctgcggaggg agcagggtgc   7440
gggggccacc ggcttcctcg aatggtgggt catcgagctg caggagtgcc ggaccgactg   7500
caacctgctg cccatggtca ttttcagtga caggtcagcc caccgagcc tcggcttcct   7560
ggctggctac ggcatcatgg ggctgtacgt gtccatcgtg ctggtcatcg gcaagttcgt   7620
gcgcggattc ttcagcgaga tctcgcactc cattatgttc gaggagctgc cgtgcgtgga   7680
ccgcatcctc aagctctgcc aggacatctt cctggtgcgg agcgaggctc   7740
ggaggaggag ttgtacgcca agctcatctt cctctaccgc tcaccggaga ccatgatcaa   7800
gtggactcgt gagaaggagt aggagctgct gctggcgccc gagagggaag gagccggcct   7860
gctgggcagc gtgccacaa ggggcggcac tcctcaggcc gggggagcca ctgccccgtc   7920
caaggccgcc agctgtgatg catcctcccg gcctgcctga gccctgatgc tgctgtcaga   7980
gaaggacact gcgtccccac ggcctgcgtg gcgctgccgt cccccacgtg tactgtagag   8040
ttttttttttt aattaaaaaa tgttttattt atacaaatgg acaatcaga                8089
```

```
SEQ ID NO: 4            moltype = AA  length = 2521
FEATURE                 Location/Qualifiers
source                  1..2521
                        mol_type = protein
                        organism = Homo sapiens
SEQUENCE: 4
MEPHVLGAVL YWLLLPCALL AACLLRFSGL SLVYLLFLLL LPWFPGPTRC GLQGHTGRLL   60
RALLGLSLLF LVAHLALQIC LHIVPRLDQL LGPSCSRWET LSRHIGVTRL DLKDIPNAIR  120
LVAPDLGILV VSSVCLGICG RLARNTRQSP HPRELDDDER DVDASPTAGL QEAATLAPTR  180
RSRLAARFRV TAHWLLVAAG RVLAVTLLAL AGIAHPSALS SVYLLLFLAL CTWWACHFPI  240
STRGFSRLCV AVGCFGAGHL ICLYCYQMPL AQALLPPAGI WARVLGLKDF VGPTNCSSPH  300
ALVLNTGLDW PVYASPGVLL LLCYATASLR KLRAYRPSGQ RKEAAKGYEA RELELAELDQ  360
WPQERESDQH VVPTAPDTEA DNCIVHELTG QSSVLRRPVR PKRAEPREAS PLHSLGHLIM  420
DQSYVCALIA MMVWSITYHS WLTFVLLLWA CLIWTVRSRH QLAMLCSPCI LLYGMTLCCL  480
RYVWAMDLRP ELPTTLGPVS LRQLGLEHTR YPCLDLGAML LYTLTFWLLL RQFVKEKLLK  540
WAESPAALTE VTVADTEPTR TQTLLQSLGE LVKGVYAKYW IYVCAGMFIV VSFAGRLVVY  600
KIVYMFLFLL CLTLFQVYYS LWRKLLKAFW WLVVAYTMLV LIAVYTFQFQ DFPAYWRNLT  660
GFTDEQLGDL GLEQFSVSEL FSSILVPGFF LLACILQLHY FHRPFMQLTD MEHVSLPGTR  720
LPRWAHRQDA VSGTPLLREE QQEHQQQQQE EEEEEEDSRD EGLGVATPHQ ATQVPEGAAK  780
WGLVAERLLE LAAGFSDVLS RVQVFLRRLL ELHVFKLVAL YTVWVALKEV SVMNLLLVVL  840
WAFALPYPRF RPMASCLSTV WTCVIIVCKM LYQLKVVNPQ EYSSNCTEPF PNSTNLLPTE  900
ISQSLLYRGP VDPANWFGVR KGFPNLGYIQ NHLQVLLLLV FEAIVYRRQE HYRRQHQLAP  960
LPAQAVFASG TRQQLDQDLL GCLKYFINFF FYKFGLEICF LMAVNVIGQR MNFLVTLHGC 1020
WLVAILTRRH RQAIARLWPN YCLFLALFLL YQYLLCLGMP PALCIDYPWR WSRAVPMNSA 1080
LIKWLYLPDF FRAPNSTNLI SDFLLLLCAS QQWQVFSAER TEEWQRMAGV NTDRLEPLRG 1140
EPNPVPNFIH CRSYLDMLKV AVFRYLFWLV LVVVFVTGAT RISIFGLGYL LACFYLLLFG 1200
TALLQRDTRA RLVLWDCLIL YNVTVIISKN MLSLLACVFV EQMQTGFCWV IQLFSLVCTV 1260
KGYYDPKEMM DRDQDCLLPV EEAGIIWDSV CFFFLLLQRR VFLSHYYLHV RADLQATALL 1320
ASRGFALYNA ANLKSIDFHR RIEEKSLAQL KRQMERIRAK QEKHRQGRVD RSRPQDTLGP 1380
KDPGLEPGPD SPGGSSPPRR QWWRPWLDHA TVIHSGDYFL FESDSEEEEE AVPEDPRPSA 1440
QSAFQLAYQA WVTNAQAVLR RRQQEQEQAR QEQAGQLPTG GGPSQEVEPA EGPEEAAAGR 1500
SHVVQRVLST AQFLWMLGQA LVDELTRWLQ EFTRHHGTMS DVLRAERYLL TQELLQGGEV 1560
HRGVLDQLYT SQAEATLPGP TEAPNAPSTV SSGLGAEEPL SSMTDDMGSP LSTGYHTRSG 1620
SEEEAVTDPGE REAGASLYQG LMRTASELLL DRRLRIPELE EAELFAEGQG RALRLLRAVY 1680
QCVAAHSELL CYFIIILNHM VTASAGSLVL PVLVFLWAML SIPRPSKRFW MTAIVFTEIA 1740
VVVVKYLFQFG FFPWNSHVVL RRYENKPYFP PRILGLEKTD GYIKYDLVQL MALFFHRSQL 1800
LCYGLWDHEE DSPSKEHDKS GEEEQGAEEG PGVPAATTED HIQVEARVGP TDGTPEPQVE 1860
LRPRDTRRIS LRFRRRKKEG PARKGAAAIE AEDREEEEGE EEKEAPTGRE KRPSRSGGRV 1920
RAAGRRLQGF CLSLAQGTYR PLRRFFHDIL HTKYRAATDV YALMFLADVV DFIIIIFGFW 1980
AFGKHSAATD ITSSLSDDQV PEAFLVMLLI QFSTMVVDRA LYLRKTVLGK LAFQVALVLA 2040
IHLWMFFILP AVTERMFNQN VVAQLWYFVK CIYFALSAYQ IRCGYPTRIL GNFLTKKYNH 2100
LNLFLFQGFR LVPFLVELRA VMDWVWTDTT LSLSSWMCVE DIYANIFIIK CSRETEKKYP 2160
QPKGQKKKI VKYGMGGLII LFLIAIIWFP LLFMSLVRSV VGVVNQPIDV TVTLKLGGYE 2220
PLFTMSAQQP SIIPFTAQAY EELSRQFDPQ PLAMQFISQY SPEDIVTAQI EGSSGALWRI 2280
SPPSRAQMKR ELYNGTADIT LRFTWNFQRD LAKGGTVEYA NEKHMLALAP NSTARRQLAS 2340
LLEGTSDQSV VIPNLFPKYI RAPNGPEANP VKQLQPNEEA DYLGVRIQLR REQGAGATGF 2400
LEWWVIELQE CRTDCNLLPM VIFSDKVSPP SLGFLAGYGI MGLYVSIVLV IGKFVRGFFS 2460
EISHSIMFEE LPCVDRILKL CQDIFLVRET RELELEEELY AKLIFLYRSP ETMIKWTREK 2520
E                                                                2521
```

What is claimed is:

1. A method of reducing development of varicose veins in a patient who has an increased risk of developing varicose veins, the method comprising administering to the patient a therapeutic agent that inhibits the development of varicose veins, wherein the patient has a Piezo Type Mechanosensitive Ion Channel Component 1 (PIEZO1) predicted loss-of-function variant nucleic acid molecule selected from the group consisting of nucleotide polymorphism 16:88715629: G:A, 16:88715728:G:T, 16:88715767:G:A, 16:88715802:C: A, 16:88715822:ACCAG:A, 16:88715987:A:AC, 16:88716359:A:G, 16:88716570:C:T, 16:88716874:G:A, 16:88717213:T:A, 16:88719588:G:A, 16:88719722:C:G, 16:88719870:G:T, 16:88720068:CCT:C, 16:88720229:C:A, 16:88720248:TAGGG:T, 16:88720394:C:T, 16:88720644: GC:G, 16:88720698:TG:T, 16:88720698:T:TG, 16:88721165:C:A, 16:88721268:CT:C, 16:88721307:G:A, 16:88721586:G:C, 16:88721652:G:C, 16:88722217:C:T, 16:88722605:T:TG, 16:88723005:C:CCGGCCTG, 16:88723253:G:A, 16:88723311:G:T, 16:88725081:C:A, 16:88726282:G:A, 16:88726546:C:T, 16:88726619:G:A, 16:88726924:G:A, 16:88727038:C:T, 16:88727072:TC:T, 16:88727163:G:A, 16:88731768:AG:A, 16:88732334:C:G, 16:88732411:CG:C, 16:88732720:TG:T, 16:88733326:G:C, 16:88733337:TACAC:T, 16:88733587:C:A, 16:88733965: TC:T, 16:88734017:C:A, 16:88734042:C:CA, 16:88734679:C:T, 16:88734909:A:AT, 16:88736167:CAG: C, 16:88736324:G:A, 16:88736391:G:T, 16:88736409:C:T, 16:88736671:G:A, 16:88737557:A:C, 16:88737727:C:G, 16:88737815:C:T, 16:88738283: G:C, 16:88738637: G:A, 16:88738735:TC:T, 16:88741477:C:T, 16:88742306:GT:G, 16:88749399:G:A, and 16:88784929:C:T, or selected from an mRNA molecule produced therefrom, or a cDNA molecule produced from the mRNA molecule.

2. The method of claim 1, wherein the patient is heterozygous for the PIEZO1 predicted loss-of-function variant nucleic acid molecule.

3. The method of claim 1, wherein the patient is homozygous for the PIEZO1 predicted loss-of-function variant nucleic acid molecule.

4. The method of claim 1, wherein the therapeutic agent that inhibits the development of varicose veins comprises a flavonoid.

5. The method of claim 4, wherein the flavonoid comprises diosmin.

6. The method of claim 4, wherein the flavonoid comprises hesperidin.

7. The method of claim 1, wherein the therapeutic agent that inhibits the development of varicose veins comprises an anti-inflammatory agent.

8. The method of claim 7, wherein the anti-inflammatory agent comprises ibuprofen.

9. The method of claim 7, wherein the anti-inflammatory agent comprises aspirin.

* * * * *